US012806198B2

(12) United States Patent
Sturino et al.

(10) Patent No.: US 12,806,198 B2
(45) Date of Patent: Nov. 24, 2026

(54) LINE-1 INHIBITORS TO TREAT DISEASE

(71) Applicant: Transposon Therapeutics, Inc., San Diego, CA (US)

(72) Inventors: Claudio Sturino, Québec (CA); Malay Doshi, Ontario (CA); Eckard Weber, San Diego, CA (US); Michael G. Cordingley, Québec (CA)

(73) Assignee: Transposon Therapeutics, Inc., San Diego, CA (US)

(*) Notice: Subject to any disclaimer, the term of this patent is extended or adjusted under 35 U.S.C. 154(b) by 668 days.

(21) Appl. No.: 18/246,415

(22) PCT Filed: Sep. 23, 2021

(86) PCT No.: PCT/US2021/051716
§ 371 (c)(1),
(2) Date: Mar. 23, 2023

(87) PCT Pub. No.: WO2022/066880
PCT Pub. Date: Mar. 31, 2022

(65) Prior Publication Data

US 2023/0414616 A1 Dec. 28, 2023

Related U.S. Application Data

(60) Provisional application No. 63/161,055, filed on Mar. 15, 2021, provisional application No. 63/082,185, filed on Sep. 23, 2020.

(51) Int. Cl.
*A61K 31/513* (2006.01)
*A61K 31/52* (2006.01)

(52) U.S. Cl.
CPC ............ *A61K 31/513* (2013.01); *A61K 31/52* (2013.01)

(58) Field of Classification Search
CPC .............................. A61K 31/513; A61K 31/52
See application file for complete search history.

(56) References Cited

U.S. PATENT DOCUMENTS

| | | | |
|---|---|---|---|
| 4,172,896 | A | 10/1979 | Uno et al. |
| 4,582,788 | A | 4/1986 | Erlich |
| 4,683,194 | A | 7/1987 | Saiki et al. |
| 4,683,202 | A | 7/1987 | Mullis |
| 5,192,749 | A | 3/1993 | O-Yang et al. |
| 5,223,490 | A | 6/1993 | Hart et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,627,160 | A | 5/1997 | Lin et al. |
| 5,731,000 | A | 3/1998 | Ruff et al. |
| 5,763,493 | A | 6/1998 | Ruff et al. |
| 6,110,973 | A | 8/2000 | Young |
| 6,291,670 | B1 | 9/2001 | Ohrui et al. |
| 6,333,315 | B1 | 12/2001 | Ohrui et al. |
| 6,403,568 | B1 | 6/2002 | Ohrui et al. |
| 6,531,581 | B1 | 3/2003 | Nardone et al. |
| 7,339,053 | B2 | 3/2008 | Kohgo et al. |
| 7,589,078 | B2 | 9/2009 | Cheng et al. |
| 7,625,877 | B2 | 12/2009 | Kohgo et al. |
| 8,173,623 | B2 | 5/2012 | Crawford et al. |
| 8,193,165 | B2 | 6/2012 | Cheng et al. |
| 8,334,295 | B2 | 12/2012 | Guo et al. |
| 8,354,421 | B2 | 1/2013 | He et al. |
| 8,431,745 | B2 | 4/2013 | Crawford et al. |
| 8,445,669 | B2 | 5/2013 | Sato et al. |
| 8,513,205 | B2 | 8/2013 | Anderson et al. |
| 9,051,288 | B2 | 6/2015 | Nagai et al. |
| 9,126,971 | B2 | 9/2015 | Cheng et al. |
| 9,212,174 | B2 | 12/2015 | Iriyama et al. |
| 9,221,832 | B2 | 12/2015 | Hilpert et al. |
| 9,249,171 | B2 | 2/2016 | Ortiz et al. |
| 9,422,605 | B2 | 8/2016 | Dubnau et al. |
| 9,441,223 | B2 | 9/2016 | Dubnau et al. |
| 9,777,035 | B2 | 10/2017 | Girijavallabhan et al. |

(Continued)

FOREIGN PATENT DOCUMENTS

| | | |
|---|---|---|
| CN | 105012305 A | 11/2015 |
| JP | 6767011 B2 | 10/2020 |

(Continued)

OTHER PUBLICATIONS

Ohrui (J. Med. Chem vol. 43 pp. 4516-4525 published 2000) (Year: 2000).*
Nomura (J. Med. Chem vol. 42 pp. 2901-2908 published 1999). (Year: 1999).*
Kirby (Antimicrobial Agents and Chemotherapeutic Agents vol. 57 pp. 6254-6264 published 2013) (Year: 2013).*

(Continued)

*Primary Examiner* — George W Kosturko
(74) *Attorney, Agent, or Firm* — Sterne, Kessler, Goldstein & Fox P.L.L.C.

(57) ABSTRACT

The present disclosure provides methods of treating or preventing a disease, disorder, or condition in a subject in need thereof, the methods comprising administering to the subject a therapeutically effective amount of a compound of Formula I: or a pharmaceutically acceptable salt or solvate thereof, or a tautomer thereof, wherein $R^1$, $R^2$, and B are defined as set forth in the specification.

I

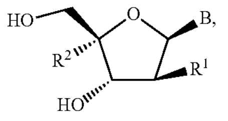

17 Claims, No Drawings

(56) References Cited

U.S. PATENT DOCUMENTS

| | | | |
|---|---|---|---|
| 9,822,138 B2 | 11/2017 | Vachal et al. | |
| 9,993,547 B2 | 6/2018 | Stenler et al. | |
| 10,059,940 B2 | 8/2018 | Zhong et al. | |
| 10,071,985 B2 | 9/2018 | Graupe et al. | |
| 10,100,307 B2 * | 10/2018 | Prochiantz | A61K 31/7072 |
| 10,258,575 B2 | 4/2019 | Li | |
| 10,266,558 B2 | 4/2019 | Ivachtchenko et al. | |
| 10,363,220 B2 | 7/2019 | Li | |
| 10,449,208 B2 | 10/2019 | Da Costa et al. | |
| 10,450,335 B2 | 10/2019 | Fu et al. | |
| 10,479,801 B2 | 11/2019 | Graham et al. | |
| 10,519,159 B2 | 12/2019 | Paparin et al. | |
| 10,537,589 B2 | 1/2020 | Hazuda et al. | |
| 10,654,827 B2 | 5/2020 | Graupe et al. | |
| 10,857,122 B2 * | 12/2020 | Cottam | C07D 493/04 |
| 10,933,067 B2 | 3/2021 | Mitsuya et al. | |
| 11,793,814 B2 | 10/2023 | Sedivy et al. | |
| 12,508,038 B2 | 12/2025 | Micault | |
| 2003/0003468 A1 | 1/2003 | Crow | |
| 2004/0229262 A1 | 11/2004 | Franco et al. | |
| 2005/0113324 A1 | 5/2005 | Bondarev et al. | |
| 2006/0020042 A1 | 1/2006 | McDonald et al. | |
| 2006/0160087 A1 | 7/2006 | McGrath et al. | |
| 2010/0048726 A1 | 2/2010 | McDonald et al. | |
| 2011/0150997 A1 | 6/2011 | Shah et al. | |
| 2014/0113952 A1 | 4/2014 | Dubnau et al. | |
| 2015/0018297 A1 | 1/2015 | Jo et al. | |
| 2015/0073056 A1 | 3/2015 | Muhammad et al. | |
| 2015/0104511 A1 | 4/2015 | Malhotra et al. | |
| 2015/0290235 A1 | 10/2015 | Gros et al. | |
| 2016/0130260 A1 | 5/2016 | Ortiz et al. | |
| 2016/0339019 A1 | 11/2016 | Laberge et al. | |
| 2017/0224680 A2 | 8/2017 | Laberge et al. | |
| 2017/0335320 A1 | 11/2017 | Prochiantz et al. | |
| 2017/0356054 A1 | 12/2017 | Ting et al. | |
| 2018/0002366 A1 | 1/2018 | Girijavallabhan et al. | |
| 2018/0050000 A1 | 2/2018 | Mckearn et al. | |
| 2018/0065999 A1 | 3/2018 | Vachal et al. | |
| 2018/0153859 A1 | 6/2018 | Didsbury et al. | |
| 2018/0185372 A1 | 7/2018 | Schinazi et al. | |
| 2018/0230464 A1 | 8/2018 | Zhong | |
| 2018/0305688 A1 | 10/2018 | Zhong | |
| 2018/0362562 A1 | 12/2018 | Raheem et al. | |
| 2019/0022115 A1 | 1/2019 | Girijavallabhan et al. | |
| 2019/0038659 A1 | 2/2019 | Nath et al. | |
| 2019/0055273 A1 | 2/2019 | Beigelman et al. | |
| 2019/0083478 A1 | 3/2019 | Houston et al. | |
| 2019/0084963 A1 | 3/2019 | Shi | |
| 2019/0177326 A1 | 6/2019 | Alexandre et al. | |
| 2019/0183912 A1 | 6/2019 | Da Costa et al. | |
| 2019/0185508 A1 | 6/2019 | Alexandre et al. | |
| 2019/0262365 A1 | 8/2019 | Paparin et al. | |
| 2019/0315769 A1 | 10/2019 | Graham et al. | |
| 2019/0321380 A1 | 10/2019 | De Lera et al. | |
| 2019/0388336 A1 | 12/2019 | Barrett et al. | |
| 2019/0388590 A1 | 12/2019 | Barrett et al. | |
| 2020/0010834 A1 | 1/2020 | Novick et al. | |
| 2020/0010868 A1 | 1/2020 | Duan et al. | |
| 2020/0038389 A1 | 2/2020 | Bauer et al. | |
| 2020/0101098 A1 | 4/2020 | Hazuda et al. | |
| 2020/0138845 A1 | 5/2020 | Scott | |
| 2020/0171020 A1 | 6/2020 | Balan et al. | |
| 2020/0253888 A1 | 8/2020 | Ramos et al. | |
| 2020/0345699 A1 | 11/2020 | Cho et al. | |
| 2024/0173346 A1 | 5/2024 | Weber et al. | |

FOREIGN PATENT DOCUMENTS

| | | | | |
|---|---|---|---|---|
| RU | 2322989 C2 | 4/2008 | | |
| WO | WO-2000069876 A1 | 11/2000 | | |
| WO | WO-2003026589 A2 | 4/2003 | | |
| WO | WO-2003026675 A1 | 4/2003 | | |
| WO | WO-2005020885 A2 | 3/2005 | | |
| WO | WO-2008054808 A2 | 5/2008 | | |
| WO | WO-2009153009 A1 | 12/2009 | | |
| WO | WO-2012068636 A1 | 5/2012 | | |
| WO | WO-2013057469 A1 | 4/2013 | | |
| WO | WO-2014184553 A1 | 11/2014 | | |
| WO | WO-2016005327 A1 | 1/2016 | | |
| WO | WO-2016138425 A1 | 9/2016 | | |
| WO | WO-2016149561 A1 | 9/2016 | | |
| WO | WO-2017050803 A1 | 3/2017 | | |
| WO | WO-2017138022 A1 | 8/2017 | | |
| WO | WO-2018102358 A1 | 6/2018 | | |
| WO | WO-2018118826 A1 | 6/2018 | | |
| WO | WO-2018136920 A1 | 7/2018 | | |
| WO | WO-2018191093 A1 | 10/2018 | | |
| WO | WO-2018203235 A1 | 11/2018 | | |
| WO | WO-2018219977 A1 | 12/2018 | | |
| WO | WO-2019009793 A1 | 1/2019 | | |
| WO | WO-2019133712 A1 | 7/2019 | | |
| WO | WO-2019140365 A1 | 7/2019 | | |
| WO | WO-2019157087 A1 | 8/2019 | | |
| WO | WO-2019171285 A1 | 9/2019 | | |
| WO | WO-2019246422 A1 | 12/2019 | | |
| WO | WO-2020007070 A1 | 1/2020 | | |
| WO | WO-2020014041 A1 | 1/2020 | | |
| WO | WO-2020018352 A1 | 1/2020 | | |
| WO | WO-2020018399 A1 | 1/2020 | | |
| WO | WO-2020031131 A1 | 2/2020 | | |
| WO | WO-2020044257 A1 | 3/2020 | | |
| WO | WO-2020053811 A1 | 3/2020 | | |
| WO | WO-2020058844 A1 | 3/2020 | | |
| WO | WO-2020081622 A1 | 4/2020 | | |
| WO | WO-2020092621 A1 | 5/2020 | | |
| WO | WO-2020128525 A1 | 6/2020 | | |
| WO | WO-2020131649 A1 | 6/2020 | | |
| WO | WO-2020142629 A1 | 7/2020 | | |
| WO | WO-2020154656 A1 * | 7/2020 | | A61P 11/00 |
| WO | WO-2020185676 A1 | 9/2020 | | |
| WO | WO-2021041317 A1 | 3/2021 | | |
| WO | WO-2021188910 A1 | 9/2021 | | |
| WO | WO-2022066882 A1 | 3/2022 | | |

OTHER PUBLICATIONS

Greicius (Journal of Neurol Neurosurg Psychiatry vol. 72 pp. 691-700 Published 2002) (Year: 2002).*

Ohuri (J. Med. Chem vol. 43 pp. 4516-4525 published 2000) (Year: 2000).*

Estrada, E., et al., "In Silico Studies toward the Discovery of New Anti-HIV Nucleoside Compounds with the Use of TOPS-MODE and 2D/3D Connectivity Indices. 1. Pyrimidyl Derivatives," J. Chem. Inf. Comput. Sci. 42(5):1194-1203, American Chemical Society, United States (Jul. 2002).

Kodama, E.-I., et al., "4'-Ethynyl Nucleoside Analogs: Potent Inhibitors of Multidrug-Resistant Human Immunodeficiency Virus Variants In Vitro," Antimicrobial Agents and Chemotherapy 45(5):1539-1546, American Society for Microbiology, United States (May 2001).

Ohrui, H., "A New Paradigm for Developing Antiviral Drugs Exemplified by the Development of Supremely High Anti-HIV Active EFdA," Journal of Antivirals & Antiretrovirals 6(1):32-39, Longdom Publishing SL, Spain (Jan. 2014).

Alexandrova, E., et al., "Sense Transcripts Originated From an Internal Part of the Human Retrotransposon LINE-1 5' UTR," Gene 15(1): 46-53, Elsevier, Netherlands (Dec. 2012).

An, W., et al., "Characterization of a Synthetic Human LINE-1 Retrotransposon ORFeus-Hs," Mobile DNA 2, BioMed Central Ltd., London (Feb. 2011).

Athanikar, J., et al., "A YY1-Binding Site Is Required for Accurate Human Line-1 Transcription Initiation," Nucleic Acids Research 32(13): 3846-3855, Oxford University Press, London (2004).

Baker, D.J., et al., "Clearance of P16ink4a-positive Senescent Cells Delays Ageing-associated Disorders," Nature 479(7372):232-236, Nature Publishing Group, United Kingdom (Nov. 2011).

Baker, D.J., et al., "Naturally Occurring P16(Ink4a)-positive Cells Shorten Healthy Lifespan," Nature 530(7589):184-189, Nature Publishing Group, United Kingdom (Feb. 2016).

Benjamini, Y. and Hochberg, Y., "Controlling the False Discovery Rate: A Practical and Powerful Approach to Multiple Testing,"

(56) References Cited

OTHER PUBLICATIONS

Journal of the Royal Statistical Society. Series B (Methodological) 57(1): 289-300, Wiley, United States (1995).
Bingham, A.L., et al., "Over One Hundred Solvates of Sulfathiazole," Chemical Communications 7:603-604, Royal Society of Chemistry, United States (2001).
Bowen, L. N., et al., "HIV-associated motor neuron disease: HERV-K activation and response to antiretroviral therapy," Neurology 87(17):1756-1762, American Academy of Neurology, United States (published online Sep. 2016, published in print Oct. 2016).
Brown, J. P., et al., "Bypass of Senescence After Disruption of P21cip1/waf1 Gene in Normal Diploid Human Fibroblasts," Science 277(5327): 831-834, American Association for the Advancement of Science, United States (Aug. 1997).
Brydon, E., "CSHL neuroscientists show 'jumping genes' may contribute to aging-related brain defects," 7 pages, Cold Spring Harbor Laboratory, United States (Apr. 2013).
Bundo, M., et al., "Increased L1 Retrotransposition in the Neuronal Genome in Schizophrenia," Neuron 81(2):306-313, Cell Press, United States (Jan. 2014).
Bussian, T.J., et al., "Clearance of Senescent Glial Cells Prevents Tau-dependent Pathology and Cognitive Decline," Nature 562(7728):578-582, Nature Publishing Group, United Kingdom (Oct. 2018).
Caira, M,R., et al., "Preparation and Crystal Characterization of a Polymorph, a Monohydrate, and an Ethyl Acetate Solvate of the Antifungal Fluconazole," Journal of Pharmaceutical Sciences 93(3):601-611, American Pharmaceutical Assn, United States (2004).
Chang, J., et al., "Clearance of Senescent Cells by ABT263 Rejuvenates Aged Hematopoietic Stem Cells in Mice," Nature Medicine 22:78-83, Nature Research (2016).
Childs, B G., et al., "Cellular Senescence in Aging and Age-related Disease: From Mechanisms to Therapy," Nature Medicine 21(12):1424-1435, Nature Publishing Company, United States (Dec. 2015).
Childs, B G., et al., "Senescent Intimal Foam Cells Are Deleterious at All Stages of Atherosclerosis," Science 354(6311):472-477, American Association for the Advancement of Science, United States (Oct. 2016).
Chinta, S., et al., "Cellular Senescence Is Induced by the Environmental Neurotoxin Paraquat and Contributes to Neuropathology Linked to Parkinson's Disease," Cell Reports 22(4):930-940, Cell Press, United States (Jan. 2018).
Chu, S. C., et al., "Inhibitory effects of flavonoids on Moloney murine leukemia virus reverse transcriptase activity," Journal of Natural Products 55(2):179-183, American Chemical Society, United States (Feb. 1992).
Chung, H.Y., et al., "Molecular inflammation: underpinnings of aging and age-related diseases," Ageing Research Reviews 8(1):18-30, Elsevier Science, United Kingdom (Jan. 2009).
Coppe, J.P., et al., "The Senescence-associated Secretory Phenotype: the Dark Side of Tumor Suppression," Annual Review of Pathology 5:99-118, Annual Reviews, United States (2010).
Coufal, N. G., et al., "L1 Retrotransposition in Human Neural Progenitor Cells," Nature 460(7259): 1127-1131, Nature Publishing Group, United Kingdom (Aug. 2009).
Criscione, S.W., et al., "Transcriptional Landscape of Repetitive Elements in Normal and Cancer Human Cells," BMC Genomics 15:583, BioMed Central, United Kingdom (Jul. 2014).
Dai, L., et al., "Effect of reverse transcriptase inhibitors on LINE-1 and Ty 1 reverse transcriptase activities and on LINE-1 retrotransposition," BMC Biochem 12:18, 11 pages, BioMed Central Ltd., United Kingdom (May 2011).
De Cecco, M., et al., "Genomes of replicatively senescent cells undergo global epigenetic changes leading to gene silencing and activation of transposable elements," Aging Cell 12(2):247-256, Wiley-Blackwell Publishing Ltd., United Kingdom (published online Jan. 2013, published in print Apr. 2013).
De Cecco, M., et al., "Transposable elements become active and mobile in the genomes of aging mammalian somatic tissues," Aging 5(12):867-883, Impact Journals LLC, United States (Dec. 2013).
De Koning, A.P.J., et al., "Repetitive Elements May Comprise Over Two-thirds of the Human Genome, " PLos Genetics 7(12):e1002384, Public Library of Science, United States (Dec. 2011).
Demaria, M., et al., "An Essential Role for Senescent Cells in Optimal Wound Healing through Secretion of PDGF-AA," Developmental Cell 31(6): 722-733, Cell Press, United States (Dec. 2014).
Demaria, M., et al., "Cellular Senescence Promotes Adverse Effects of Chemotherapy and Cancer Relapse," Cancer Discovery 7(2):165-176, American Association for Cancer Research, United States (Feb. 2017).
Denli, A.M., et al., "Primate-specific ORFO Contributes to Retrotransposon-mediated Diversity," Cell 163(3):583-593, Cell Press, United States (Oct. 2015).
Dhanwani, R., et al., "Cytosolic Sensing of Immuno-stimulatory DNA, the Enemy Within," Current Opinion in Immunology 50:82-87, Elsevier, United Kingdom (Feb. 2018).
Diagnostic and Statistical Manual of Mental Disorders, Fifth Edition, pp. 602-614, American Psychiatric Association Publishing, Washington, DC (2013).
Dou, Z., et al., "Cytoplasmic Chromatin Triggers Inflammation in Senescence and Cancer," Nature 550(7676):402-406, Nature Publishing Group, United Kingdom (Oct. 2017).
Else, J., et al., "Pharmacokinetics of Lamivudine and Lamivudine-triphosphate After Administration of 300 Milligrams and 150 Milligrams Once Daily to Healthy Volunteers: Results of the ENCORE 2 Study," Antimicrobial Agents and Chemotherapy 56(3):1427-1433, American Society for Microbiology, United States (Mar. 2012).
Engel, P., "These Staggering Maps Show How Much The World's Population Is Aging," Business Insider (May 2014).
Erwin, J.A., et al., "Mobile DNA Elements in the Generation of Diversity and Complexity in the Brain," Nature Reviews. Neuroscience 15(8):497-506, Nature Publishing Group, United Kingdom (Aug. 2014).
Farr, J.N., et al., "Targeting Cellular Senescence Prevents Age-related Bone Loss in Mice," Nature Medicine 23(9):1072-1079, Nature Publishing Company, United States (Sep. 2017).
Fikes, B. J., "HIV drugs may help Alzheimer's, says study proposing an undiscovered root cause," MedicalXpress.com, 5 pages, The San Diego Union-Tribune, United States (Nov. 2018).
Fowler, B. J., et al., "Nucleoside reverse transcriptase inhibitors possess intrinsic anti-inflammatory activity," Science 346(6212):1000-1003, American Association for the Advancement of Science, United States (Nov. 2014).
Franceschi, C. and Campisi, J., "Chronic Inflammation (Inflammaging) and Its Potential Contribution to Age-associated Diseases," The Journals of Gerontology. Series A, Biological Sciences and Medical Sciences 69 Suppl 1:S4-S9, Gerontological Society of America, United States (Jun. 2014).
Frasca, D. and Blomberg, B., "Inflammaging Decreases Adaptive and Innate Immune Responses in Mice and Humans," Biogerontology 17(1):7-19, Kluwer Academic, Netherlands (Feb. 2016).
Fumagalli, M., et al., "Stable Cellular Senescence Is Associated With Persistent DDR Activation," PloS One 9(10):e110969, Public Library of Science, United States (Oct. 2014).
Gautier, G., et al., "A Type I Interferon Autocrine-paracrine Loop Is Involved in Toll-like Receptor-induced Interleukin-12p70 Secretion by Dendritic Cells," The Journal of Experimental Medicine 201(9):1435-1446, Rockefeller University Press, United States (May 2005).
Giri Repbase., 31 pages, accessed at [URL:http://www.girinst.org/repbase/update/browse.php] on Apr. 22, 2021.
Gorbunova, V., et al., "Human Genomics. Sleeping dogs of the genome," Science 346(6214): 1187-1188, American Association for the Advancement of Science, United States (Dec. 2014).
Hampel, H., et al., "Advances in the development of biomarkers for Alzheimer's disease: from CSF total tau and Abeta(1-42) proteins to phosphorylated tau protein," Brain Research Bulletin 61(3):243-253, Elsevier Inc., United States (Aug. 2003).
Han, J. S., "Non-long terminal repeat (non-LTR) retrotransposons: mechanisms, recent developments, and unanswered questions," Mobile DNA 1(1):15, 12 pages, BioMed Central Ltd., United Kingdom (May 2010).

(56) References Cited

OTHER PUBLICATIONS

Hancks, D.C. and Kazazian, H.H., Jr., "Active Human Retrotransposons: Variation and Disease," Current Opinion in Genetics & Development 22(3):191-203, Elsevier, United Kingdom (Jun. 2012).
Herbig, U., et al., "Cellular Senescence in Aging Primates," Science 311(5765):1257, American Association for the Advancement of Science, United States (Mar. 2006).
Herbig, U., et al., "Telomere Shortening Triggers Senescence of Human Cells Through a Pathway Involving Atm, P53, and P21(Cip1), but Not P16(Ink4a)," Molecular Cell 14(4):501-513, Cell Press, United States (May 2004).
Huang, C.R.L., et al., "Active Transposition in Genomes," Annual Review of Genetics 46:651-475, Annual Reviews, United States (2012).
International Search Report and Written Opinion for International Application No. PCT/US2020/015043, Commissioner for Patents, Virginia, mailed on Jul. 7, 2020.
Ishak, C.A., et al., "An RB-EZH2 Complex Mediates Silencing of Repetitive DNA Sequences," Molecular Cell 64(6):1074-1087, Cell Press, United States (Dec. 2016).
Itahana, K., et al., "Methods to Detect Biomarkers of Cellular Senescence: the Senescence-associated Beta-galactosidase Assay," Methods in Molecular Biology 371:21-31, Humana Press, United States (2007).
Ivanov, A., et al., "Lysosome-mediated Processing of Chromatin in Senescence," The Journal of Cell Biology 202(1):129-143, Rockefeller University Press, United States (Jul. 2013).
Jurk, D., et al., "Chronic Inflammation Induces Telomere Dysfunction and Accelerates Ageing in Mice," Nature Communications 2:4172, Nature Pub. Group, United Kingdom (Jun. 2014).
Kamentsky, L., et al., "Improved Structure, Function and Compatibility for CellProfiler: Modular High-Throughput Image Analysis Software," Bioinformatics 27(8):1179-1180, Oxford University Press, United Kingdom (2011).
Katoh, K. and Standley, D.M., "MAFFT Multiple Sequence Alignment Software Version 7: Improvements in Performance and Usability," Molecular Biology and Evolution 30(4):772-780, Oxford University Press, United States (Apr. 2013).
Kent, J., "UCSC In-Silico PCR," Dec. 2013, 1 page, accessed on [URL:https://genome.ucsc.edu/cgi-bin/hgPcr].
Kim, D., et al., "HISAT: A Fast Spliced Aligner With Low Memory Requirements," Nature Methods 12(4):357-360, Nature Pub. Group, United States (Apr. 2015).
Kreiling, J.A., et al., "Age-associated Increase in Heterochromatic Marks in Murine and Primate Tissues," Aging Cell 10(2):292-304, Wiley-Blackwell, United Kingdom (Apr. 2011).
Kreiling, J.A., et al., "Contribution of Retrotransposable Elements to Aging," In book: Human Retrotransposons in Health and Disease, pp. 297-321, Springer, Cham (Jan. 2017).
Langmead, B., "Aligning Short Sequencing Reads With Bowtie," Current Protocols in Bioinformatics Chapter 11:Unit 11.7, John Wiley & Sons, United States (Dec. 2010).
Le, O.N.L., et al., "Ionizing Radiation-induced Long-term Expression of Senescence Markers in Mice Is Independent of P53 and Immune Status," Aging Cell 9(3):398-409, Wiley-Blackwell, United Kingdom (Jun. 2010).
Lee, M-H., and Chun, J., "Mosaic APP Gene Recombination in Alzheimer's Disease-What's Next?," Journal of Experimental Neuroscience 13: 1179069519849669, Rockefeller University Press, United States (May 2019).
Lee, M-H., et al., "Somatic APP gene recombination in Alzheimer's disease and normal neurons," Nature 563(7733):639-645, Nature Publishing Group, United Kingdom (Nov. 2018).
Cognitive Vitality Reports, "LINE1 inhibition (with nucleoside reverse transcriptase inhibitors)," Alzheimer's Drug Discovery Foundation, Jul. 31, 2020.
Levin, J., Conference Report, "Single Doses as Low as 0.5 mg of the Novel NRTTI MK-8591 Suppress HIV for at Least Seven Days," 9th IAS Conference on HIV Science; Paris, France; Jul. 23-26, 2017, accessed at [https://www.natap.org/2017/IAS/IAS_36.htm] on May 21, 2021, 6 pages.
Li, Q., et al., "FOXA1 Mediates P16(INK4a) Activation During Cellular Senescence," The EMBO Journal 32(6):858-873, Wiley Blackwell, United Kingdom (Mar. 2013).
Li, W. et al., "The EMBL-EBI Bioinformatics Web and Programmatic Tools Framework," Nucleic Acids Research 43:W580-W584, Oxford University Press, United Kingdom (Jul. 2015).
Liao, Y., et al., "FeatureCounts: An Efficient General Purpose Program for Assigning Sequence Reads to Genomic Features," Bioinformatics 30(7):923-930, Oxford University Press, Oxford (2014).
Lopez-Otin, C., et al., "The Hallmarks of Aging," Cell 153(6):1194-1217, Cell Press, United States (Jun. 2013).
Martinez-Santibanez, G., et al., "Imaging White Adipose Tissue With Confocal Microscopy," Methods in Enzymology 537:17-30, Academic Press, United States (2014).
Mattson, M.P., "Perspective: Does Brown Fat Protect Against Diseases of Aging?," Ageing Research Reviews 9(1):69-76, Elsevier Science, United Kingdom (Jan. 2010).
Meter, M.V., et al., "SIRT6 Represses LINE1 Retrotransposons by Ribosylating KAP1 but This Repression Fails With Stress and Age," Nature Communications 5:5011, Nature Pub. Group, United Kingdom (Sep. 2014).
Michaud, K., et al., "Pharmacologic Inhibition of Cyclin-dependent Kinases 4 and 6 Arrests the Growth of Glioblastoma Multiforme Intracranial Xenografts," Cancer Research 70(8):3228-3238, American Association for Cancer Research, United States (Apr. 2010).
Moles, J-P., et al., "Cytosolic RNA:DNA Duplexes Generated by Endogenous Reverse Transcriptase Activity as Autonomous Inducers of Skin Inflammation in Psoriasis," PLoS One 12(1):e0169879, Public Library of Science, United States (Jan. 2017).
Montoya-Durango, D.E., et al., "Epigenetic Control of Mammalian Line-1 Retrotransposon by Retinoblastoma Proteins," Mutation Research 665(1-2):20-28, Elsevier, Netherlands (Jun. 2009).
Zhang, X., et al., "New Understanding of the Relevant Role of LINE-1 Retrotransposition in Human Disease and Immune Modulation," Frontiers in Cell and Developmental Biology, 8:657, doi:10.3389/fcell.2020.00657 (Aug. 2020).
NCT01767701, "Raltegravir (Isentress) Pilot Study in Relapsing Multiple Sclerosis (INSPIRE)," first posted online Jan. 14, 2013, accessed at https://clinicaltrials.gov/ct2/show/NCT01767701, accessed on May 20, 2021, 8 pages.
NCT02363452, "Reverse Transcriptase Inhibitors in AGS (RTIs in AGS)," first posted online Feb. 16, 2015, accessed at https://clinicaltrials.gov/ct2/show/NCT02363452, accessed on May 20, 2021, 9 pages.
NCT02437110, "HERV-K Suppression Using Antiretroviral Therapy in Volunteers With Amyotrophic Lateral Sclerosis (ALS)," first posted online May 7, 2015, accessed at https://clinicaltrials.gov/ct2/show/NCT02437110, accessed on May 20, 2021, 10 pages.
Olovnikov, I.A., et al., "Key Role of the Internal Region of the 5'-UTR Segment in the Transcription Acitivity of the Human L1 Retrotransposon," Molecular Biology 41(3):453-458, Pleiades Publishing, Inc. (2007).
Pawelec, G., et al., "Inflammation, Ageing and Chronic Disease," Current Opinion in Immunology 29:23-28, Elsevier, United Kingdom (Aug. 2014).
Penzkofer, T., et al., "LIBase: From Functional Annotation to Prediction of Active Line-1 Elements," Nucleic Acids Research 33(Database Issue): D498-D500, Information Retrieval ltd., United Kingdom (Jan. 2005).
Rangwala, S.H., et al., "Many LINE1 Elements Contribute to the Transcriptome of Human Somatic Cells," Genome Biology 10: R100, BioMed Central, United Kingdom (2009).
Reich, M., et al., "GenePattern 2.0," Nature Genetics 38(5):500-501, Nature Publishing Group, United States (May 2006).
Robinson, M.D., et al., "edgeR: A Bioconductor Package for Differential Expression Analysis of Digital Gene Expression Data," Bioinformatics 26(1):139-140, Oxford University Press, United Kingdom (Jan. 2010).

(56) References Cited

OTHER PUBLICATIONS

Rodic, N., et al., "Long Interspersed Element-1 Protein Expression Is a Hallmark of Many Human Cancers," The American Journal of Pathology 184(5):1280-1286, Elsevier, United States (May 2014).
Safrin, S., "Antiviral Agents (Chapter 49). In: Basic and Clinical Pharmacology," 14th Edition. Katzung BG, Masters SB, Trevor AJ (Editors). McGraw-Hill Education. (2018).
Salama, R., et al., "Cellular Senescence and Its Effector Programs," Genes & Development 28(2):99-114, Cold Spring Harbor Laboratory Press, United States (Jan. 2014).
Saleh, A., et al., "Transposable Elements, Inflammation, and Neurological Disease," Frontiers in Neurology 10: 894, Frontiers Research Foundation, Switzerland (2019).
Sanjana, N.E., et al., "Improved Vectors and Genome-wide Libraries for CRISPR Screening," Nature Methods 11(8):783-784, Nature Pub. Group, United States (Aug. 2014).
Schafer, M.J., et al., "Cellular Senescence Mediates Fibrotic Pulmonary Disease," Nature Communications 8:14532, Nature Pub. Group, United Kingdom (Feb. 2017).
Schoenmaker, M., et al., "Evidence of genetic enrichment for exceptional survival using a family approach: the Leiden Longevity Study," European Journal of Human Genetics : EJHG 14(1):79-84, Nature Publishing Group, United Kingdom (Jan. 2006).
Schorl, C. and Sedivy, J.M., "Analysis of Cell Cycle Phases and Progression in Cultured Mammalian Cells," Methods 41(2):143-150, Academic Press, United States (Feb. 2007).
Sedivy, J. M., et al., "Death by transposition—the enemy within?," Bioessays 35(12):1035-1043, John Wiley and Sons Inc., United States (published online Oct. 2013, published in print Dec. 2013).
Shalem, O., et al., "Genome-Scale CRISPR-Cas9 Knockout Screening In Human Cells, " Science, 343(6166):84-87, American Association for the Advancement of Science, United States (Jan. 2014).
Simon, M., et al., "Inhibition of retrotransposition improves health and extends lifespan of SIRT6 knockout mice," BioRXiv.org, accessed at URL:[https://www.biorxiv.org/content/10.1101/460808v1.full], 53 pages, Cold Spring Harbor Laboratory, United States (Nov. 2018).
Singh, T. and Newman, A.B., "Inflammatory Markers in Population Studies of Aging," Ageing Research Reviews 10(3):319-329, Elsevier Science, United Kingdom (Jul. 2011).
Skowron, G., and Ogden, R., eds., "Reverse transcriptase inhibitors in HIV/AIDS Therapy," pp. 1-527, Humana Press Inc., United States (2006).
Sonnier, L., et al., "Progressive loss of dopaminergic neurons in the ventral midbrain of adult mice heterozygote for Engrailed1," The Journal of Neuroscience 27(5):1063-1071, Society for Neuroscience, United States (Jan. 2007).
Stetson, D.B., et al., "Trex1 Prevents Cell-intrinsic Initiation of Autoimmunity," Cell 134(4):587-598, Cell Press, United States (Aug. 2008).
Stoddart, C.A., et al., "Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque," Antimicrobial Agents and Chemotherapy 59(7): 4190-4198, American Society for Microbiology, United States (Jul. 2015).
Suarez, N.A., et al., "LINE-1 Retrotransposons in Healthy and Diseased Human Brain," Developmental Neurobiology 78(5): 434-455, Wiley Subscription Services, United States (May 2018).
Subramanian, A., et al., "Gene Set Enrichment Analysis: a Knowledge-based Approach for Interpreting Genome-wide Expression Profiles," Proceedings of the National Academy of Sciences 102(43):15545-15550, The National Academy of Sciences, United States (2005).
Sun, X., et al., "Transcription Factor Profiling Reveals Molecular Choreography and Key Regulators of Human Retrotransposon Expression," Proceedings of the National Academy of Sciences of the United States of America 115(24):E5526-E5535, National Academy of Sciences, United States (Jun. 2018).
Takahashi, A., et al., "Downregulation of Cytoplasmic Dnases Is Implicated in Cytoplasmic DNA Accumulation and SASP in Senescent Cells," Nature Communications 9:1249, Nature Research, United Kingdom (2018).
Tam, O. H., et al., "Postmortem Cortex Samples Identify Distinct Molecular Subtypes of ALS: Retrotransposon Activation, Oxidative Stress, and Activated Glia," Cell Reports 29(5):1164-1177, Cell Press, United States (Oct. 2019).
Tchkonia, T., et al., "Fat Tissue, Aging, and Cellular Senescence," Aging Cell 9(5): 667-684, Wiley-Blackwell, United Kingdom (Oct. 2010).
Thomas, C.A., et al., "Modeling of TREX1-Dependent Autoimmune Disease using Human Stem Cells Highlights L1 Accumulation as a Source of Neuroinflammation," Cell Stem Cell 21(3):319-331, Cell Press, United States (Sep. 2017).
Toti, L., et al., "Gastric dysregulation induced by microinjection of 6-OHDA in the substantia nigra pars compacta of rats is determined by alterations in the brain-gut axis," American Journal of Physiology—Gastrointestinal and Liver Physiology 307(10):G1013-G1023, American Physiological Society, United States (published online Oct. 2014, published in print Nov. 2014).
University of Texas Health Science Center at San Antonio, "First-in-human trial of senolytic drugs encouraging: Small pilot study points to feasibility of larger trials in age-related diseases," ScienceDaily.com, accessed at URL:[www.sciencedaily.com/releases/2019/01/190107112944.htm] on May 20, 2021, 3 pages (Jan. 2019).
Van Tonder, E.C., et al., "Preparation and Physicochemical Characterization of 5 Niclosamide Solvates and 1 Hemisolvate," AAPS PharmSciTech 5(1):E12, American Association of Pharmaceutical Scientists, United States (2004).
Volkman, H.E. and Stetson D.B., "The Enemy Within: Endogenous Retroelements and Autoimmune Disease," Nature Immunology 15(5): 415-422, Nature America Inc., United States (May 2014).
Waaijer, M.E., et al., "The Number of p16INK4a Positive Cells in Human Skin Reflects Biological Age," Aging Cell 11(4):722-725, Wiley-Blackwell, United Kingdom (Aug. 2012).
Waterhouse, A.M., et al., "Jalview Version 2—A Multiple Sequence Alignment Editor and Analysis Workbench," Bioinformatics 25(9): 1189-1191, Oxford University Press, United Kingdom (May 2009).
West, A.P., et al., "Mitochondrial DNA in Innate Immune Responses and Inflammatory Pathology," Nature Reviews. Immunology 17(6):363-375, Nature Pub. Group, United Kingdom (Jun. 2017).
West, A.P., et al., "Mitochondrial DNA Stress Primes the Antiviral Innate Immune Response," Nature 520:553-557, Nature Publishing Group, United Kingdom (2015).
Westarp, M. E., et al., "Antiretroviral therapy in sporadic adult amyotrophic lateral sclerosis," NeuroReport 4(6):819-822, Rapid Communications of Oxford Ltd., United Kingdom (Jun. 1993).
Wikipedia., "Senotherapy," 5 pages, accessed at [URL:https://en.wikipedia.org/wiki/Senotherapy] on Apr. 23, 2021.
Xie, Y., et al., "Characterization of L1 Retrotransposition With High-throughput Dual-luciferase Assays," Nucleic Acids Research 39(3):e16, Oxford University Press, United Kingdom (Feb. 2011).
Xu, M., et al., "Senolytics Improve Physical Function and Increase Lifespan in Old Age," Nature Medicine 24(8): 1246-1256, Nature Publishing Company, United States (Aug. 2018).
Ye, J., et al., "Primer-BLAST: a Tool to Design Target-specific Primers for Polymerase Chain Reaction," BMC *Bioinformatics* 13:134 (Jun. 2012).
Zhao, B., et al., "Somatic LINE-1 Retrotransposition in Cortical Neurons and Non-brain Tissues of Rett Patients and Healthy Individuals," Plos Genetics 15(4):e1008043, Public Library of Science, United States (Apr. 2019).
Zhu, Y., et al., "The Achilles' Heel of Senescent Cells: From Transcriptome to Senolytic Drugs," Aging Cell 14(4):644-658, Wiley-Blackwell, United Kingdom (Aug. 2015).
Li, W., et al., "Activation of Transposable Elements During Aging and Neuronal Decline in *Drosophila,*" Nature Neuroscience, 16(5):529-531, Springer Nature (2013).
Brydon, E., "CSHL neuroscientists show 'jumping genes' may contribute to aging-related brain defects," CSHL Stories and Media, https://www.cshl.edu/cshl-neuroscientists-show-jumping-genes-may-contribute-to-aging-related-brain-defects/ (Apr. 7, 2013).

(56) References Cited

OTHER PUBLICATIONS

Fikes, B. J., "HIV drugs may help Alzheimer's, say study proposing an undiscovered root cause," The San Diego Union-Tribune (Nov. 23, 2018).
Achuthan, V., et al., "Physiological $Mg^{2+}$ Conditions Significantly Alter the Inhibition of HIV-1 and HIV-2 Reverse Transcriptases by Nucleoside and Non-Nucleoside Inhibitors in Vitro," Biochemistry 56(1):33-46, American Chemical Society, United States (Jan. 2017).
Alexandre, F., et al., "Synthesis and Antiviral Evaluation of Carbocyclic Nucleoside Analogs of Nucleoside Reverse Transcriptase Translocation Inhibitor MK-8591 (4'-Ethynyl-2-fluoro-2'-deoxyadenosine)," J. Med. Chem. 61(20):9218-9228, American Chemical Society, United States (Oct. 2018).
Beutner, G., et al., "Follow the Silyl Cation: Insights into the Vorbrüggen Reaction," Org. Process Res. Dev. 23(9):2050-2056, American Chemical Society, United States (Aug. 2019).
Boojamra, C., et al., "Design, synthesis, and anti-HIV activity of 4'-modified carbocyclic nucleoside phosphonate reverse transcriptase inhibitors," Bioorg. Med. Chem. 17(4):1739-1746, Elsevier, Netherlands (Feb. 2009).
Coufal, N., et al., "Ataxia telangiectasia mutated (ATM) modulates long interspersed element-1 (L1) retrotransposition in human neural stem cells," Proc. Natl. Acad. Sci. U.S.A. 108(51):20382-20387, National Academy of Sciences, United States (Dec. 2011).
Cutinho, P., et al., "Design of metronidazole derivatives and flavonoids as potential non-nucleoside reverse transcriptase inhibitors using combined ligand- and structure-based approaches," J. Biomol. Struct. Dyn. 38(6):1626-1648, Taylor & Francis, United Kingdom (Apr. 2020).
Douville, R., et al., "Identification of active loci of a human endogenous retrovirus in neurons of patients with amyotrophic lateral sclerosis," Ann. Neurol. 69(1):141-151, Wiley, United States (Jan. 2011).
Driver, C., and Vogrig, D., "Apparent retardation of aging in Drosophila melanogaster by inhibitors of reverse transcriptase," Ann. N.Y. Acad. Sci. 717:189-197, Wiley-Blackwell, United States (Jun. 1994).
Fukuyama, K., et al., "Synthesis of EFdA via a diastereoselective aldol reaction of a protected 3-keto furanose," Org. Lett. 17(4):828-831, American Chemical Society, United States (Feb. 2017).
Gallagher, W., et al., "A Claisen approach to 4'-Ed4T," Org. Lett. 17(1):14-17, American Chemical Society, United States (Jan. 2015).
Gallagher, W., et al., "Selective opening of nucleoside derived acetals to form highly functionalized vinyl ethers," Tetrahedron Lett. 61(15):151750, Elsevier, Netherlands (Feb. 2020).
Geser, F., et al., "Amyotrophic lateral sclerosis, frontotemporal dementia and beyond: the TDP-43 diseases," J. Neurol. 256(8):1205-1214, Springer Science+Business Media, Germany (Aug. 2009).
Haraguchi, K., et al., "Synthesis of a highly active new anti-HIV agent 2',3'-didehydro-3'-deoxy-4'-ethynylthymidine," Bioorg. Med. Chem. Lett. 13(21):3775-3777, Elsevier, Netherlands (Nov. 2003).
Haraguchi, K., et al., "An alternative method suitable for a large scale synthesis of 4'-ethynyl-2',3'-didehydro-3'-deoxythymidine," Nucleic Acids Symp. Ser. (Oxf). 48:43-44, Oxford University Press, United Kingdom (2004).
Haraguchi, K., et al., "Synthesis and anti-HIV activity of 4'-cyano-2',3'-didehydro-3'-deoxythymidine," Nucleotides Nucleic Acids 23(4):647-654, Taylor & Francis, United Kingdom (2004).
Haraguchi, K., et al., "A new approach to the synthesis of 4'-carbon-substituted nucleosides: development of a highly active anti-HIV agent 2', 3'-didehydro-3'-deoxy-4'-ethynylthymidine," Nucleotides Nucleic Acids 24(5-7):343-347, Taylor & Francis, United Kingdom (Apr. 2005).
Haraguchi, K., et al., "Nucleophilic substitution at the 4'-position of nucleosides: new access to a promising anti-HIV agent 2',3'-didehydro-3'-deoxy-4'-ethynylthymidine," J. Org. Chem. 71(12):4433-4438, American Chemical Society, United States (Jun. 2006).
Haraguchi, K., et al., "An alternative synthetic method for 4'-C-ethynylstavudine by means of nucleophilic substitution of 4'-benzoyloxythymine nucleoside," Nucleotides Nucleic Acids 26(6-7):835-839, Taylor & Francis, United Kingdom (Dec. 2007).
Haraguchi, K., et al., "From the chemistry of epoxy-sugar nucleosides to the discovery of anti-HIV agent 4'-ethynylstavudine-Festinavir," Curr. Pharm. Des. 19(10):1880-1897, Bentham Science Publishers, United Arab Emirates (2013).
Hattori, S., et al., "Potent activity of a nucleoside reverse transcriptase inhibitor, 4'-ethynyl-2-fluoro-2'-deoxyadenosine, against human immunodeficiency virus type 1 infection in a model using human peripheral blood mononuclear cell-transplanted NOD/SCID Janus kinase 3 knockout mice," Antimicrob. Agents Chemother. 53(9):3887-3893, American Society for Microbiology, United States (Sep. 2009).
Huffman, M., et al., "Design of an in vitro biocatalytic cascade for the manufacture of islatravir," Science 368(6488)1255-1259, American Association for the Advancement of Science, United States (Apr. 2020).
Isono, Y., et al., "Synthesis of 1-benzyl-3-(3,5-dimethylbenzyl)uracil derivatives with potential anti-HIV activity," Antivir. Chem. Chemother. 22(2):57-65, International Medical Press, United Kingdom (Oct. 2011).
Jeong, B., et al., "The prevalence of human endogenous retroviruses in cerebrospinal fluids from patients with sporadic Creutzfeldt-Jakob disease," J. Clin. Virol. 47(2):136-142, Elsevier, Netherlands (Feb. 2010).
Joshi, P., et al., "Inhibition of Heat Shock Protein 90 Prevents HIV Rebound," J. Biol. Chem. 291(19):10332-10346, American Society for Biochemistry and Molecular Biology, United States (May 2016).
Kageyama, M., et al., "Concise synthesis of the anti-HIV nucleoside EFdA," Biosci. Biotechnol. Biochem. 76(6):1219-1225, Japan Society for Bioscience, Biotechnology, and Agrochemistry, Japan (Jun. 2012).
Kageyama, M., et al., "Enantioselective total synthesis of the potent anti-HIV nucleoside EFdA," Org. Lett. 13(19)-5264-5266, American Chemical Society, United States (Oct. 2011).
Kamata, M., et al., "Synthesis of nucleotide analogues, EFdA, EdA and EdAP, and the effect of EdAP on hepatitis B virus replication," Biosci. Biotechnol. Biochem. 84(2):217-227, Japan Society for Bioscience, Biotechnology, and Agrochemistry, Japan (Feb. 2020).
Kawamoto, A., et al., "2'-deoxy-4'-C-ethynyl-2-halo-adenosines active against drug-resistant human immunodeficiency virus type 1 variants," Int. J. Biochem. Cell Biol. 40(11):2410-2420, Elsevier, Netherlands (Apr. 2008).
Kirby, K., et al., "Effects of substitutions at the 4' and 2 positions on the bioactivity of 4'-ethynyl-2-fluoro-2'-deoxyadenosine," Antimicrob. Agents Chemother. 57(12):6254-6264, American Society for Microbiology, United States (Dec. 2013).
Kirby, K., et al., "The sugar ring conformation of 4'-ethynyl-2-fluoro-2'-deoxyadenosine and its recognition by the polymerase active site of HIV reverse transcriptase," Cell. Mol. Biol. 57(1):40-46, American Society for Microbiology, United States (Feb. 2011).
Kovarova, M., et al., "HIV pre-exposure prophylaxis for women and infants prevents vaginal and oral HIV transmission in a preclinical model of HIV infection," J. Antimicrob. Chemother. 71(11):3185-3194, Oxford University Press, United Kingdom (Nov. 2016).
Kubota, Y., et al., "Synthesis and anti-HIV-1 evaluation of phosphonates which mimic the 5'-monophosphate of 4'-branched 2',3'-didehydro-2',3'-dideoxy nucleosides," Bioorg. Med. Chem. 18(20):7186-7192, Elsevier, Netherlands (Oct. 2010).
Kumamoto, H., et al., "Synthesis of carbocyclic analogues of 4'-ethynyl- and 4'-cyano-d4T," Nucleic Acids Symp. Ser. (Oxf). (48):41-42, Oxford University Press, United Kingdom (2004).
Kumamoto, H., et al., "Synthesis of (+/−)-4'-ethynyl and 4'-cyano carbocyclic analogues of stavudine (d4T)," Nucleosides Nucleotides Nucleic Acids, 24(2):73-83, Taylor & Francis, United Kingdom (2005).
Kumamoto, H., et al., "Synthesis and anti-human immunodeficiency virus activity of 4'-branched (+/−)-4'-thiostavudines," J. Med. Chem. 49(26):7861-7867, American Chemical Society, United States (Dec. 2006).

(56) References Cited

OTHER PUBLICATIONS

Kumamoto, H., et al., "Synthesis and antiviral evaluation of (+/−)-4'-ethyny1-5'-difluorocarbocyclic-d4T analogue," Nucleic Acids Symp. Ser. (Oxf). (52):609-610, Oxford University Press, United Kingdom (2008).
Kumamoto, H., et al., "Synthesis of (+)-4'-ethynyl-5',5'-difluoro-2',3'-dehydro-3'-deoxy-carbocyclic thymidine: a difluoromethylidene analogue of promising anti-HIV agent Ed4T," Tetrahedron Lett. 65(36):7630-7636, Elsevier, Netherlands (Sep. 2009).
Mackenzie, I., and Rademakers, R., "The role of transactive response DNA-binding protein-43 in amyotrophic lateral sclerosis and frontotemporal dementia," Curr. Opin. Neurol. 21(6):693-700, Lippincott Williams & Wilkins, United States (Dec. 2008).
Maddaford, A., et al., "Stereoselective Synthesis of rac-4'-Ethynyl-2'-deoxy- and 4'-Ethynyl-2',3'-dideoxy-2',3'-didehydronucleoside Analogues," Synthesis 9:1378-1384, Georg Thieme Verlag Stuttgart, Germany (2007).
Maidji, E., et al., "Cellular HIV Reservoirs and Viral Rebound from the Lymphoid Compartments of 4'-Ethynyl-2-Fluoro-2'-Deoxyadenosine (EFdA)-Suppressed Humanized Mice," Viruses 11(3):256, MDPI, Switzerland (Mar. 2019).
Markowitz, M., et al., "Once-Weekly Oral Dosing of MK-8591 Protects Male Rhesus Macaques From Intrarectal Challenge With SHIV109CP3," J. Infect. Dis. 221(9):1398-1406, Oxford University Press, United Kingdom (Apr. 2020).
Matsuzawa, T., et al., "EFdA, a reverse transcriptase inhibitor, potently blocks HIV-1 ex vivo infection of Langerhans cells within epithelium," J. Invest. Dermatol. 134(4):1158-1161, Elsevier, Netherlands (Apr. 2014).
Mclaughlin, M., et al., "Enantioselective Synthesis of 4'-Ethynyl-2-fluoro-2'-deoxyadenosine (EFdA) via Enzymatic Desymmetrization," Org. Lett. 19(4):926-929, American Chemical Society, United States (Feb. 2017).
Michailidis, E., et al., "4'-Ethynyl-2-fluoro-2'-deoxyadenosine (EFdA) inhibits HIV-1 reverse transcriptase with multiple mechanisms," J. Biol. Chem. 289(35):24533-48, American Society for Biochemistry and Molecular Biology, United States (Aug. 2014).
Michailidis, E., et al., "Hypersusceptibility mechanism of Tenofovir-resistant HIV to EFdA," Retrovirology 10:65, BioMed Central Ltd., United Kingdom (Jun. 2013).
Michailidis, E., et al., "Mechanism of inhibition of HIV-1 reverse transcriptase by 4'-Ethynyl-2-fluoro-2'-deoxyadenosine triphosphate, a translocation-defective reverse transcriptase inhibitor," J. Biol. Chem. 284(51)35681-35691, American Society for Biochemistry and Molecular Biology, United States (Dec. 2009).
Muftuoglu, Y., et al., "Probing the molecular mechanism of action of the HIV-1 reverse transcriptase inhibitor 40-ethynyl-2-fluoro-2'-deoxyadenosine (EFdA) using pre-steady-state kinetics," Antiviral Res. 106:1-4, Elsevier, Netherlands (Jun. 2014).
Muotri, A., et al., "L1 retrotransposition in neurons is modulated by MeCP2," Nature 468(7322):443-446, Nature Publishing Group, United Kingdom (Nov. 2010).
Murphey-Corb, M., et al., "Response of simian immunodeficiency virus to the novel nucleoside reverse transcriptase inhibitor 4'-ethynyl-2-fluoro-2'-deoxyadenosine in vitro and in vivo," Antimicrob. Agents Chemother. 56(9):4707-4712, American Society for Microbiology, United States (Sep. 2012).
Nakata, H., et al., "Activity against human immunodeficiency virus type 1, intracellular metabolism, and effects on human DNA polymerases of 4'-ethynyl-2-fluoro-2'-deoxyadenosine," Antimicrob. Agents Chemother. 51(8):2701-2708, American Society for Microbiology, United States (Aug. 2007).
Nawrat, C. C., et al., "Nine-Step Stereoselective Synthesis of Islatravir from Deoxyribose," Org. Lett. 22(6):2167-2172, American Chemical Society, United States (Mar. 2020).
Ni, G., et al., "Review of α-nucleosides: from discovery, synthesis to properties and potential applications," RSC Adv. 9(25):14302-14320, Royal Society of Chemistry, United Kingdom (May 2019).
Nomura, M., et al., "Nucleosides and nucleotides. 185. Synthesis and biological activities of 4'alpha-C-branched-chain sugar pyrimidine nucleosides," J. Med. Chem. 42(15):2901-2908, American Chemical Society, United States (Jul. 1999).
Ohrui, H., et al., "2'-deoxy-4'-C-ethynyl-2-fluoroadenosine: a nucleoside reverse transcriptase inhibitor with highly potent activity against wide spectrum of HIV-1 strains, favorable toxic profiles, and stability in plasma," Nucleosides Nucleotides Nucleic Acids 26(10-12):1543-1546, Taylor & Francis, United Kingdom (2007).
Ohrui, H., "Chapter 16: 4'-C-Ethynyl-2'-Deoxynucleosides," in Biochemistry, Biotechnology, and Medicine, Herdewijn, P., ed., pp. 425-431, Wiley-VCH, Germany (2008).
Ohrui, H., "A Proposal of the Structure of Modified Nucleosides Expected to be Highly Anti-Viral Active and Lowly Toxic," Nucleic Acids Symp. Ser. (Oxf) 52:631-632, Oxford University Press, United Kingdom (2008).
Ohrui, H., "Creation of Low Toxic Reverse-transcriptase Inhibitory Nucleosides that Prevent the Emergence of Drug-resistant HIV Variants," J. Syn. Org. Chem. Jpn. 64(7):716-723, J-STAGE, Japan (2006).
Ohrui, H., "Development of modified nucleosides that have supremely high anti-HIV activity and low toxicity and prevent the emergence of resistant HIV mutants," Proc. Jpn. Acad. Ser. B. Phys. Biol. Sci. 87(3):53-65, Japan Academy, Japan (2011).
Oliveira, M., et al., "M184I/V substitutions and E138K/M184I/V double substitutions in HIV reverse transcriptase do not significantly affect the antiviral activity of EFdA," J. Antimicrob. Chemother. 72(11):3008-3011, Oxford University Press, United Kingdom (Nov. 2017).
O'Reilly, E., and Ryan, J., "Biocatalytic cascades go viral: An investigational drug targeting the HIV virus is synthesized with nine enzymes," Biocatalysis 336(6470):1199-1200, American Association for the Advancement of Science, United States (Dec. 2019).
Ortiz, A., et al., "Scalable Synthesis of the Potent HIV Inhibitor BMS-986001 by Non-Enzymatic Dynamic Kinetic Asymmetric Transformation (DYKAT)," Angew. Chem. Int. Ed. Engl. 54(24):7185-7188, Wiley-VCH, Germany (Jun. 2015).
Paintsil, E., et al., "Intracellular metabolism and persistence of the anti-human immunodeficiency virus activity of 2',3'-didehydro-3'-deoxy-4'-ethynylthymidine, a novel thymidine analog," Antimicrob. Agents Chemother. 51(11):3870-3879, American Society for Microbiology, United States (Nov. 2007).
Parang, K., et al., "Comparative Antiviral Activity of Remdesivir and Anti-HIV Nucleoside Analogs Against Human Coronavirus 229E (HCoV-229E)," Molecules 25(10):2343, MDPI, Switzerland (May 2020).
Patel, N., et al., "Synthesis of Islatravir Enabled by a Catalytic, Enantioselective Alkynylation of a Ketone," Org. Lett. 22(12):4659-4664, American Chemical Society, United States (Jun. 2020).
Rai, M., et al., "Emerging reverse transcriptase inhibitors for HIV-1 infection," Expert Opin. Emerg. Drugs 23(2):149-157, Informa, United Kingdom (Jun. 2018).
Rana, A., et al., "Advances in Long-Acting Agents for the Treatment of HIV Infection," Drugs 80(6):535-545, Springer Nature, Germany (Apr. 2020).
Salie, Z. L., et al., "Structural basis of HIV inhibition by translocation-defective RT inhibitor 4'-ethynyl-2-fluoro-2'-deoxyadenosine (EFdA)," Proc. Natl. Acad. Sci. U.S.A. 113(33):9274-9279, National Academy of Sciences, United States (Aug. 2016).
Sohl, C., et al., "Mechanism of interaction of human mitochondrial DNA polymerase γ with the novel nucleoside reverse transcriptase inhibitor 4'-ethynyl-2-fluoro-2'-deoxyadenosine indicates a low potential for host toxicity," Antimicrob. Agents Chemother. 56(3):1630-1634, American Society for Microbiology, United States (Mar. 2012).
Takamatsu, Y., et al., "4'-modified nucleoside analogs: potent inhibitors active against entecavir-resistant hepatitis B virus," Hepatology 62(4):1024-1036, Wiley, United States (Oct. 2015).
Takamatsu, Y., et al., "The High Genetic Barrier of EFdA/MK-8591 Stems from Strong Interactions with the Active Site of Drug-Resistant HIV-1 Reverse Transcriptase," Cell Chem. Biol. 25(10):1268-1278, Cell Press, United States (Oct. 2018).

(56) References Cited

OTHER PUBLICATIONS

Takeuchi, T., et al., "Design, Synthesis, and Biological Evaluation of EdAP, a 4'-Ethynyl-2'-Deoxyadenosine 5'-Monophosphate Analog, as a Potent Influenza a Inhibitor," Molecules 24(14):2603, MDPI, Switzerland (Jul. 2019).
Tan, H., et al., "Retrotransposon activation contributes to fragile X premutation rCGG-mediated neurodegeneration," Hum. Mol. Genet. 21(1):57-65, Oxford University Press, United Kingdom (Jan. 2012).
Tanaka, H., et al., "4'-Ethynylstavudine (4'-Ed4T) has potent anti-HIV-1 activity with reduced toxicity and shows a unique activity profile against drug-resistant mutants," Antivir. Chem. Chemother. 16(4):217-221, International Medical Press, United Kingdom (2005).
Tanaka, H., et al., "Synthetic use of epoxy-sugar nucleosides," Nucleosides Nucleotides Nucleic Acids 26(6-7):547-554, Taylor & Francis, United Kingdom (2007).
Wu, V., et al., "MK-8591 (4'-Ethynyl-2-Fluoro-2'-Deoxyadenosine) Exhibits Potent Activity against HIV-2 Isolates and Drug-Resistant HIV-2 Mutants in Culture," Antimicrob. Agents Chemother. 61(8):e00744-00717, American Society for Microbiology, United States (Jul. 2017).
Yang, G., et al., "Impact of novel human immunodeficiency virus type 1 reverse transcriptase mutations P119S and T165A on 4'-ethynylthymidine analog resistance profile," Antimicrob. Agents Chemother. 53(11):4640-4646, American Society for Microbiology, United States (Nov. 2009).
Yasutake, Y., et al., "Structural features in common of HBV and HIV-1 resistance against chirally-distinct nucleoside analogues entecavir and lamivudine," Sci. Rep. 10(1):3021, Nature Portfolio, Germany (Feb. 2020).
Zhang, W., et al., "Development of a vaginal delivery film containing EFdA, a novel anti-HIV nucleoside reverse transcriptase inhibitor," Int. J. Pharm. 461(1-2):203-213, Elsevier, Netherlands (Jan. 2014).
Zhang, W., et al., "In vitro transport characteristics of EFdA, a novel nucleoside reverse transcriptase inhibitor using Caco-2 and MDCKII cell monolayers," Eur. J. Pharmacol. 732:86-95, Elsevier, Netherlands (Jun. 2014).
Zhang, W., et al., "Preformulation studies of EFdA, a novel nucleoside reverse transcriptase inhibitor for HIV prevention," Drug Dev. Ind. Pharm. 40(8):1101-1111, Marcel Dekker, United States (Aug. 2014).
Zhang, W., et al., "Vaginal Microbicide Film Combinations of Two Reverse Transcriptase Inhibitors, EFdA and CSIC, for the Prevention of HIV-1 Sexual Transmission," Pharm. Res. 32(9):2960-2972, Springer Science+Business Media, Germany (Sep. 2015).
Asahchop, E., et al., "Antiviral Drug Resistance and the Need for Development of New HIV-1 Reverse Transcriptase Inhibitors," Antimicrobial Agents and Chemotherapy 56(10):5000-5008, American Society for Microbiology, United States (2012).
Kinney, J.W., et al., "Inflammation as a central mechanism in Alzheimer's disease," Alzheimer's & Dementia: Translational Research & Clinical Interventions 4(1):575-590, Alzheimer's Association, United States (2018).
Akiyama, H., "Inflammation and Alzheimer's disease," Neurobiology of Aging 21(3):383-421, Elsevier, The Netherlands (2000).
Griffin, W.S.T., et al., "Inflammation and neurodegenerative diseases," Am J Clin Nutr 83(suppl):470S-474S, American Society for Nutrition, United States (2006).
Markowitz, M., et al., "EFdA (4'-ethynyl-2-fluoro-2'-deoxyadenosine, MK-8591): A Novel HIV-1 Reverse Transcriptase Translocation Inhibitor," Curr Opin Hiv Aids 13(4):294-299, Wolters Kluwer Health, Inc., United States (2018).
International Search Report and Written Opinion of the International Searching Authority for International Application No. PCT/US2021/051718, United States Patent and Trademark Office, Virginia, United States, mailed Jan. 27, 2022, 15 pages.
International Search Report and Written Opinion of the International Searching Authority for International Application No. PCT/US2021/051716, United States Patent and Trademark Office, Virginia, United States, mailed Feb. 23, 2022, 18 pages.
PUBCHEM, Substance Record for SID 322226924, Available Date: Jan. 24, 2017 [retrieved on Nov. 30, 2021]. Retrieved from the Internet: URL:https://pubchem.ncbi.nlm.nih.gov/substancfe/322226924, 7 pages.
Pizarro, J.G., et al., "Post-Transcriptional Control of LINE-1 Retrotransposition by Cellular Host Factors in Somatic Cells," Front. Cell Dev. Biol. 4(14): 1-19 (Mar. 2016).
Beck, C., et al., "LINE-1 Elements in Structural Variation and Disease," Annu Rev Genomics Hum Genet. 12:187-215 (2011).
Kull, F.C., et al., "Mixtures of Quaternary Ammonium Compounds and Long-chain Fatty Acids as Antifungal Agents," Appl Microbiol 9(6):538-541 (Nov. 1961).
Duraes, F., et al., "Old Drugs as New Treatments for Neurodegenerative Diseases," Pharmaceuticals 11(44): 1-21 (May 2018).
De Cecco, M., et al., "LINE-1 derepression in senescent cells triggers interferon and inflammaging," Nature 566(7742):73-78 (Feb. 2019).
Franceschi, C., et al., "The Continuum of Aging and Age-Related Diseases: Common Mechanisms but Different Rates," Front. Med. 5(61):1-23 (Mar. 2018).
Banuelos-Sanchez, G., et al., "Synthesis and Characterization of Specific Reverse Transcriptase Inhibitors for Mammalian LINE-1 Retrotransposons," Cell Chemical Biology 26:1095-1109 (Aug. 2019).
Higashi-Kuwata, N., et al., "Identification of a novel long-acting 4'-modified nucleoside reverse transcriptase inhibitor against HBV," Journal of Hepatology 74:1075-1086 (2021).
Jones, B., et al., "Nucleoside Analogue Reverse Transcriptase Inhibitors Differentially Inhibit Human LINE-1 Retrotransposition," PLoS One 3(2): e1547 pp. 1-5 (Feb. 2008).
Kopera, H., et al., "LINE-1 Cultured Cell Retrotransposition Assay," Methods Mol Biol. 1400:139-156 (2016).
Dugger, B., et al., "Pathology of Neurodegenerative Diseases," Cold Spring Harb Perspect Biol 9: a028035, 22 pages, Cold Spring Harbor Laboratory Press, United States (2016).
Wang, L., et al., "Human autoimmune diseases: a comprehensive update," Journal of Internal Medicine 278:369-395 (2015).
Mohandas, E., et al., "Frontotemporal dementia: An updated overview," Indian J Psychiatry 51(Suppl1):S65-S69 (Jan. 2009).
Ohrui; H., et al. "Syntheses of 4'-C-Ethynyl-β-d-arabino- and 4'-C-Ethynyl-2'-deoxy-β-d-ribo-pentofuranosylpyrimidines and -purines and Evaluation of Their Anti-HIV Activity," J. Med. Chem. 43(23):4516-4525 (Oct. 2000).
Bollati, V., et al., "DNA methylation in repetitive elements and Alzheimer disease," Brain Behav Immun 25(6):1078-1083, Elsevier, Netherlands (Aug. 2011).
Esposito, F., et al., "HIV-1 Reverse Transcriptase Still Remains a New Drug Target: Structure, Function, Classical Inhibitors, and New Inhibitors with Innovative Mechanisms of Actions," Mol Biol Int 2012:586401, Hindawi, United Kingdom (Jun. 2012).
Iijima, K., et al., "Viral protein R of human immunodeficiency virus type-1 induces retrotransposition of long interspersed element-1," Retrovirology 10:83, BioMed Central, United Kingdom (Aug. 2013).
Kharkevich, D.A., "Doses and Concentrations" in *Pharmacology,* 10th Ed., pp. 73-74, GEOTAR-Media, Moscow, Russia (2010).
Savage, A.L., et al., "Retrotransposons in the development and progression of amyotrophic lateral sclerosis," J Neurol Neurosurg Psychiatry 90(3):284-293, BMJ, United Kingdom (Mar. 2019).
English language translation of Office Action for Russian Patent Application No. 2021119040/04(040073), 10 pages.
Department of Laboratory Medicine, "Study on long-term complications in HIV-infected patients [online]," Tokyo Medical University, dated Aug. 17, 2014, accessed at https://hospinfo.tokyo-med.ac.jp/shinryo/rinsho/data/info_20140827_1.pdf, accessed on Sep. 25, 2025, 2 pages.
Matsuda, J., "Autoimmune Phenomena in Individuals with HIV-infection—Coincided- or Epi-phenomena?" The Journal of AIDS Research 4(3):108-115, The Japanese Society for AIDS Research, Japan (Aug. 2002).

(56) References Cited

OTHER PUBLICATIONS

Tateyama, M., and Kami, K., "Current understanding of HIV-associated neurocognitive disorder," Japanese Journal of Chemotherapy 68(1):108-115, The Japanese Society of Chemotherapy, Japan (Jan. 2020).

English language translation of Office Action for Japanese Patent Application No. 2023-542839, issued on Oct. 2, 2025, Japan Patent Office, Japan, 7 pages.

Zaki-Dizaji, M., et al., "Inflammation, a significant player of Ataxia-Telangiectasia pathogenesis?," Inflammation Research 67(7):559-570, Springer, Switzerland (Jul. 2018).

Greicius, M.D., et al., "Presenile dementia syndromes: an update on taxonomy and diagnosis," Journal of Neurology, Neurosurgery, and Psychiatry 72(6):691-700, BMJ Publishing Group, United Kingdom (Jun. 2002).

D'Ordine, A.M., et al., "Identification and characterization of small molecule inhibitors of the LINE-1 retrotransposon endonuclease," bioRxiv, 16 pages, Cold Spring Harbor Laboratory, United States (Dec. 29, 2022).

Carlini, F., et al., "The reverse transcription inhibitor abacavir shows anticancer activity in prostate cancer cell lines," PLoS One 50(12):e14221, pp. 1-13, Public Library of Science, United States (Dec. 2010).

Sciamanna, I., et al., "LINE-1-encoded reverse Transcriptase as a target in cancer therapy," Frontiers in Bioscience (Landmark Edition) 23(7):1360-1369, IMR Press, Singapore (Mar. 2018).

Jin, J., et al., "Combination therapy versus gemcitabine monotherapy in the treatment of elderly pancreatic cancer: a meta-analysis of randomized controlled trials," Drug Design, Development and Therapy 12:475-480, Dove Press Limited, New Zealand (Mar. 2018).

NCT03144804, "A Phase 2 Study of Lamivudine in Patients With p53 Mutant Metastatic Colorectal Cancer," Clinical Trial Study Protocol, Protocol Version Date: Nov. 14, 2019, accessed at https://cdn.clinicaltrials.gov/large-docs/04/NCT03144804/Prot_SAP_000.pdf, 53 pages.

Lanz, C., et al., "The importance of antiandrogen in prostate cancer treatment," Annals of Translational Medicine 7(Suppl 8):S362, pp. 1-7, AME Publishing Company, China (Dec. 2019).

Ene, L., et al., "How much do antiretroviral drugs penetrate into the central nervous system?" Journal of Medicine and Life 4(4):432-439, Carol Davila University Press, Romania (Nov. 2011).

Moran, J.V., et al., "High frequency retrotransposition in cultured mammalian cells," Cell 87(5):917-927, Cell Press, United States (Nov. 1996).

Osborne, O., et al., "The Paradox of HIV Blood-Brain Barrier Penetrance and Antiretroviral Drug Delivery Deficiencies," Trends in Neurosciences 43(9):695-708, Elsevier, United Kingdom (Sep. 2020).

Smith, R.A., et al., "The Nucleoside Analog BMS-986001 Shows Greater In Vitro Activity against HIV-2 than against HIV-1," Antimicrobial Agents and Chemotherapy 59(12):7437-7446, American Society for Microbiology, United States (Dec. 2015).

Transposon Therapeutics, "Results from a Phase 2 Study of its LINE-1 Reverse Transcriptase Inhibitor TPN-101 for the Treatment of PSP and Interim Results from a Phase 2 Study of TPN-101 for the Treatment of C9orf72-Related ALS and/or FTD," BioSpace, accessed at https://www.biospace.com/transposon-announces-final-results-from-a-phase-2-study-of-its-line-1-reverse-transcriptase-inhibitor-tpn-101-for-the-treatment-of-psp-and-interim-results-from-a-phase-2-study-of-tpn-101-for-the-treatment-of-c9orf72-related-als-and-or-ftd, 13 pages (Feb. 13, 2024).

* cited by examiner

LINE-1 INHIBITORS TO TREAT DISEASE

BACKGROUND OF THE INVENTION

Field of the Invention

The present disclosure provides methods of treating or preventing a disease, disorder, or condition caused by LINE-1 retrotransposition in a subject in need thereof, the method comprising administering a compound of any one of Formulae I-III, or a pharmaceutical composition thereof, or a tautomer thereof, to the subject.

Background

Long INterspersed Element-1 (LINE-1 or L1) retrotransposons form the only autonomously active family of transposable elements in humans. They are expressed and mobile in the germline, in embryonic stem cells, and in the early embryo, but are silenced in most somatic tissues. LINE-1 plays an important role in individual genome variations through insertional mutagenesis and sequence transduction, which occasionally lead to genetic diseases and disorders. In addition, LINE-1 is reactivated in certain cancers thus contributing to tumor genome dynamics. The LINE-1 element codes for two proteins, ORF1p and ORF2p, which are essential for its mobility. ORF1p is an RNA-binding protein with nucleic acid chaperone activity. ORF2p possesses endonuclease and reverse transcriptase activities. These proteins and the LINE-1 RNA assemble into a ribonucleoprotein particle (LINE-1 RNP)—the core of the retrotransposition machinery. The LINE-1 RNP mediates the synthesis of new LINE-1 copies upon cleavage of the target DNA and reverse transcription of the LINE-1 RNA at the target site. The LINE-1 element takes benefit of cellular host factors to complete its life cycle, however several cellular pathways also limit the cellular accumulation of LINE-1 RNPs and their deleterious activities. See, e.g., Pizarro and Cristofari (2016) *Front. Cell Dev. Biol.* 4:14. doi: 10.3389/fcell.2016.00014. There exists a need for methods to treat or prevent diseases, disorders, or conditions caused by LINE-1 retrotransposition in subjects.

BRIEF SUMMARY OF THE INVENTION

In one aspect, the present disclosure provides methods of treating or preventing a disease, disorder, or condition caused by a pathophysiological retrotransposon-associated process in a subject in need thereof, the method comprising administering to the subject a therapeutically effective amount of a compound of any one of Formula I-III, or a pharmaceutically acceptable salt or solvate thereof, or a tautomer thereof, a compound of Table 1A, or a pharmaceutically acceptable salt or solvate thereof, or a tautomer thereof, or a compound of Table 1B, or a pharmaceutically acceptable salt or solvate thereof, or a tautomer thereof, collectively referred to as "Compounds of the Disclosure," see below. Exemplary diseases, disorders, or conditions include, but are not limited, to neurodegenerative diseases, autoimmune diseases, and age-associated diseases.

In another aspect, the present disclosure provides methods of treating or preventing a symptom of a disease, disorder, or condition caused by a pathophysiological retrotransposon-associated process in a subject in need thereof, the method comprising administering to the subject a therapeutically effective amount of a Compound of the Disclosure, or a pharmaceutical composition thereof.

In another aspect, the present disclosure provides methods of inhibiting a LINE-1 retrotransposition event, e.g., a somatic LINE-1 insertion, that causes a disease, disorder, or condition, in a subject in need thereof, the method comprising administering to the subject a therapeutically effective amount of a Compound of the Disclosure to the subject, or a pharmaceutical composition thereof.

In another aspect, the present disclosure provides methods of treating a disease, condition, or disorder in a subject in need thereof, the method comprising (a) determining whether an overexpression of a biomarker, e.g., retrotransposon RNA, retrotransposon reverse transcriptase, or retrotransposon DNA, e.g., LINE-1 RNA, ORF1p, or ORF2p, is present or absent in a biological sample taken from the subject; and (b) administering a therapeutically effective amount of a compound of a Compound of the Disclosure, or a pharmaceutical composition thereof, to the subject if an overexpression of the biomarker is present in the biological sample.

In another aspect, the present disclosure provides methods of identifying whether a subject having a disease, condition, or disorder is a candidate for treatment with a Compound of the Disclosure, or a pharmaceutical composition thereof, the method comprising (a) determining whether an overexpression of a biomarker, e.g., retrotransposon RNA, retrotransposon reverse transcriptase, or retrotransposon DNA, e.g., LINE-1 RNA, ORF1p, or ORF2p, is present or absent in a biological sample taken from the subject; and (b) identifying the subject as being a candidate for treatment if an overexpression of the biomarker is present; or (c) identifying the subject as not being a candidate for treatment if an overexpression of the biomarker is absent.

In another aspect, the present disclosure provides methods of predicting treatment outcome in a subject having a disease, condition, or disorder, the method comprising determining whether an overexpression of a biomarker, e.g., retrotransposon RNA, retrotransposon reverse transcriptase, or retrotransposon DNA, e.g., LINE-1 RNA, ORF1p, or ORF2p, is present or absent in a biological sample taken from the subject, wherein (a) the presence of an overexpression of the biomarker in the biological sample indicates that administering a Compound of the Disclosure, or a pharmaceutical composition thereof, to the subject will likely cause a favorable therapeutic response; and (b) the absence of an overexpression of the biomarker in the biological sample indicates that administering a Compound of the Disclosure, or a pharmaceutical composition thereof, to the subject will likely cause an unfavorable therapeutic response.

In another aspect, the present disclosure provides methods, comprising administering a therapeutically effective amount of a Compound of the Disclosure, or a pharmaceutical composition thereof, to a subject in need thereof, wherein (a) the subject has a disease, disorder, or condition; and (b) the disease, disorder, or condition is characterized as having an overexpression of a biomarker, e.g., retrotransposon RNA, retrotransposon reverse transcriptase, or retrotransposon DNA, e.g., LINE-1 RNA, ORF1p, or ORF2p.

In another aspect, the present disclosure provides a kit comprising a Compound of the Disclosure, or a pharmaceutical composition thereof, and instructions for administering the compound or composition to a subject having a disease, condition, or disorder caused by a pathophysiological retrotransposon-associated process.

In another aspect, the present disclosure provides a Compound of the Disclosure, or a pharmaceutical composition thereof, for use in treating or preventing a disease, disorder, or condition caused by a pathophysiological retrotransposon-associated process.

In another aspect, the present disclosure provides a Compound of the Disclosure, or a pharmaceutical composition thereof, for use in treating or preventing a symptom of a disease, disorder, or condition caused by a pathophysiological retrotransposon-associated process In another aspect, the present disclosure provides the use of Compound of the Disclosure, or a pharmaceutical composition thereof, for the manufacture of a medicament for treating or preventing a disease, disorder, or condition caused by a pathophysiological retrotransposon-associated process.

In another aspect, the present disclosure provides the use of Compound of the Disclosure, or a pharmaceutical composition thereof, for the manufacture of a medicament for treating or preventing a symptom of a disease, disorder, or condition caused by a pathophysiological retrotransposon-associated process.

DETAILED DESCRIPTION OF THE INVENTION

I. Compounds of the Disclosure

Applicant has discovered that compounds having any one of Formulae I-III are surprisingly potent LINE-1 inhibitors. As such, these compounds can be used to treat diseases, disorders, or conditions wherein LINE-1 retrotransposition plays a causative role.

In one embodiment, Compounds of the Disclosure are compounds of Formula I:

I

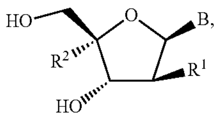

or a pharmaceutically acceptable salt or solvate thereof, or a tautomer thereof, wherein:

B is selected from the group consisting of:

B-1

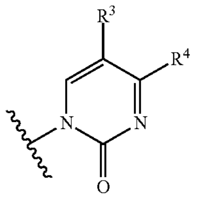

and

B-2

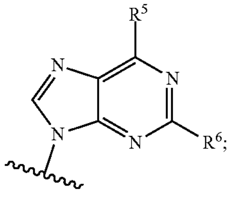

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$.

In another embodiment, Compounds of the Disclosure are compounds of Formula II:

II

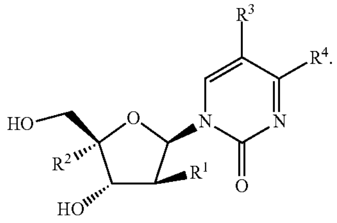

or a pharmaceutically acceptable salt or solvate thereof, or a tautomer thereof, wherein $R^1$, $R^2$, $R^3$, and $R^4$ are as defined in connection with Formula I.

In another embodiment, Compounds of the Disclosure are compounds of Formula II, or a pharmaceutically acceptable salt or solvate thereof, or a tautomer thereof, wherein $R^3$ is hydrogen.

In another embodiment, Compounds of the Disclosure are compounds of Formula II, or a pharmaceutically acceptable salt or solvate thereof, or a tautomer thereof, wherein $R^3$ is methyl.

In another embodiment, Compounds of the Disclosure are compounds of Formula II, or a pharmaceutically acceptable salt or solvate thereof, or a tautomer thereof, wherein $R^4$ is —$NH_2$.

In another embodiment, Compounds of the Disclosure are compounds of Formula III:

III

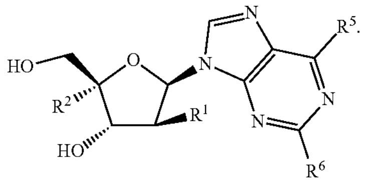

or a pharmaceutically acceptable salt or solvate thereof, or a tautomer thereof, wherein $R^1$, $R^2$, $R^5$, and $R^6$ are as defined in connection with Formula I.

In another embodiment, Compounds of the Disclosure are compounds of Formula III, or a pharmaceutically acceptable salt or solvate thereof, or a tautomer thereof, wherein $R^5$ is —$NH_2$.

In another embodiment, Compounds of the Disclosure are compounds of Formula III, or a pharmaceutically acceptable salt or solvate thereof, or a tautomer thereof, wherein $R^5$ is —OH.

In another embodiment, Compounds of the Disclosure are compounds of Formula III, or a pharmaceutically acceptable salt or solvate thereof, or a tautomer thereof, wherein $R^6$ is hydrogen.

In another embodiment, Compounds of the Disclosure are compounds of Formula III, or a pharmaceutically acceptable salt or solvate thereof, or a tautomer thereof, wherein $R^6$ is chloro.

In another embodiment, Compounds of the Disclosure are compounds of Formula III, or a pharmaceutically acceptable salt or solvate thereof, or a tautomer thereof, wherein $R^6$ is $—NH_2$.

In another embodiment, Compounds of the Disclosure are compounds of any one of Formulae I-III, or a pharmaceutically acceptable salt or solvate thereof, or a tautomer thereof, wherein $R^1$ is hydrogen.

In another embodiment, Compounds of the Disclosure are compounds of any one of Formulae I-III, or a pharmaceutically acceptable salt or solvate thereof, or a tautomer thereof, wherein $R^1$ is —OH.

In another embodiment, Compounds of the Disclosure are compounds of any one of Formulae I-III, or a pharmaceutically acceptable salt or solvate thereof, or a tautomer thereof, wherein $R^2$ is methyl.

In another embodiment, Compounds of the Disclosure are compounds of any one of Formulae I-III, or a pharmaceutically acceptable salt or solvate thereof, or a tautomer thereof, wherein $R^2$ is ethynyl, i.e.,

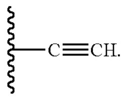 [SMILES: *C#C]

In another embodiment, Compounds of the Disclosure are compounds of any one of Formulae I-III, or a pharmaceutically acceptable salt or solvate thereof, or a tautomer thereof, wherein $R^2$ is —CN.

In another embodiment, Compounds of the Disclosure are compounds of Table 1, or a pharmaceutically acceptable salt or solvate thereof, or a tautomer thereof.

TABLE 1

| Compound Number | Structure |
|---|---|
| 1 | 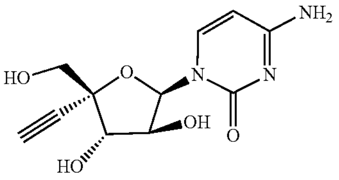 [SMILES: C#C[C@]1(CO)O[C@@H](n2ccc(N)nc2=O)[C@@H](O)[C@@H]1O] |
| 2 | 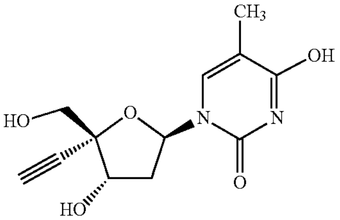 [SMILES: C#C[C@]1(CO)O[C@@H](n2cc(C)c(O)nc2=O)C[C@@H]1O] |

TABLE 1-continued

| Compound Number | Structure |
|---|---|
| 3 | 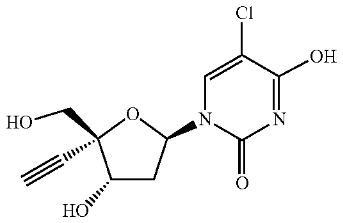 |
| 4 | 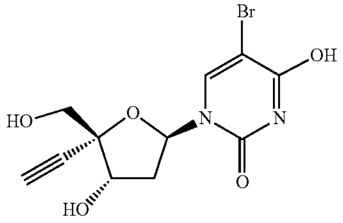 [SMILES: C#C[C@]1(CO)O[C@@H](n2cc(Br)c(O)nc2=O)C[C@@H]1O] |
| 5 | 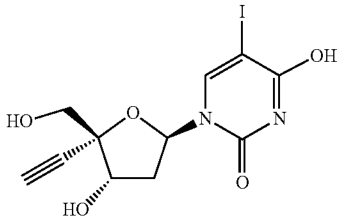 [SMILES: C#C[C@]1(CO)O[C@@H](n2cc(I)c(O)nc2=O)C[C@@H]1O] |
| 6 | 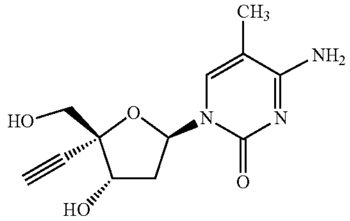 [SMILES: C#C[C@]1(CO)O[C@@H](n2cc(C)c(N)nc2=O)C[C@@H]1O] |
| 7 | 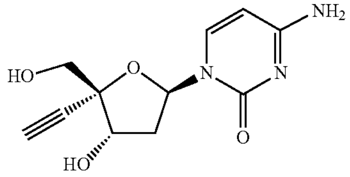 [SMILES: C#C[C@]1(CO)O[C@@H](n2ccc(N)nc2=O)C[C@@H]1O] |
| 8 | 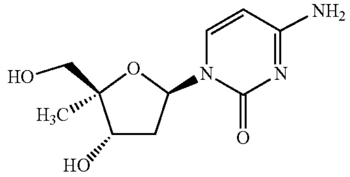 [SMILES: C[C@]1(CO)O[C@@H](n2ccc(N)nc2=O)C[C@@H]1O] |
| 9 | 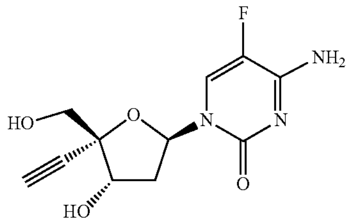 [SMILES: C#C[C@]1(CO)O[C@@H](n2cc(F)c(N)nc2=O)C[C@@H]1O] |

TABLE 1-continued
| Compound Number | Structure |
|---|---|
| 10 | 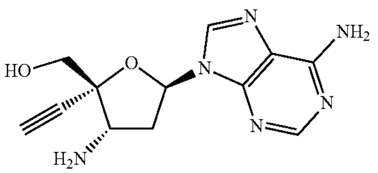 [SMILES: C#C[C@]1(CO)O[C@@H](n2cnc3c(N)ncnc32)C[C@@H]1N] |
| 11 | 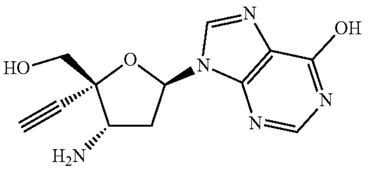 [SMILES: C#C[C@]1(CO)O[C@@H](n2cnc3c(O)ncnc32)C[C@@H]1N] |
| 12 | 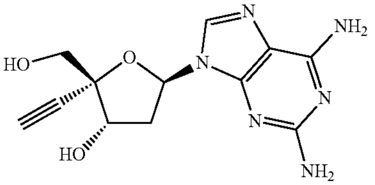 [SMILES: C#C[C@]1(CO)O[C@@H](n2cnc3c(N)nc(N)nc32)C[C@@H]1O] |
| 13 | 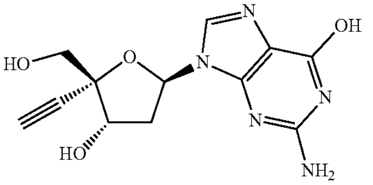 [SMILES: C#C[C@]1(CO)O[C@@H](n2cnc3c(O)nc(N)nc32)C[C@@H]1O] |
| 14 | 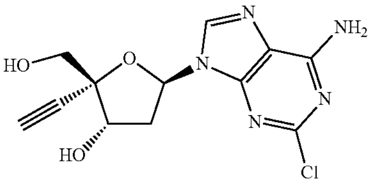 [SMILES: C#C[C@]1(CO)O[C@@H](n2cnc3c(N)nc(Cl)nc32)C[C@@H]1O] |
| 15 | 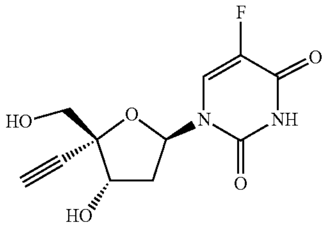 [SMILES: C#C[C@]1(CO)O[C@@H](n2cc(F)c(=O)[nH]c2=O)C[C@@H]1O] |
In another embodiment, Compounds of the Disclosure are compounds of Table 1A, or a pharmaceutically acceptable salt or solvate thereof, or a tautomer thereof.
TABLE 1A
| | |
|---|---|
| 16 | 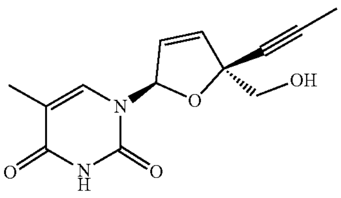 [SMILES: CC#C[C@]1(CO)C=C[C@H](n2cc(C)c(=O)[nH]c2=O)O1] |
TABLE 1A-continued
| | |
|---|---|
| 17 | 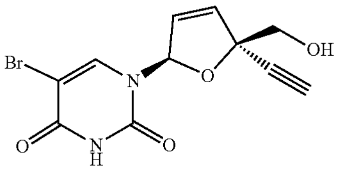 [SMILES: C#C[C@@]1(CO)C=C[C@H](n2cc(Br)c(=O)[nH]c2=O)O1] |
| 18 | 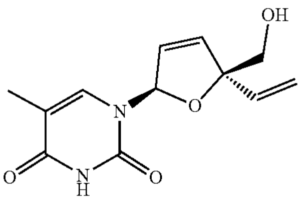 [SMILES: C=C[C@@]1(CO)C=C[C@H](n2cc(C)c(=O)[nH]c2=O)O1] |
| 19 | 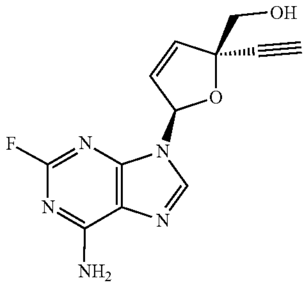 [SMILES: C#C[C@@]1(CO)C=C[C@H](n2cnc3c(N)nc(F)nc32)O1] |
| 20 | 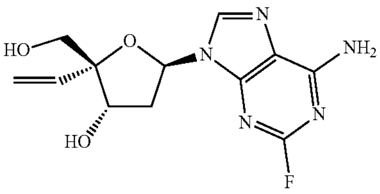 [SMILES: C=C[C@]1(CO)O[C@@H](n2cnc3c(N)nc(F)nc32)C[C@@H]1O] |
| 21 | 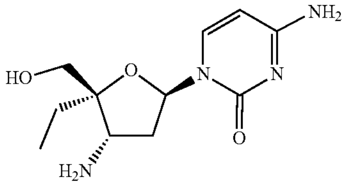 [SMILES: CC[C@]1(CO)O[C@@H](n2ccc(N)nc2=O)C[C@@H]1N] |
| 22 | 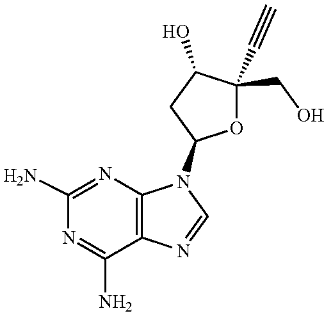 [SMILES: C#C[C@]1(CO)O[C@@H](n2cnc3c(N)nc(N)nc32)C[C@@H]1O] |

TABLE 1A-continued
23
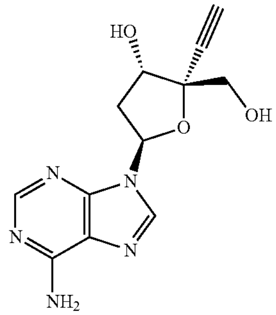 [SMILES: C#C[C@]1(CO)O[C@@H](n2cnc3c(N)ncnc32)C[C@@H]1O]
24
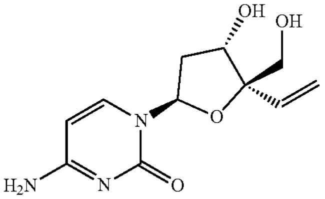 [SMILES: C=C[C@]1(CO)O[C@@H](n2ccc(N)nc2=O)C[C@@H]1O]
25
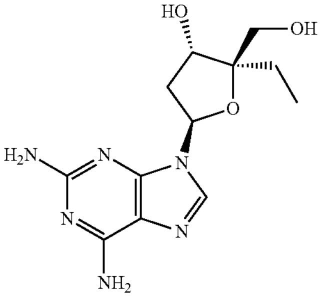 [SMILES: CC[C@]1(CO)O[C@@H](n2cnc3c(N)nc(N)nc32)C[C@@H]1O]
26
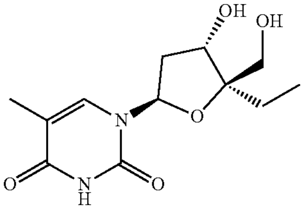 [SMILES: CC[C@]1(CO)O[C@@H](n2cc(C)c(=O)[nH]c2=O)C[C@@H]1O]
27
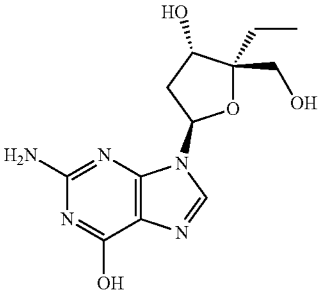 [SMILES: CC[C@]1(CO)O[C@@H](n2cnc3c(O)nc(N)nc32)C[C@@H]1O]
In another embodiment, Compounds of the Disclosure are compounds of Table 1B, or a pharmaceutically acceptable salt or solvate thereof, or a tautomer thereof.
TABLE 1B
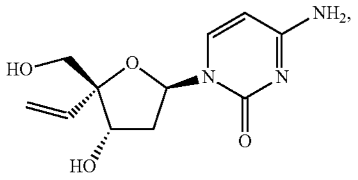 [SMILES: C=C[C@]1(CO)O[C@@H](n2ccc(N)nc2=O)C[C@@H]1O]
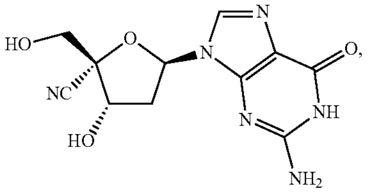 [SMILES: N#C[C@]1(CO)O[C@@H](n2cnc3c(=O)[nH]c(N)nc32)C[C@@H]1O]
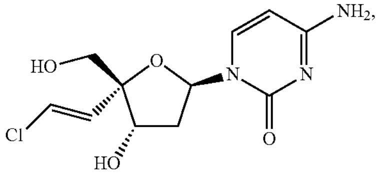 [SMILES: Nc1ccn([C@H]2C[C@H](O)[C@@](/C=C/Cl)(CO)O2)c(=O)n1]
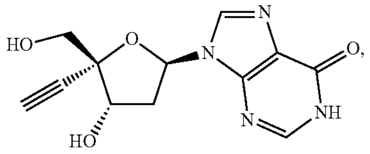 [SMILES: C#C[C@]1(CO)O[C@@H](n2cnc3c(=O)[nH]cnc32)C[C@@H]1O]
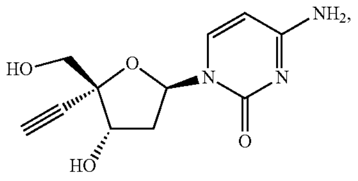 [SMILES: C#C[C@]1(CO)O[C@@H](n2ccc(N)nc2=O)C[C@@H]1O]
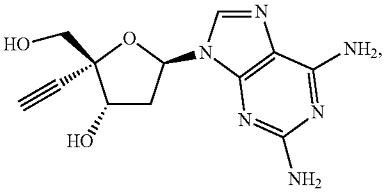 [SMILES: C#C[C@]1(CO)O[C@@H](n2cnc3c(N)nc(N)nc32)C[C@@H]1O]
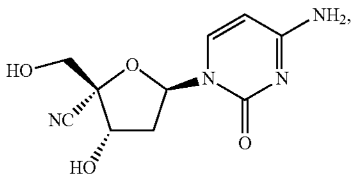 [SMILES: N#C[C@]1(CO)O[C@@H](n2ccc(N)nc2=O)C[C@@H]1O]
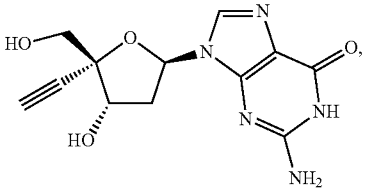 [SMILES: C#C[C@]1(CO)O[C@@H](n2cnc3c(=O)[nH]c(N)nc32)C[C@@H]1O]

TABLE 1B-continued
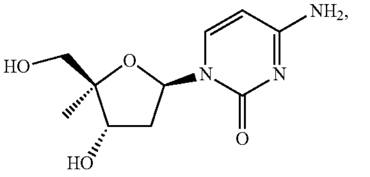 [SMILES: C[C@]1(CO)O[C@@H](n2ccc(N)nc2=O)C[C@@H]1O]
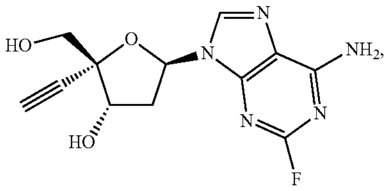 [SMILES: C#C[C@]1(CO)O[C@@H](n2cnc3c(N)nc(F)nc32)C[C@@H]1O]
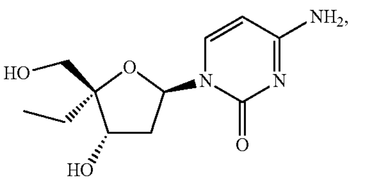 [SMILES: CC[C@]1(CO)O[C@@H](n2ccc(N)nc2=O)C[C@@H]1O]
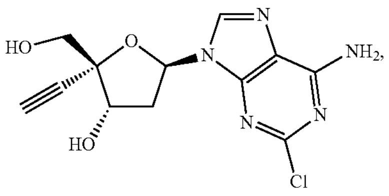 [SMILES: C#C[C@]1(CO)O[C@@H](n2cnc3c(N)nc(Cl)nc32)C[C@@H]1O]
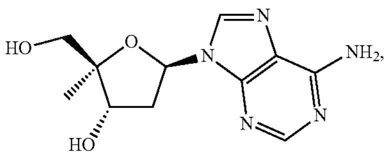 [SMILES: C[C@]1(CO)O[C@@H](n2cnc3c(N)ncnc32)C[C@@H]1O]
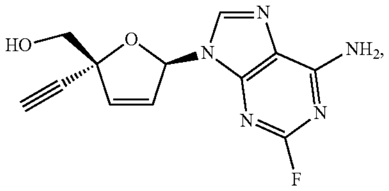 [SMILES: C#C[C@@]1(CO)C=C[C@H](n2cnc3c(N)nc(F)nc32)O1]
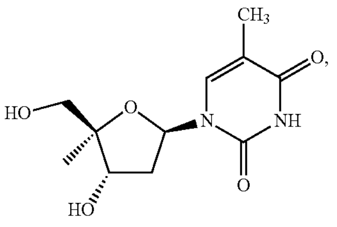 [SMILES: Cc1cn([C@H]2C[C@H](O)[C@@](C)(CO)O2)c(=O)[nH]c1=O]
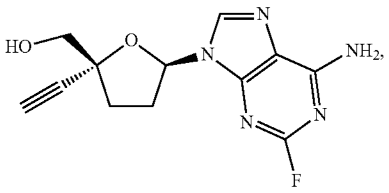 [SMILES: C#C[C@@]1(CO)CC[C@H](n2cnc3c(N)nc(F)nc32)O1]
TABLE 1B-continued
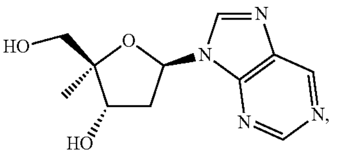 [SMILES: C[C@]1(CO)O[C@@H](n2cnc3cncnc32)C[C@@H]1O]
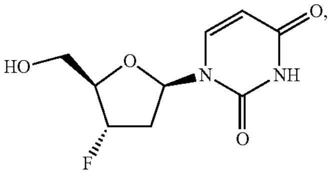 [SMILES: O=c1ccn([C@H]2C[C@H](F)[C@@H](CO)O2)c(=O)[nH]1]
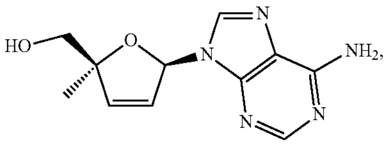 [SMILES: C[C@@]1(CO)C=C[C@H](n2cnc3c(N)ncnc32)O1]
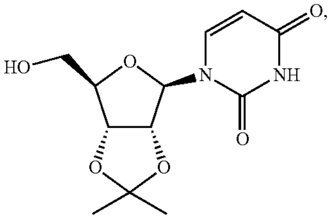 [SMILES: CC1(C)O[C@@H]2[C@H](O1)[C@@H](CO)O[C@H]2n1ccc(=O)[nH]c1=O]
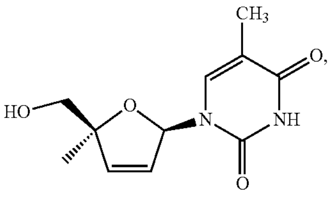 [SMILES: Cc1cn([C@H]2C=C[C@@](C)(CO)O2)c(=O)[nH]c1=O]
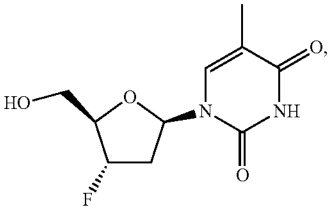 [SMILES: Cc1cn([C@H]2C[C@H](F)[C@@H](CO)O2)c(=O)[nH]c1=O]
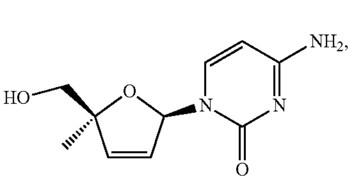 [SMILES: C[C@@]1(CO)C=C[C@H](n2ccc(N)nc2=O)O1]
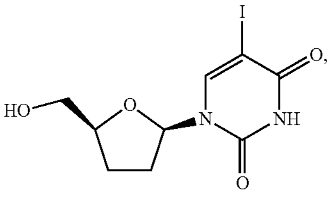 [SMILES: O=c1[nH]c(=O)n([C@H]2CC[C@@H](CO)O2)cc1I]

TABLE 1B-continued
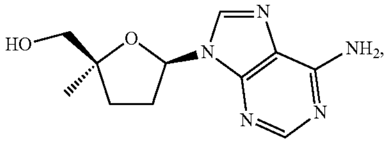 [SMILES: C[C@@]1(CO)CC[C@H](n2cnc3c(N)ncnc32)O1]
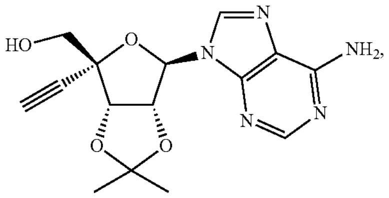 [SMILES: C#C[C@]1(CO)O[C@@H](n2cnc3c(N)ncnc32)[C@@H]2OC(C)(C)O[C@@H]21]
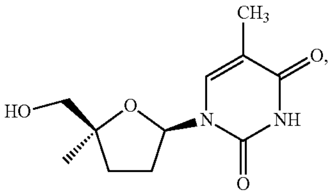 [SMILES: Cc1cn([C@H]2CC[C@@](C)(CO)O2)c(=O)[nH]c1=O]
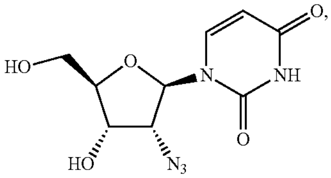 [SMILES: [N-]=[N+]=N[C@@H]1[C@H](O)[C@@H](CO)O[C@H]1n1ccc(=O)[nH]c1=O]
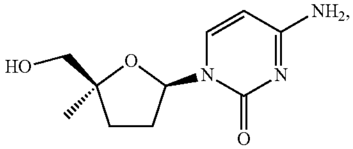 [SMILES: C[C@@]1(CO)CC[C@H](n2ccc(N)nc2=O)O1]
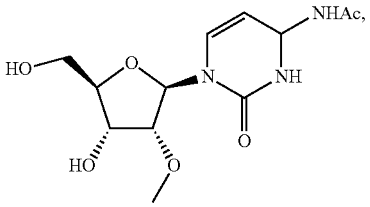 [SMILES: CO[C@@H]1[C@H](O)[C@@H](CO)O[C@H]1N1C=CC(NC(C)=O)NC1=O]
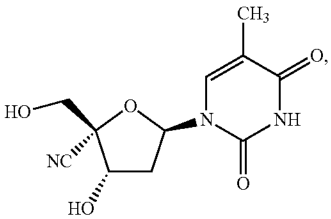 [SMILES: Cc1cn([C@H]2C[C@H](O)[C@@](C#N)(CO)O2)c(=O)[nH]c1=O]
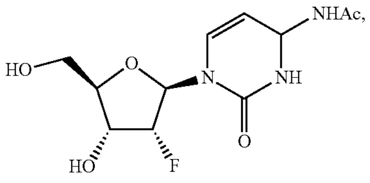 [SMILES: CC(=O)NC1C=CN([C@@H]2O[C@H](CO)[C@@H](O)[C@H]2F)C(=O)N1]
TABLE 1B-continued
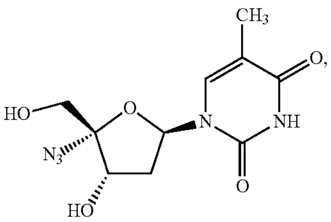 [SMILES: Cc1cn([C@H]2C[C@H](O)[C@](CO)(N=[N+]=[N-])O2)c(=O)[nH]c1=O]
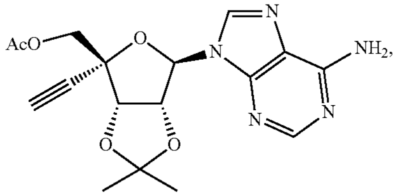 [SMILES: C#C[C@]1(COC(C)=O)O[C@@H](n2cnc3c(N)ncnc32)[C@@H]2OC(C)(C)O[C@@H]21]
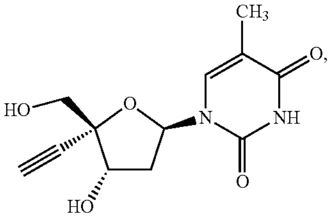 [SMILES: C#C[C@]1(CO)O[C@@H](n2cc(C)c(=O)[nH]c2=O)C[C@@H]1O]
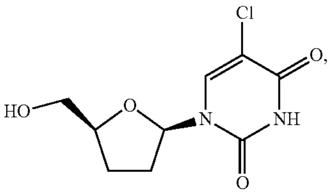 [SMILES: O=c1[nH]c(=O)n([C@H]2CC[C@@H](CO)O2)cc1Cl]
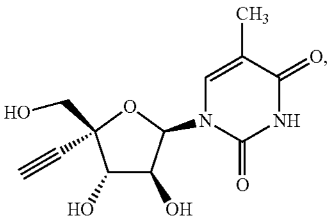 [SMILES: C#C[C@]1(CO)O[C@@H](n2cc(C)c(=O)[nH]c2=O)[C@@H](O)[C@@H]1O]
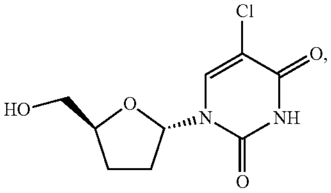 [SMILES: O=c1[nH]c(=O)n([C@@H]2CC[C@@H](CO)O2)cc1Cl]
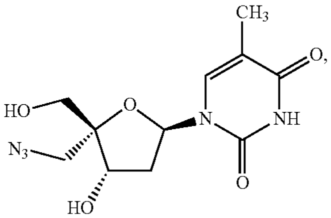 [SMILES: Cc1cn([C@H]2C[C@H](O)[C@](CO)(CN=[N+]=[N-])O2)c(=O)[nH]c1=O]

TABLE 1B-continued
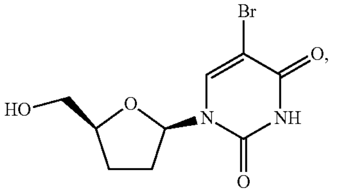 [SMILES: O=c1[nH]c(=O)n([C@H]2CC[C@@H](CO)O2)cc1Br]
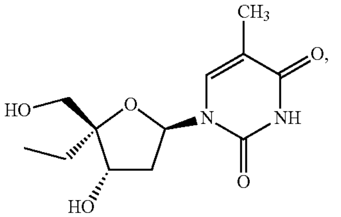 [SMILES: CC[C@]1(CO)O[C@@H](n2cc(C)c(=O)[nH]c2=O)C[C@@H]1O]
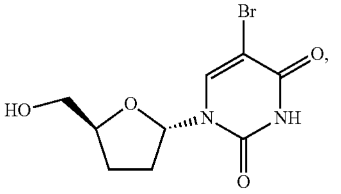
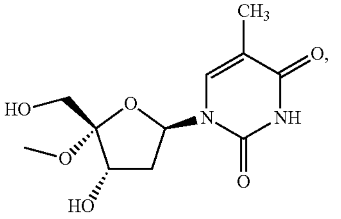 [SMILES: CO[C@]1(CO)O[C@@H](n2cc(C)c(=O)[nH]c2=O)C[C@@H]1O]
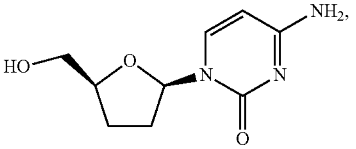 [SMILES: Nc1ccn([C@H]2CC[C@@H](CO)O2)c(=O)n1]
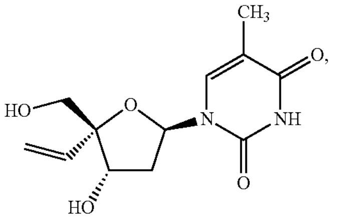 [SMILES: C=C[C@]1(CO)O[C@@H](n2cc(C)c(=O)[nH]c2=O)C[C@@H]1O]
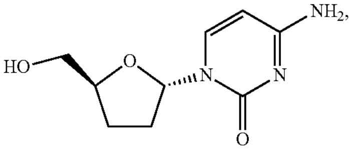 [SMILES: Nc1ccn([C@@H]2CC[C@@H](CO)O2)c(=O)n1]
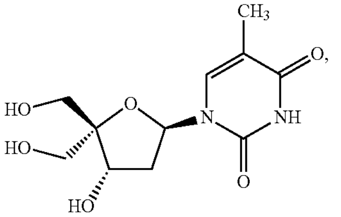
TABLE 1B-continued
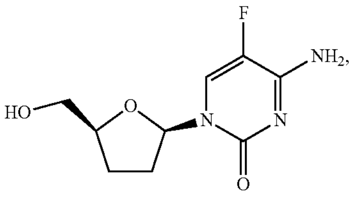 [SMILES: Nc1nc(=O)n([C@H]2CC[C@@H](CO)O2)cc1F]
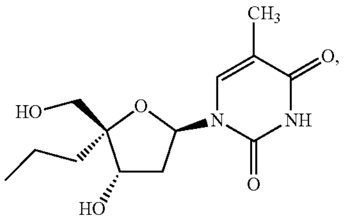 [SMILES: CCC[C@]1(CO)O[C@@H](n2cc(C)c(=O)[nH]c2=O)C[C@@H]1O]
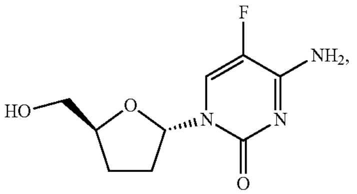 [SMILES: Nc1nc(=O)n([C@@H]2CC[C@@H](CO)O2)cc1F]
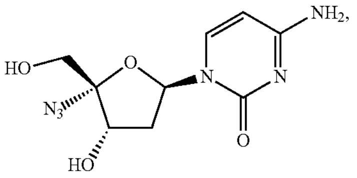 [SMILES: [N-]=[N+]=N[C@]1(CO)O[C@@H](n2ccc(N)nc2=O)C[C@@H]1O]
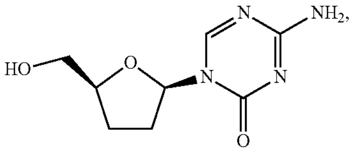 [SMILES: Nc1ncn([C@H]2CC[C@@H](CO)O2)c(=O)n1]
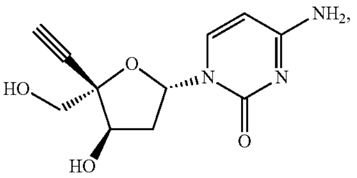 [SMILES: C#C[C@@]1(CO)O[C@H](n2ccc(N)nc2=O)C[C@H]1O]
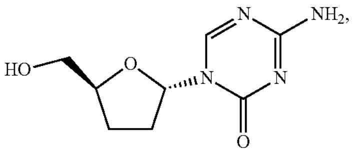 [SMILES: Nc1ncn([C@@H]2CC[C@@H](CO)O2)c(=O)n1]
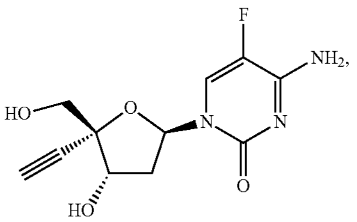 [SMILES: C#C[C@]1(CO)O[C@@H](n2cc(F)c(N)nc2=O)C[C@@H]1O]

TABLE 1B-continued

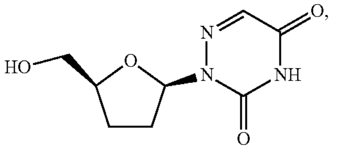 [SMILES: O=c1cnn([C@H]2CC[C@@H](CO)O2)c(=O)[nH]1]

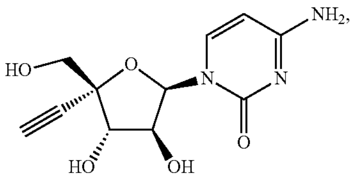 [SMILES: C#C[C@]1(CO)O[C@@H](n2ccc(N)nc2=O)[C@@H](O)[C@@H]1O]

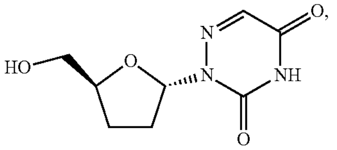 [SMILES: O=c1cnn([C@@H]2CC[C@@H](CO)O2)c(=O)[nH]1]

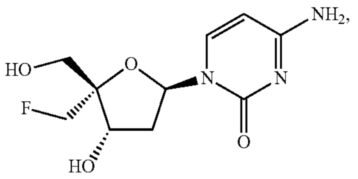 [SMILES: Nc1ccn([C@H]2C[C@H](O)[C@](CO)(CF)O2)c(=O)n1]

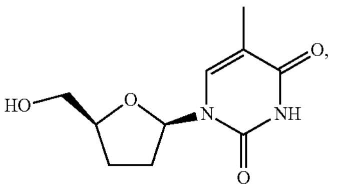 [SMILES: Cc1cn([C@H]2CC[C@@H](CO)O2)c(=O)[nH]c1=O]

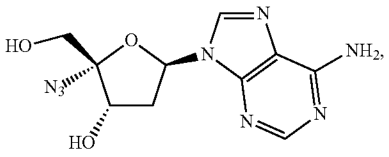 [SMILES: [N-]=[N+]=N[C@]1(CO)O[C@@H](n2cnc3c(N)ncnc32)C[C@@H]1O]

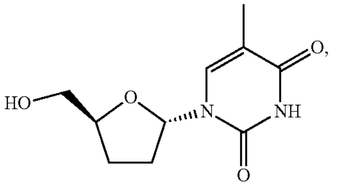 [SMILES: Cc1cn([C@@H]2CC[C@@H](CO)O2)c(=O)[nH]c1=O]

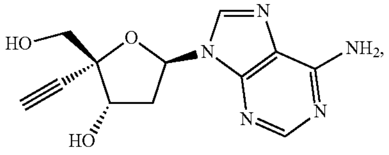 [SMILES: C#C[C@]1(CO)O[C@@H](n2cnc3c(N)ncnc32)C[C@@H]1O]

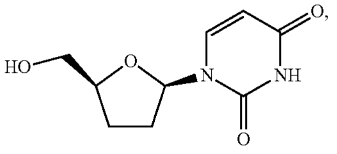 [SMILES: O=c1ccn([C@H]2CC[C@@H](CO)O2)c(=O)[nH]1]

TABLE 1B-continued

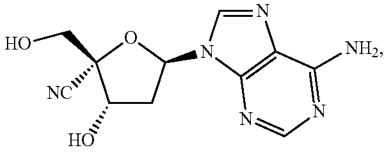 [SMILES: N#C[C@]1(CO)O[C@@H](n2cnc3c(N)ncnc32)C[C@@H]1O]

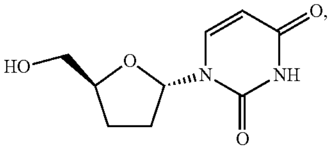 [SMILES: O=c1ccn([C@@H]2CC[C@@H](CO)O2)c(=O)[nH]1]

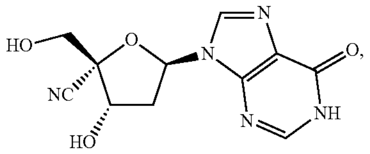 [SMILES: N#C[C@]1(CO)O[C@@H](n2cnc3c(=O)[nH]cnc32)C[C@@H]1O]

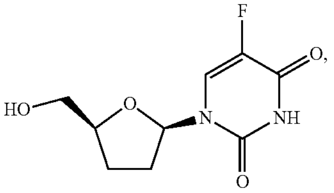

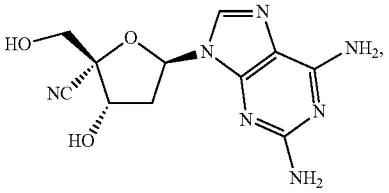 [SMILES: N#C[C@]1(CO)O[C@@H](n2cnc3c(N)nc(N)nc32)C[C@@H]1O]

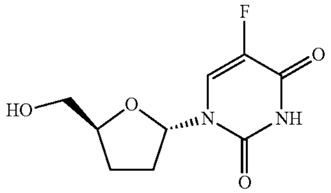

or

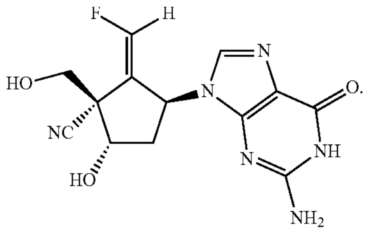 [SMILES: N#C[C@]1(CO)/C(=C\F)[C@@H](n2cnc3c(=O)[nH]c(N)nc32)C[C@@H]1O]

The compounds Table 1, Table 1A, and Table 1B may be found and prepared as described, for example, in Nomura et al., *J. Med. Chem.* 42:2901-2908 (1999); Ohrui et al., *J. Med. Chem.* 43:4516-4525 (2000), Ohrui, H., *Proc. Jpn. Acad. Ser. B* 87:53-65 (2011); Banuelos-Sanchez et al., *Cell Chemical Biology* 26:1095-1109 (2019); Kirby et al., *Antimicrobial Agents and Chemotherapy* 57:6254-6264 (2013), Higashi-Kuwata et al., *Journal of Hepatology* 74:1075-1086 (2021), JP Patent No. 6767011, U.S. Pat. No. 10,933,067, and/or as described in EXAMPLES 2-4, below.

In another embodiment, the Compound of the Disclosure is tenofovir alafenamide.

II. Therapeutic Methods and Uses

A Compound of the Disclosure, or pharmaceutical composition thereof, can be administered to a subject in need thereof, e.g., a subject already suffering from a disease, condition, or disorder; a subject suspected of having a disease, condition, or disorder; or a subject at risk of acquiring a disease, condition, or disorder. When a Compound of the Disclosure is administered to a subject at risk of acquiring a disease, condition, or disorder, the intention is to try to avoid the disease, condition, or disorder in the subject, e.g. by preventing or reducing the LINE-1 retrotransposition activity that causes the disease, condition, or disorder.

In one embodiment, the disclosure provides a method of treating or preventing a disease, disorder, or condition in a subject in need thereof, and/or treating or preventing a symptom of the disease, disorder, or condition, the method comprising administering a therapeutically effective amount of a Compound of the Disclosure, or pharmaceutical composition thereof, to the subject.

In another embodiment, the disclosure provides a method of treating a disease, disorder, or condition in a subject in need thereof, the method comprising administering a therapeutically effective amount of a Compound of the Disclosure, or pharmaceutical composition thereof, to the subject.

In another embodiment, the disclosure provides a method of preventing a disease, disorder, or condition in a subject in need thereof, the method comprising administering a therapeutically effective amount of a Compound of the Disclosure, or pharmaceutical composition thereof, to the subject.

In another embodiment, the disclosure provides a method of treating a symptom of a disease, disorder, or condition in a subject in need thereof, the method comprising administering a therapeutically effective amount of a Compound of the Disclosure, or pharmaceutical composition thereof, to the subject.

In another embodiment, the disclosure provides a method of preventing a symptom of a disease, disorder, or condition in a subject in need thereof, the method comprising administering a therapeutically effective amount of a Compound of the Disclosure, or pharmaceutical composition thereof, to the subject.

In another embodiment, the disclosure provides a Compound of the Disclosure, or pharmaceutical composition thereof, for use in treating or preventing a disease, disorder, or condition in a subject and/or treating or preventing a symptom of the disease, disorder, or condition.

In another embodiment, the disclosure provides a Compound of the Disclosure, or pharmaceutical composition thereof, for use in treating a disease, disorder, or condition in a subject.

In another embodiment, the disclosure provides a Compound of the Disclosure, or pharmaceutical composition thereof, for use in preventing a disease, disorder, or condition in a subject.

In another embodiment, the disclosure provides a Compound of the Disclosure, or pharmaceutical composition thereof, for use in treating a symptom of a disease, disorder, or condition in a subject.

In another embodiment, the disclosure provides a Compound of the Disclosure, or pharmaceutical composition thereof, for use preventing a symptom of a disease, disorder, or condition in a subject.

In another embodiment, the disclosure provides the use of a Compound of the Disclosure, or pharmaceutical composition thereof, in the manufacture of a medicament for treating or preventing a disease, disorder, or condition in a subject and/or treating or preventing a symptom of the disease, disorder, or condition.

In another embodiment, the disclosure provides the use of a Compound of the Disclosure, or pharmaceutical composition thereof, in the manufacture of a medicament for treating a disease, disorder, or condition in a subject.

In another embodiment, the disclosure provides the use of a Compound of the Disclosure, or pharmaceutical composition thereof, in the manufacture of a medicament for preventing a disease, disorder, or condition in a subject.

In another embodiment, the disclosure provides the use of a Compound of the Disclosure, or pharmaceutical composition thereof, in the manufacture of a medicament for treating a symptom of a disease, disorder, or condition in a subject.

In another embodiment, the disclosure provides the use of a Compound of the Disclosure, or pharmaceutical composition thereof, in the manufacture of a medicament for preventing a symptom of the disease, disorder, or condition in a subject.

In another embodiment, the subject is (a) not infected with the HIV virus, (b) not suspected of being infected with the HIV virus, (c) not being treated for the HIV virus, and/or (d) not being treated to prevent the HIV virus.

In another embodiment, the disclosure provides a method of inhibiting a LINE-1 retrotransposition event that causes a disease, disorder, or condition in a subject in need thereof, the method comprising administering to the subject a therapeutically effective amount of a Compound of the Disclosure.

III. Diseases, Disorders, and Conditions

Compounds of the Disclosure inhibit LINE-1 retrotransposition activity and thus can be used to treat or prevent diseases, disorders, or conditions in a subject. In some embodiments, the disease, disorder, or condition is not (i) cancer; or (ii) an infectious disease.

In one embodiment, Compounds of the Disclosure inhibit human LINE-1 retrotransposition activity with a half maximal inhibitory concentration ($IC_{50}$) of 1 μM or less in an in vitro HeLa cell-based dual-luciferase assay as described in EXAMPLE 2, see below. See also Jones et al., (2008) *PLoS ONE* 3(2): e1547. doi:10.1371/journal.pone.0001547; Xie et al., (2011) *Nucleic Acids Res.* 39(3): e16. doi: 10.1093/nar/gkq1076; Kopera et al., *Methods Mol Biol* 1400:139-156 (2016). In another embodiment, the $IC_{50}$ is 0.5 μM or less. In another embodiment, the $IC_{50}$ is 0.25 μM or less. In another embodiment, the $IC_{50}$ is 0.15 μM or less. In another embodiment, the $IC_{50}$ is 0.1 μM or less. In another embodiment, the $IC_{50}$ is 0.05 μM or less. In another embodiment, the $IC_{50}$ is 0.01 μM or less. In another embodiment, the $IC_{50}$ is 0.005 μM or less.

In one embodiment, the disease, disorder, or condition, and/or symptom(s) thereof is caused by a pathophysiological retrotransposon-associated process, wherein the disease, disorder, or condition is not cancer and/or not an infectious disease.

In another embodiment, the disease, disorder, or condition, and/or symptom(s) thereof is caused by a pathophysiological LINE-1-associated process, wherein the disease, disorder, or condition is not cancer and/or not an infectious disease.

In another embodiment, the disease, disorder, or condition is a neurodegenerative disease. See, e.g., Dugger and Dickson, *Cold Spring Harb Perspect Biol* 2016; 9:a028035.

Exemplary neurodegenerative diseases include, but are not limited to, Alzheimer's disease, amyotrophic lateral sclerosis (ALS), Parkinson's disease, dementia with Lewy Bodies (DLB), multi systems atrophy (MSA), Huntington's disease, frontotemporal lobar degeneration (FTLD), mild cognitive impairment (MCI), corticobasal degeneration (CDB), progressive supra nuclear palsy (PSP), Rett Syndrome, peripheral degenerative disease, or Aicardi-Goutières syndrome (AGS). In another embodiment, the frontotemporal lobar degeneration is frontotemporal dementia. See, e.g., Mohandas and Rajmohan, *Indian J Psychiatry* 51(Suppl 1):565-569 (2009).

In another embodiment, symptoms of the neurodegenerative disease include, but are not limited to, memory loss, forgetfulness, apathy, anxiety, agitation, a loss of inhibition, or mood changes, In another embodiment, the disease, disorder, or condition is an autoimmune disease. See, e.g., Wang et al., *J Intern Med* 278:369-395 (2016). Exemplary autoimmune diseases include, but are not limited to, lupus, rheumatoid arthritis (RA), Sjogrens syndrome, or multiple sclerosis (MS).

In another embodiment, symptoms of the autoimmune disease include, but are not limited to, fatigue, achy muscles, swelling and redness, low-grade fever, trouble concentrating, numbness and tingling in the hands and feet, hair loss, or skin rash.

In another embodiment, the disease, disorder, or condition is an age-associated disease. See, e.g., Franceschi et al., *Front. Med.* 5:61. doi: 10.3389/fmed.2018.00061; De Cecco et al., *Nature* 5666:73-78 (2019); WO 2020/154656. Exemplary age-associated diseases include, but are not limited to, Alzheimer's disease, Parkinson's disease, atherosclerosis, osteoarthritis, osteoporosis, rheumatoid arthritis (RA), macular degeneration, peripheral degenerative disease, or skin aging. In one embodiment, the subject having the age-associated disease is at least 40 years old. In one embodiment, the subject having the age-associated disease is at least 45 years old. In one embodiment, the subject having the age-associated disease is at least 50 years old. In one embodiment, the subject having the age-associated disease is at least 55 years old. In one embodiment, the subject having the age-associated disease is at least 60 years old. In one embodiment, the subject having the age-associated disease is at least 65 years old. In one embodiment, the subject having the age-associated disease is at least 70 years old. In one embodiment, the subject having the age-associated disease is at least 75 years old.

In another embodiment, the disease, disorder, or condition is autism spectrum disorder (ADS), cardiovascular dysfunction, hearing loss, hematopoietic stem cell function, pulmonary fibrosis, schizophrenia, or vision loss.

In another embodiment, the disease, disorder, or condition is wound healing in a subject in need thereof.

In another embodiment, the disease, disorder, or condition is tissue regeneration in a subject in need thereof.

In another embodiment, the disease, disorder, or condition is Alzheimer's disease.

In another embodiment, the symptom of Alzheimer's disease any one or more of memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory, or loss of long term memory, and combinations thereof.

In another embodiment, the symptom(s) of Alzheimer's disease are determined using the cognitive subscale of the Alzheimer's disease Assessment Scale (ADAS-cog), the Clinician's Interview-Based Impression of Change (CIBIC-plus), or the Activities of Daily Living Scale (ADL).

In another embodiment, the disease, disorder, or condition is Alzheimer's disease, and one or more optional therapeutic agents are administered to the subject. In another embodiment, the optional therapeutic agents are donepezil, galantamine, rivastigmine, memantine, bapineuzumab, ABBV-8E12, CTS-21166, verubecestat (MK-8931), lanabecestat (AZD3293), LY2886721, nicotinamide, or MPT0G211.

In another embodiment, the disease, disorder, or condition is amyotrophic lateral sclerosis.

In another embodiment, the disease, disorder, or condition is amyotrophic lateral sclerosis and one or more optional therapeutic agents are administered to the subject. In another embodiment, the optional therapeutic agents are edaravone, riluzole, raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.

In another embodiment, the disease is ataxia-telangiectasia.

In another embodiment, the disease is age-related macular degeneration, systemic lupus erythematosus, IFN-associated autoimmune disease, e.g., rheumatoid arthritis, psoriasis, vitiligo, hypothyroidism, hyperthyroidism, idiopathic thrombocytopenic purpura, autoimmune hemolytic anemia, myasthenia gravis, Addison disease, celiac disease, polymyositis, or superimposed autoimmune hepatitis, Fanconi Anemia, idiopathic pulmonary fibrosis, or cardiovascular disease. In another embodiment, the systemic disease is age-related macular degeneration. In another embodiment, the systemic disease is systemic lupus erythematosus. In another embodiment, the systemic disease is an IFN-associated autoimmune disease, e.g., psoriasis. In another embodiment, the systemic disease is Fanconi Anemia. In another embodiment, the systemic disease is idiopathic pulmonary fibrosis. In another embodiment, the systemic disease is cardiovascular disease.

In one embodiment, a Compound of the Disclosure is administered to a subject having a disease, disorder, or condition as a single agent.

In another embodiment, a Compound of the Disclosure is administered to a subject having a disease, disorder, or condition in combination with one or more optional therapeutic agents. See, e.g., Durdes et al., *Pharmaceuticals* 2018, 11, 44; doi:10.3390/ph11020044 for optionally therapeutic agents to treat neurodegenerative diseases.

In another embodiment, a Compound of the Disclosure is administered to a subject having a disease, disorder, or condition in combination with one optional therapeutic agent. In another embodiment, a Compound of the Disclosure is administered to a subject having a disease, disorder, or condition in combination with two optional therapeutic agents. In another embodiment, a Compound of the Disclosure is administered to a subject having a disease, disorder, or condition in combination with three optional therapeutic agents.

The Compound of the Disclosure and the one or more optional therapeutic agents can be administered in combination under one or more of the following conditions: at different periodicities, at different durations, at different concentrations, by different administration routes, etc.

In one embodiment, the Compound of the Disclosure and the one or more optional therapeutic agents are administered in combination to a subject as part of a single pharmaceutical composition.

In another embodiment, the Compound of the Disclosure and the one or more optional therapeutic agents are administered in combination to a subject separately, e.g., as two or more separate pharmaceutical compositions. In this case, two separate pharmaceutical compositions—one comprising the Compound of the Disclosure and one comprising the optional therapeutic agent—are administered to a subject. The separate pharmaceutical compositions can be administered to the subject, for example, at different periodicities, at different durations, or by the same or different administration routes, e.g., the Compound of the Disclosure can be administered orally and the optionally therapeutic agent can be administered intravenously.

In another embodiments, the Compound of the Disclosure is administered to the subject prior to the one or more optional therapeutic agents, e.g., 0.5, 1, 2, 3, 4, 5, 10, 12, or 18 hours, 1, 2, 3, 4, 5, or 6 days, or 1, 2, 3, or 4 weeks prior to the administration of the one or more optional therapeutic agents.

In another embodiments, the Compound of the Disclosure is administered to the subject after the one or more optional therapeutic agents, e.g., 0.5, 1, 2, 3, 4, 5, 10, 12, or 18 hours, 1, 2, 3, 4, 5, or 6 days, or 1, 2, 3, or 4 weeks after the administration of the one or more optional therapeutic agents.

In another embodiments, the Compound of the Disclosure and the one or more optional therapeutic agents are administered concurrently.

In one embodiment, the Compound of the Disclosure is administered to the subject according to a continuous dosing schedule.

In one embodiment, the Compound of the Disclosure is administered to the subject according to an intermittent dosing schedule.

In one embodiment, the Compound of the Disclosure is orally administered to the subject.

The therapeutic methods provided herein comprise administering a Compound of the Disclosure to a subject having a disease, disorder, or condition in an amount which is effective to achieve its intended purpose. While individual needs vary, determination of optimal ranges of effective amounts of each component is within the skill of the art. Typically, the Compound of the Disclosure is administered in an amount from about 0.01 mg/kg to about 500 mg/kg, about 0.05 mg/kg to about 100 mg/kg, about 0.05 mg/kg to about 50 mg/kg, or about 0.05 mg/kg to about 10 mg/kg. In one embodiment, the Compound of the Disclosure is administered once a day. In another embodiment, the Compound of the Disclosure is administered twice a day. In one embodiment, the Compound of the Disclosure is administered three times a day. In one embodiment, the Compound of the Disclosure is administered four times a day. These dosages are exemplary, but there can be individual instances in which higher or lower dosages are merited, and such are within the scope of this disclosure. In practice, the physician determines the actual dosing regimen that is most suitable for an individual subject, which can vary with the age, weight, and response of the particular subject.

The unit dose may comprise from about 0.01 mg to about 1000 mg, e.g., about 1 mg to about 500 mg, e.g., about 1 mg to about 250 mg, e.g., about 1 mg to about 100 mg of the Compound of the Disclosure. For example, the unit oral dose of the Compound of the Disclosure may comprise, for example 1 mg, 2 mg, 3 mg, 4 mg, 5 mg, 6 mg, 7 mg, 8 mg, 9 mg, or 10 mg. The unit dose may be administered one or more times daily, e.g., as one or more tablets or capsules. The unit dose may also be administered by any suitable route, e.g., orally, by IV, inhalation or subcutaneously to the subject. In practice, the physician determines the actual dosing regimen that is most suitable for an individual subject, which can vary with the age, weight, and response of the particular subject.

In one embodiment, the Compound of the Disclosure is administered to a subject in an amount from about 0.1 mg to about 100 mg once a day, twice a day, three times a day, or four times a day. In another embodiment, the Compound of the Disclosure is administered to a subject in an amount from about 1 mg to about 50 mg per day.

In one embodiment, the Compound of the Disclosure is administered to the subject in a single dose. In another embodiment, the Compound of the Disclosure is administered to the subject in two divided doses. In another embodiment, the Compound of the Disclosure is administered to the subject in three divided doses. In another embodiment, the Compound of the Disclosure is administered to the subject in four divided doses.

The Compound of the Disclosure can be administered to a subject in the form of a raw chemical or as part of a pharmaceutical composition containing the Compound of the Disclosure combined with a suitable pharmaceutically acceptable carrier. Such a carrier can be selected from pharmaceutically acceptable excipients, vehicles, and auxiliaries. The term "pharmaceutically acceptable carrier," "pharmaceutically acceptable vehicle," or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

A pharmaceutical composition comprising the Compound of the Disclosure can contain from about 0.01 to 99 percent by weight, e.g., from about 0.25 to 75 percent by weight, of the Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of the Compound of the Disclosure.

The Compound of the Disclosure, or pharmaceutical composition comprising the Compound of the Disclosure, can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration to a subject. Dosage forms depend on the route administration. Dosage forms include, but are not limited to, tablets, dragees, slow release lozenges, capsules, liquid solutions, liquid suspensions, oral/nasal spray, transdermal patch, thin dissolvable film, ointments, sustained or controlled release implants, mouth rinses and mouth washes, gels, hair rinses, hair gels, and shampoos, and suppositories, as well as suitable solutions for administration by intravenous infusion, and suitable suspensions for administration subcutaneous injection, and suitable powders for reconstitution. Parenteral administration can be accomplished using a needle and syringe or using other technique known in the art. In one embodiment, the Compound of the Disclosure is administered orally to the subject. In one embodiment, the Compound of the Disclosure is administered subcutaneously to the subject. In one embodiment, the Compound of the Disclosure is administered intravenously to the subject.

The Compound of the Disclosure and pharmaceutical compositions comprising the Compound of the Disclosure may be administered to any subject which may experience the beneficial effects of inhibiting LINE-1 retrotransposition activity. The term "subject" as used herein refers to any human or animal that is in need of or might benefit from administration of the Compound of the Disclosure. Foremost among such subjects are mammals, e.g., humans, although the methods and compositions provided herein are not intended to be so limited. Other subjects include veterinary animals, e.g., cows, sheep, pigs, horses, dogs, cats and the like. In one embodiment, the subject is a human. In one embodiment, the subject is an animal. In another embodiment, the subject is a human having a disease, condition, or disorder responsive to LINE-1 inhibition.

The pharmaceutical preparations provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of a Compound of the Disclosure may be administered to a subject. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers and other additives.

Therapeutically effective amounts of a Compound of the Disclosure formulated in accordance with standard pharmaceutical practices are administered to a subject in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of the Compound of the Disclosure that is sufficient to maintain therapeutic effects.

Toxicity and therapeutic efficacy of the Compound of the Disclosure can be determined by standard pharmaceutical procedures in cell cultures or experimental animals, e.g., for determining the maximum tolerated dose (MTD) of a compound, which defines as the highest dose that causes no toxicity in a subject. The dose ratio between the maximum tolerated dose and therapeutic effects is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of the Compound of the Disclosure required for use in therapy varies with the nature of the disease being treated, the length of time that activity is desired, and the age and the condition of the subject, and ultimately is determined by the attendant physician. For example, dosage amounts and intervals can be adjusted individually to provide plasma levels of a Compound of the Disclosure that are sufficient to maintain the desired therapeutic effects. The desired dose conveniently can be administered in a single dose, or as multiple doses administered at appropriate intervals, for example as one, two, three, four or more subdoses per day.

IV. Kits

In another embodiment, the present disclosure provides kits comprising a Compound of the Disclosure, or a pharmaceutical composition thereof, and instructions for administering the compound or composition to a subject having a disease, disorder, or condition.

In another embodiment, the present disclosure provides kits comprising a Compound of the Disclosure, or a pharmaceutical composition thereof, packaged in a manner that facilitates their use to practice methods of the present disclosure.

In one embodiment, the kit includes a Compound of the Disclosure, or a pharmaceutical composition thereof, packaged in a container, such as a sealed bottle or vessel, with a label affixed to the container or included in the kit that describes use of the compound or composition to practice the method of the disclosure. In one embodiment, the compound or composition is packaged in a unit dosage form. The kit may include a single dose or multiple doses of a Compound of the Disclosure, or a pharmaceutical composition thereof.

In another embodiment, the kit includes a Compound of the Disclosure, or a composition thereof, and one or more optional therapeutic agents.

V. Biomarkers

In another embodiment, present disclosure provides methods of treating a subject having a disease, condition, or disorder, the method comprising (a) determining whether a biomarker is present or absent in a biological sample taken from the subject; and (b) administering a therapeutically effective amount of a Compound of the Disclosure to the subject if the biomarker is present in the biological sample.

The term “biomarker” as used herein refers to any biological compound, such as a gene, a protein, a fragment of a protein, a peptide, a polypeptide, a nucleic acid, etc., or chromosome abnormality, such as a chromosome translocation, that can be detected and/or quantified in a subject in vivo or in a biological sample obtained from a subject. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the subject, such as the subject’s age. For biomarkers that are detected at the protein or RNA level, such measurable aspects may include, for example, the presence, absence, or concentration, i.e., expression level, of the biomarker in the subject, or biological sample obtained from the subject. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes. The term “overexpression” indicates that the expression level of the biomarker in the subject having a disease, condition, or disorder is above the mean or median expression level of the biomarker in, e.g., a normal undiseased subject.

Biomarkers include, but are not limited to, retrotransposon RNA, retrotransposon reverse transcriptase e.g., ORF1p, ORF2p, and/or retrotransposon DNA. In one embodiment, the measurable aspect of the biomarker is its expression status. In another embodiment, the measurable aspect of the biomarker is elevated levels of the biomarker. In one embodiment, the measurable aspect of the biomarker is its mutation status.

In one embodiment, the biomarker is the expression level of LINE-1. Methods of determining the expression level of LINE-1 are described in US 2020/0253888, and may comprise, for example, determining the level of ORF1p, determining the level of LINE-1 mRNA, determining the amount of LINE-1 in a cell sample of the subject, or determining the level of ORF2p, or a combination thereof.

In one embodiment, the biomarker is retrotransposon RNA expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression retrotransposon RNA. In one embodiment, the biomarker is overexpression of retrotransposon RNA.

In one embodiment, the biomarker is LINE-1 RNA expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression LINE-1 RNA. In one embodiment, the biomarker is overexpression of LINE-1 RNA.

In another embodiment, the biomarker is retrotransposon reverse transcriptase which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression of the retrotransposon reverse transcriptase. In one embodiment, the biomarker is overexpression of retrotransposon reverse transcriptase.

In another embodiment, the biomarker is ORF1p expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression ORF1p. In one embodiment, the biomarker is overexpression of ORF1p.

In another embodiment, the biomarker is ORF2p expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression ORF2p. In one embodiment, the biomarker is overexpression of ORF2p.

Biomarker standards can be predetermined, determined concurrently, or determined after a biological sample is obtained from the subject. Biomarker standards for use with the methods described herein can, for example, include data from samples from subjects without a neurodegenerative disease; data from samples from subjects with a neurodegenerative disease. Comparisons can be made to establish predetermined threshold biomarker standards for different classes of subjects, e.g., diseased vs. non-diseased subjects. The standards can be run in the same assay or can be known standards from a previous assay.

In one embodiment, the biomarker is retrotransposon DNA expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression retrotransposon DNA. In one embodiment, the biomarker is overexpression of retrotransposon DNA. In another embodiment, the biomarker is overexpression of retrotransposon nuclear DNA. In another embodiment, the biomarker is overexpression of retrotransposon cytoplasmic DNA.

In one embodiment, the biomarker is LINE-1 DNA expression which is differentially present in a subject of one phenotypic status, e.g., a subject having an age-associated disease or a neurodegenerative disease, as compared with another phenotypic status, e.g., a normal undiseased subject or a subject having a disease, disorder, or condition without overexpression LINE-1 DNA. In one embodiment, the biomarker is overexpression of LINE-1 DNA. In another embodiment, the biomarker is overexpression of LINE-1 nuclear DNA. In another embodiment, the biomarker is overexpression of LINE-1 cytoplasmic DNA.

A biomarker is differentially present between different phenotypic status groups if the mean or median expression or mutation levels of the biomarker is calculated to be different, i.e., higher or lower, between the groups. Thus, biomarkers provide an indication that a subject, e.g., a subject having ALS, belongs to one phenotypic status or another.

In addition to individual biological compounds, e.g., LINE-1 RNA, the term "biomarker" as used herein is meant to include groups, sets, or arrays of multiple biological compounds. For example, the combination of LINE-1 RNA overexpression and ORF1p overexpression may comprise a biomarker, or the overexpression of LINE-1 RNA and LINE-1 DNA may comprise a biomarker. The term "biomarker" may comprise one, two, three, four, five, six, seven, eight, nine, ten, fifteen, twenty, twenty five, thirty, or more, biological compounds. In embodiment, the biomarker comprises one, two, or three biological compounds.

The determination of the expression level or mutation status of a biomarker in a subject can be performed using any of the many methods known in the art. Any method known in the art for quantitating specific proteins and/or detecting biomarker expression, e.g., LINE-1 RNA expression, ORF1p expression, and/or ORF2p expression, or the expression or mutation levels of any other biomarker(s) in a patient or a biological sample may be used in the methods of the disclosure. Examples include, but are not limited to, PCR (polymerase chain reaction), or RT-PCR, flow cytometry, Northern blot, Western blot, ELISA (enzyme linked immunosorbent assay), RIA (radioimmunoassay), gene chip analysis of RNA expression, immunohistochemistry or immunofluorescence. See, e.g., Slagle et al. Cancer 83:1401 (1998). Certain embodiments of the disclosure include methods wherein biomarker RNA expression (transcription) is determined. Other embodiments of the disclosure include methods wherein protein expression in the biological sample is determined. See, e.g., Harlow et al., Antibodies: A Laboratory Manual, Cold Spring Harbor Laboratory, Cold Spring Harbor, NY, (1988); Ausubel et al., Current Protocols in Molecular Biology, John Wiley & Sons, New York 3rd Edition, (1995); Kamel and Al-Amodi, Genomics Proteomics Bioinformatics 15:220-235 (2017). For northern blot or RT-PCR analysis, RNA is isolated from tissue sample using RNAse free techniques. Such techniques are commonly known in the art.

In one embodiment of the disclosure, a biological sample is obtained from the subject and the biological sample is assayed for determination of a biomarker expression or mutation status.

In another embodiment of the disclosure, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is prehybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabled probes and their use are well known in the art. The presence and or relative levels of expression of the biomarker being assayed can be quantified using, for example, densitometry.

In another embodiment, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used, for example, to determine the level of RNA encoding a biomarker of the disclosure in a tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., Cold Spring Harbor Symp. Quant. Biol. 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligonucleotide that is hybridized to the target amplicon (biomarker gene). RT-PCR probes are oligonucleotides that have a fluorescent reporter dye attached to the 5' end and a quencher moiety coupled to the 3' end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In another embodiment of the disclosure, the expression of a protein, e.g., ORF1p, ORF2p, encoded by a biomarker is detected by s single molecule array assay (Simoa™).

In another embodiment of the disclosure, the expression of a protein, e.g., ORF1p, ORF2p, encoded by a biomarker is detected droplet digital ELISA (ddELISA). Using ddELISA, LINE-1/ORF1p protein can be measured in serum. See Cohen et al., *ACS Nano* 14:9491-9501 (2020).

VI. Definitions

The term "pathophysiological retrotransposon-associated process" as used herein refers to a disordered physiological process relating to aberrant retrotransposition activity of at least one retrotransposon. Exemplary retrotransposons include, but are not limited to, LINE-1 and human endogenous retroviruses (HERVs), e.g., HERV-K and HERV-E. See, e.g., Saleh et al, (2019) *Front. Neurol.* 10:894. doi: 10.3389/fneur.2019.00894. Diseases, disorders, or conditions caused by a pathophysiological retrotransposon-associated process include, but are not limited to, neurodegenerative diseases, autoimmune diseases, age-associated diseases, autism spectrum disorder (ADS), cardiovascular dysfunction, hearing loss, hematopoietic stem cell function, pulmonary fibrosis, schizophrenia, or vision loss.

The term "pathophysiological LINE-1-associated process" as used herein refers to a disordered physiological process relating to aberrant LINE-1 (L1) retrotransposition activity. See, e.g., Saleh et al, (2019) *Front. Neurol.* 10:894. doi: 10.3389/fneur.2019.00894; Zhao et al., PLoS Genet 15(4): e1008043. https://doi.org/10.1371/journal.pgen.1008043; Bundo et al., *Neuron* 81:306-313 (2014).

The term "LINE-1 retrotransposition event that causes a disease, disorder, or condition" as used herein refers to any causal factor, e.g., aberrant transcription, alternative splicing, insertional mutagenesis, DNA damage, chromosomal translocation, increased expression of LINE-1 RNA, ORF1p (a 40 kDa RNA-binding protein), ORF2p (a ~150 kDa protein with endonuclease (EN) and reverse transcriptase (RT) activities) associated with LINE-1 retrotransposition that results in or promotes a pathological condition, e.g., a disease or disorder, in a subject. See, e.g., Beck et al., *Annu Rev Genomics Hum Genet* 12:187-215 (2011); Pizarro and Cristofari (2016) *Front. Cell Dev. Biol.* 4:14, https://doi.org/10.3389/fcell.2016.00014. In one embodiment, the LINE-1 retrotransposition event is a somatic LINE-1 insertion. In another embodiment, LINE-1 retrotransposition event is increased expression of LINE-1 RNA in the subject.

The term "tautomer" as used herein refers to each of two or more isomers of a compound which exist together in equilibrium, and are interchanged by migration of an atom, e.g., a hydrogen, or group within the molecule. Certain Compounds of the Disclosure may exist as tautomers. In situations where tautomers are possible, the present disclosure includes all tautomeric forms. For example, as illustrated in Chart 1, both the lactim and lactam tautomers are encompassed by Formula II when $R^4$ is —OH, and both the amino and imino tautomers are encompassed by Formula II when $R^4$ is $—NH_2$.

Chart 1

$R^4$ = —OH

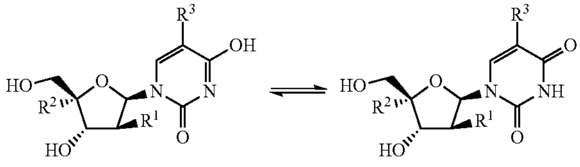

II (lactim) II (lactam)

$R^4$ = $—NH_2$

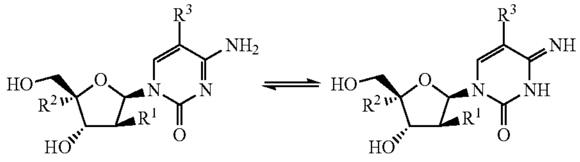

II (amino) II (imino)

Likewise, as illustrated in Chart 2, both the lactim and lactam tautomers are encompassed by Formula III when $R^5$ is —OH, and both the amino and imino tautomers are encompassed by Formula III when $R^5$ is $—NH_2$.

Chart 2

$R^4$ = —OH

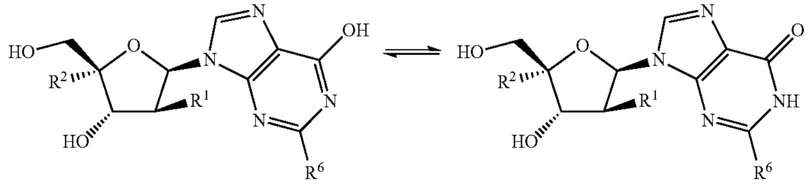

III (lactim) III (lactam)

$R^4$ = —$NH_2$

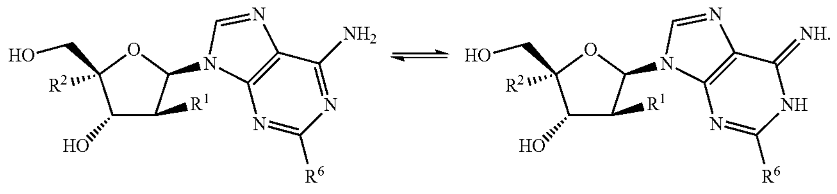

III (amino) III (imino)

The equilibrium arrows in Charts 1 and 2 are not intended to show the position of the equilibrium, only that an equilibrium exists between the two tautomeric forms.

The term "biological sample" as used herein refers any tissue or fluid from a subject that is suitable for detecting a biomarker. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for the expression level of a biological compound, e.g., LINE-1 RNA, ORF1p protein, ORF2p protein, using any technique known in the art. Such techniques include, but are not limited to, polymerase chain reaction (PCR) methodology, reverse transcription-polymerase chain reaction (RT-PCR) methodology, or cytoplasmic light chain immunofluorescence combined with fluorescence in situ hybridization (cIg-FISH). A biological sample can be obtained using techniques that are well within the scope of ordinary knowledge of a clinical practitioner. In one embodiment of the disclosure, the biological sample comprises a tissue or blood sample.

The terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language, e.g., "such as," provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number±10%. Thus, "about 10" means 9 to 11.

As used herein, the terms "treat," "treating," "treatment," and the like refer to eliminating, reducing, or ameliorating a disease, disorder, or condition, and/or the symptoms associated therewith. Although not precluded, treating a disease, disorder, or condition does not require that the disease, disorder, or condition, and/or symptom(s) associated therewith be completely eliminated. However, in one embodiment, administration of a Compound of the Disclosure leads to complete elimination of the disease and associated symptoms.

As used herein, the terms "prevent," "preventing," "prevention" and the like refer to a method of preventing the onset of a disease, disorder, or condition and/or symptom(s) associated therewith, or barring a subject from acquiring the disease, disorder, or condition. The terms "prevent," "preventing," and "prevention" also include delaying the onset of disease, disorder, or condition and/or its attendant symptom(s), and reducing a subject's risk of acquiring the disease, disorder, or condition. The terms "prevent," "preventing" and "prevention" also includes "prophylactic treatment," which refers to reducing the probability of redeveloping the disease, disorder, or condition, or of a recurrence of a previously-controlled disease, disorder, or condition, in a subject who does not have, but is at risk of or is susceptible to, redeveloping the disease, disorder, or condition or a recurrence of the disease, disorder, or condition. The terms "prevent," "preventing" and "prevention" also include delaying or reversing the progression of the underlying pathology of the disease, disorder, or condition, e.g., a mutation caused by a somatic LINE-1 insertion.

The term "therapeutically effective amount," as used herein, refers to that amount of a Compound of the Disclosure and, optionally, one or more optional therapeutic agents sufficient to result in amelioration of one or more symptoms of a disease, disorder, or condition, or prevent advancement of a disease, disorder, or condition, or cause regression of a disease, disorder, or condition. For example, a therapeutically effective amount will refer to the amount of a Compound of the Disclosure that causes a therapeutic response, e.g., delay the progression of the disease, disorder, or condition in subject by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

The term "container" means any receptacle and closure therefore suitable for storing, shipping, dispensing, and/or handling the Compound of the Disclosure. Non-limiting exemplary containers include vials, ampules, bottles, and syringes.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

In some embodiments, when administered in combination, two or more therapeutic agents can have a synergistic effect. The terms "synergy," "synergistic," "synergistically" and derivations thereof, such as in a "synergistic effect" or a "synergistic combination" or a "synergistic composition" as used herein refer to circumstances under which the biological activity of a combination of an agent and at least one additional therapeutic agent is greater than the sum of the biological activities of the respective agents when administered individually. For example, the term "synergistically effective" as used herein refers to the interaction between a Compound of the Disclosure and another therapeutic agent that causes the total effect of the drugs to be greater than the sum of the individual effects of each drug. Berenbaum, *Pharmacological Reviews* 41:93-141 (1989).

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index } (SI)$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

The terms "intermittent dose administration," "intermittent dosing schedule," and similar terms as used herein refer to, i.e., not continuous, administration, of a Compound of the Disclosure to a subject.

Intermittent dose administration of a Compound of the Disclosure may maintain or efficacy achieved with continuous dosing, but with less side-effects, e.g., less body weight loss. Intermittent dose administration regimens useful in the present disclosure encompass any discontinuous administration regimen that provides a therapeutically effective amount of a Compound of the Disclosure to a subject in need thereof. Intermittent dosing regimens can use equivalent, lower, or higher doses of the Compound of the Disclosure than would be used in continuous dosing regimens. Advantages of intermittent dose administration of a Compound of the Disclosure include, but are not limited to, improved safety, decreased toxicity, e.g., decreased weight loss, increased exposure, increased efficacy, and/or increased subject compliance. These advantages may be realized when the Compound of the Disclosure is administered as a single agent or when administered in combination with one or more optional therapeutic agents. On the day a Compound of the Disclosure is scheduled to be administered to the subject, administration can occur in a single or in divided doses, e.g., once-a-day, twice-a-day, three times a day, four times a day or more. Dosing can also occur via any suitable route, e.g., orally, intravenously, or subcutaneously. In one embodiment, the Compound of the Disclosure is administered to the subject once (QD) or twice (BID) on the day the compound is scheduled to be administered.

The phrase "in combination" as used in connection with the administration of a Compound of the Disclosure and one or more optional therapeutic agents to a subject means that the Compound of the Disclosure and the one or more optional therapeutic agents can be administered to the subject together, e.g., as part of a single pharmaceutical composition or formulation, or separately, e.g., as part of two or more separate pharmaceutical compositions or formulations. The phrase "in combination" as used in connection with the administration of a Compound of the Disclosure and the one or more optional therapeutic agents to a subject is thus intended to embrace administration of the Compound of the Disclosure and the one or more optional therapeutic agents in a sequential manner, wherein the Compound of the Disclosure and the one or more optional therapeutic agents are administered to the subject at a different time, as well as administration concurrently, or in a substantially simultaneous manner, e.g., less than 30 minutes apart. Simultaneous administration can be accomplished, for example, by administering to the subject a single capsule having a fixed ratio of each of the Compound of the Disclosure and the one or more optional therapeutic agents or in multiple, single capsules for each of the Compound of the Disclosure and the one or more optional therapeutic agents. Sequential or substantially simultaneous administration of the Compound of the Disclosure and the one or more optional therapeutic agents can be accomplished by any appropriate route including, but not limited to, oral routes, intravenous routes, subcutaneous routes, intramuscular routes, etc. The Compound of the Disclosure and the one or more optional therapeutic agents can be administered by the same route or by different routes. For example, the one or more optional therapeutic agents and the Compound of the Disclosure of the combination may be administered orally. Alternatively, for example, the Compound of the Disclosure tor may be administered orally and the one or more optional therapeutic agents may be administered by intravenous injection. The Compound of the Disclosure and the one or more optional therapeutic agents may also be administered in alternation. In one embodiment, the Compound of the Disclosure and the one or more optional therapeutic agents are administered to a subject separately, e.g., as part of two or more separate pharmaceutical compositions or formulations.

VII. Particular Embodiments

The disclosure provides the following particular embodiments.

Embodiment 1. A method of treating or preventing a disease, disorder, or condition caused by a pathophysiological retrotransposon-associated process in a subject in need thereof, and/or treating or preventing a symptom of the disease, disorder, or condition, the method comprising administering to the subject a therapeutically effective amount of (i) a compound of Formula I:

I

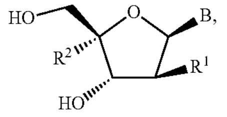

or a pharmaceutically acceptable salt or solvate thereof, or a tautomer thereof, wherein:

B is selected from the group consisting of:

B-1

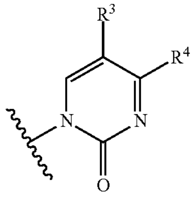

and

B-2

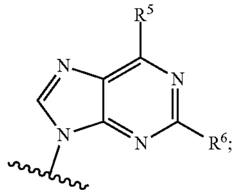

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of $-NH_2$ and —OH;

$R^5$ is selected from the group consisting of $-NH_2$ and —OH; and $R^6$ is selected from the group consisting of hydrogen, chloro, and $-NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, with provisos that the disease, disorder, or condition is not (i) cancer; or (ii) an infectious disease.

Embodiment 2. A method of inhibiting a LINE-1 retrotransposition event that causes a disease, disorder, or condition in a subject in need thereof, the method comprising administering to the subject a therapeutically effective amount of (i) a compound of Formula I:

I

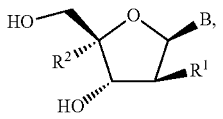

or a pharmaceutically acceptable salt or solvate thereof, or a tautomer thereof, wherein:

B is selected from the group consisting of:

B-1

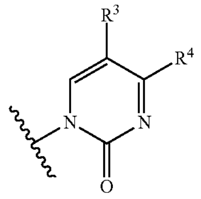

and

B-2

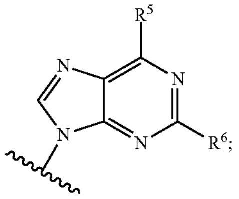

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of $-NH_2$ and —OH;

$R^5$ is selected from the group consisting of $-NH_2$ and —OH; and $R^6$ is selected from the group consisting of hydrogen, chloro, and $-NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof.

Embodiment 3. A method of treating a disease, condition, or disorder in a subject, the method comprising:

(a) determining whether an overexpression of retrotransposon RNA, retrotransposon reverse transcriptase, or retrotransposon DNA is present or absent in a biological sample taken from the subject; and (b) administering a therapeutically effective amount of (i) a compound of Formula I:

I

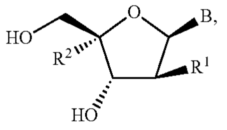

or a pharmaceutically acceptable salt or solvate thereof, or a tautomer thereof, wherein:

B is selected from the group consisting of:

B-1

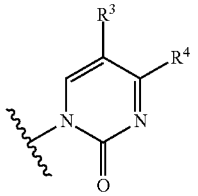

and

B-2

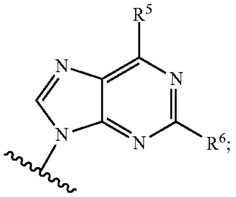

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, to the subject if an overexpression of retrotransposon RNA, retrotransposon reverse transcriptase, or retrotransposon DNA is present in the biological sample.

Embodiment 4. A method of identifying whether a subject having a disease, condition, or disorder is a candidate for treatment with (i) a compound of Formula I:

I

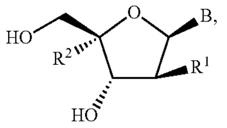

or a pharmaceutically acceptable salt or solvate thereof, or a tautomer thereof, wherein:

B is selected from the group consisting of:

B-1

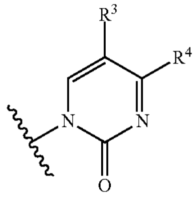

and

B-2

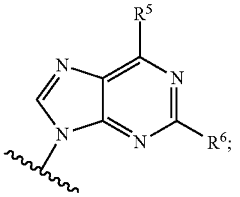

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, the method comprising:

(a) determining whether an overexpression of retrotransposon RNA, retrotransposon reverse transcriptase, or retrotransposon DNA is present or absent in a biological sample taken from the subject; and (b) identifying the subject as being a candidate for treatment if an overexpression of retrotransposon RNA, retrotransposon reverse transcriptase, or retrotransposon DNA is present; or (c) identifying the subject as not being a candidate for treatment if an overexpression of retrotransposon RNA, retrotransposon reverse transcriptase, or retrotransposon DNA is absent.

Embodiment 5. A method of predicting treatment outcome in a subject having a disease, condition, or disorder, the method comprising determining whether an overexpression of retrotransposon RNA, retrotransposon reverse transcriptase, or retrotransposon DNA is present or absent in a biological sample taken from the subject, wherein:

(a) the presence of an overexpression of retrotransposon RNA, retrotransposon reverse transcriptase, or retrotransposon DNA in the biological sample indicates that administering (i) a compound of Formula I:

I

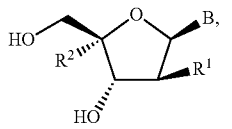

or a pharmaceutically acceptable salt or solvate thereof, or a tautomer thereof, wherein:

B is selected from the group consisting of:

B-1

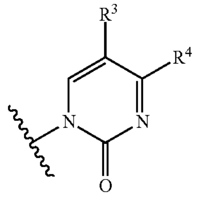

and

B-2

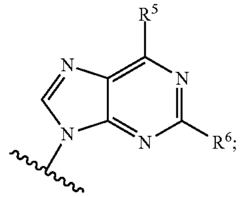

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, to the subject will likely cause a favorable therapeutic response; and (b) the absence of an overexpression of retrotransposon RNA, retrotransposon reverse transcriptase, or retrotransposon DNA in the biological sample indicates that administering (i) the compound of Formula I, or a pharmaceutically acceptable salt or solvate thereof, or a tautomer thereof, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, to the subject will likely cause an unfavorable therapeutic response.

Embodiment 6. A method, comprising administering a therapeutically effective amount of (i) a compound Formula I:

I

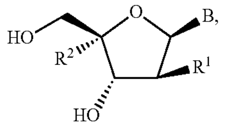

or a pharmaceutically acceptable salt or solvate thereof, or a tautomer thereof, wherein:

B is selected from the group consisting of:

B-1

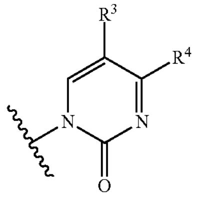

and

B-2

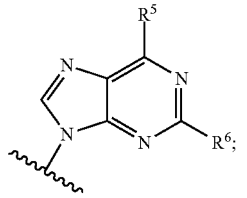

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, to a subject, wherein:

(a) the subject has a disease, condition, or disorder; and (b) the disease, condition, or disorder is characterized as having an overexpression of retrotransposon RNA, retrotransposon reverse transcriptase, or retrotransposon DNA.

Embodiment 7. The method of any one of Embodiments 1-6, wherein the compound of Formula I is a compound of Formula II:

II

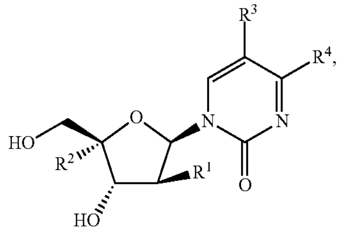

or a pharmaceutically acceptable salt or solvate thereof, or a tautomer thereof.

Embodiment 8. The method of Embodiment 7, wherein $R^3$ is hydrogen.

Embodiment 9. The method of Embodiment 7, wherein $R^3$ is selected from the group consisting of fluoro and chloro.

Embodiment 10. The method of Embodiment 7, wherein $R^3$ is methyl.

Embodiment 11. The method of any one of Embodiments 7-10, wherein $R^4$ is $-NH_2$.

Embodiment 12. The method of any one of Embodiments 7-10, wherein $R^4$ is —OH.

Embodiment 13. The method of any one of Embodiments 1-6, wherein the compound of Formula I is a compound of Formula III:

III

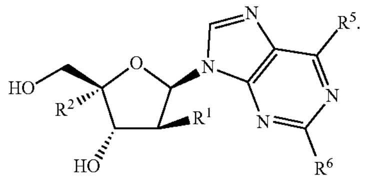

or a pharmaceutically acceptable salt or solvate thereof, or a tautomer thereof.

Embodiment 14. The method of Embodiment 13, wherein $R^5$ is $-NH_2$.

Embodiment 15. The method of Embodiment 13, wherein $R^5$ is —OH.

Embodiment 16. The method of any one of Embodiments 13-15, wherein $R^6$ is hydrogen.

Embodiment 17. The method of any one of Embodiments 13-15, wherein $R^6$ is chloro.

Embodiment The method of any one of Embodiments 13-15, wherein $R^6$ is $-NH_2$.

Embodiment 19. The method of any one of Embodiments 1-18, wherein $R^1$ is hydrogen.

Embodiment 20. The method of any one of Embodiments 1-18, wherein $R^1$ is —OH.

Embodiment 21. The method of any one of Embodiments 1-20, wherein $R^2$ is methyl.

Embodiment 22. The method of any one of Embodiments 1-20, wherein $R^2$ is ethynyl.

Embodiment 23. The method of any one of Embodiments 1-20, wherein $R^2$ is —CN.

Embodiment 24. The method of any one of Embodiments 1-6, wherein the compound of Formula I is a compound of Table 1, or a pharmaceutically acceptable salt or solvate thereof, or a tautomer thereof.

Embodiment 25. The method of any one of Embodiments 1 or 7-24 for treating the disease, disorder, or condition in a subject.

Embodiment 26. The method of any one of Embodiments 1 or 7-24 for preventing the disease, disorder, or condition in a subject.

Embodiment 27. The method of any one of Embodiments 1 or 7-24, for treating the symptom of a disease, disorder, or condition in a subject.

Embodiment 28. The method of any one of Embodiments 1 or 7-24, for preventing the symptom of a disease, disorder, or condition in a subject.

Embodiment 29. The method of any one of Embodiments 1-28, wherein the disease, disorder, or condition is a neurodegenerative disease.

Embodiment 30. The method of Embodiment 29, wherein the neurodegenerative disease is Alzheimer's disease, amyotrophic lateral sclerosis, Parkinson's disease, dementia with Lewy Bodies, multi systems atrophy, Huntington's disease, frontotemporal lobar degeneration, mild cognitive impairment, corticobasal degeneration, progressive supra nuclear palsy, Rett Syndrome, peripheral degenerative disease, or Aicardi-Goutières syndrome.

Embodiment 31. The method of any one of Embodiments 1-28, wherein the disease, disorder, or condition is an autoimmune disease.

Embodiment 32. The method of Embodiment 31, wherein the autoimmune disease is lupus, rheumatoid arthritis, Sjogrens syndrome, or multiple sclerosis.

Embodiment 33. The method of any one of Embodiments 1-28, wherein the disease, disorder, or condition is an age-associated disease.

Embodiment 34. The method of Embodiment 33, wherein the age-associated disease is Alzheimer's disease, Parkinson's disease, atherosclerosis, osteoarthritis, osteoporosis, rheumatoid arthritis, macular degeneration, peripheral degenerative disease, or skin aging.

Embodiment 35. The method of any one of Embodiments 1-28, wherein the disease, disorder, or condition is autism spectrum disorder (ADS), cardiovascular dysfunction, hearing loss, hematopoietic stem cell function, pulmonary fibrosis, schizophrenia, or vision loss.

Embodiment 36. The method of any one of Embodiments 1-28, wherein the disease, disorder, or condition is progressive supra nuclear palsy.

Embodiment 37. The method of any one of Embodiments 1-28, wherein the disease, disorder, or condition is amyotrophic lateral sclerosis.

Embodiment 38. The method of any one of Embodiments 1-28, wherein the disease, disorder, or condition is Aicardi-Goutières syndrome.

Embodiment 39. The method of any one of Embodiments 1-3 or 5-38 further comprising one or more optional therapeutic agents to the subject.

Embodiment 40. The method of any one of Embodiments 1-39, wherein the subject is (a) not infected with the HIV virus; (b) not suspected of being infected with the HIV virus; (c) not being treated for the HIV virus; and/or (d) not being treated to prevent the HIV virus.

Embodiment 41. The method of any one of Embodiments 1-40, wherein the compound inhibits human LINE-1 retrotransposition activity with a half maximal inhibitory concentration of 1 μM or less in an in vitro HeLa cell-based dual-luciferase assay.

Embodiment 42. A kit comprising a compound of Formula I, see Embodiment 1, or a pharmaceutically acceptable salt or solvate thereof, or a tautomer thereof, wherein:

B is selected from the group consisting of B-1 and B-2, see Embodiment 1;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, and instructions for administering the compound to a subject having a disease, condition, or disorder caused by a pathophysiological retrotransposon-associated process.

Embodiment 43. The kit of Embodiment 42, wherein the compound of Formula I is a compound of Formula II, see Embodiment 7, or a pharmaceutically acceptable salt or solvate thereof, or a tautomer thereof.

Embodiment 44 The kit of Embodiment 43, wherein $R^3$ is hydrogen.

Embodiment 45. The kit of Embodiment 43, wherein $R^3$ is selected from the group consisting of fluoro and chloro.

Embodiment 46. The kit of Embodiment 43, wherein $R^3$ is methyl.

Embodiment 47. The kit of any one of Embodiments 43-46, wherein $R^4$ is —$NH_2$.

Embodiment 48. The kit of any one of Embodiments 43-46, wherein $R^4$ is —OH.

Embodiment 49. The kit of Embodiment 42, wherein the compound of Formula I is a compound of Formula III, see Embodiment 13, or a pharmaceutically acceptable salt or solvate thereof, or a tautomer thereof.

Embodiment 50. The kit of Embodiment 49, wherein $R^5$ is —$NH_2$.

Embodiment 51. The kit of Embodiment 49, wherein $R^5$ is —OH.

Embodiment 52. The kit of any one of Embodiments 49-51, wherein $R^6$ is hydrogen.

Embodiment 53. The kit of any one of Embodiments 49-51, wherein $R^6$ is chloro.

Embodiment 54. The kit of any one of Embodiments 49-51, wherein $R^6$ is —$NH_2$.

Embodiment 55. The kit of any one of Embodiments 42-54, wherein $R^1$ is hydrogen.

Embodiment 56. The kit of any one of Embodiments 42-54, wherein $R^1$ is —OH.

Embodiment 57. The kit of any one of Embodiments 42-56, wherein $R^2$ is methyl.

Embodiment 58. The kit of any one of Embodiments 42-56, wherein $R^2$ is ethynyl.

Embodiment 59. The kit of any one of Embodiments 42-56, wherein $R^2$ is —CN.

Embodiment 60. A (i) compound of Formula I, see Embodiment 1, or a pharmaceutically acceptable salt or solvate thereof, or a tautomer thereof, wherein:

B is selected from the group consisting of B-1 and B-2, see Embodiment 1;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) compound of Table 1A, or a pharmaceutically acceptable salt or solvate thereof, or a tautomer thereof, or (iii) compound of Table 1B, or a pharmaceutically acceptable salt or solvate thereof, or a tautomer thereof, for use in treating or preventing a disease, disorder, or condition caused by a pathophysiological retrotransposon-associated process in a subject in need thereof, and/or treating or preventing a symptom of the disease, disorder, or condition, with provisos that the disease, disorder, or condition is not (i) cancer; or (ii) an infectious disease.

Embodiment 61. A (i) compound of Formula I, see Embodiment 1, or a pharmaceutically acceptable salt or solvate thereof, or a tautomer thereof, wherein:

B is selected from the group consisting of B-1 and B-2, see Embodiment 1;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) compound of Table 1A, or a pharmaceutically acceptable salt or solvate thereof, or a tautomer thereof, or (iii) compound of Table 1B, or a pharmaceutically acceptable salt or solvate thereof, or a tautomer thereof, for use in inhibiting a LINE-1 retrotransposition event that causes a disease, disorder, or condition in a subject in need thereof.

Embodiment 62. A (i) compound of Formula I, see Embodiment 1, or a pharmaceutically acceptable salt or solvate thereof, or a tautomer thereof, wherein:

B is selected from the group consisting of B-1 and B-2, see Embodiment 1;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) compound of Table 1A, or a pharmaceutically acceptable salt or solvate thereof, or a tautomer thereof, or (iii) compound of Table 1B, or a pharmaceutically acceptable salt or solvate thereof, or a tautomer thereof, for use in treating a disease, condition, or disorder is characterized as having an overexpression of retrotransposon RNA, retrotransposon reverse transcriptase, or retrotransposon DNA.

Embodiment 63. The compound, or pharmaceutical composition thereof, for use of any one of Embodiments 60-62, wherein the compound of Formula I is a compound of Formula II, see Embodiment 7, or a pharmaceutically acceptable salt or solvate thereof, or a tautomer thereof.

Embodiment 64 The compound, or pharmaceutical composition thereof, for use of Embodiment 63, wherein $R^3$ is hydrogen.

Embodiment 65. The compound, or pharmaceutical composition thereof, for use of Embodiment 63, wherein $R^3$ is selected from the group consisting of fluoro and chloro.

Embodiment 66. The compound, or pharmaceutical composition thereof, for use of Embodiment 63, wherein $R^3$ is methyl.

Embodiment 67. The compound, or pharmaceutical composition thereof, for use of any one of Embodiments 63-66, wherein $R^4$ is —$NH_2$.

Embodiment 68. The compound, or pharmaceutical composition thereof, for use of any one of Embodiments 63-66, wherein $R^4$ is —OH.

Embodiment 69. The compound, or pharmaceutical composition thereof, for use of any one of Embodiments 60-62, wherein the compound of Formula I is a compound of Formula III, see Embodiment 13, or a pharmaceutically acceptable salt or solvate thereof, or a tautomer thereof.

Embodiment 70. The compound, or pharmaceutical composition thereof, for use of Embodiment 69, wherein $R^5$ is —$NH_2$.

Embodiment 71. The compound, or pharmaceutical composition thereof, for use of Embodiment 69, wherein $R^5$ is —OH.

Embodiment 72. The compound, or pharmaceutical composition thereof, for use of any one of Embodiments 69-71, wherein $R^6$ is hydrogen.

Embodiment 73. The compound, or pharmaceutical composition thereof, for use of any one of Embodiments 69-71, wherein $R^6$ is chloro.

Embodiment 74. The compound, or pharmaceutical composition thereof, for use of any one of Embodiments 69-71, wherein $R^6$ is —$NH_2$.

Embodiment 75. The compound, or pharmaceutical composition thereof, for use of any one of Embodiments 60-75, wherein $R^1$ is hydrogen.

Embodiment 76. The compound, or pharmaceutical composition thereof, for use of any one of Embodiments 60-75, wherein $R^1$ is —OH.

Embodiment 77. The compound, or pharmaceutical composition thereof, for use of any one of Embodiments 60-76, wherein $R^2$ is methyl.

Embodiment 78. The compound, or pharmaceutical composition thereof, for use of any one of Embodiments 60-76, wherein $R^2$ is ethynyl.

Embodiment 79. The compound, or pharmaceutical composition thereof, for use of any one of Embodiments 60-76, wherein $R^2$ is —CN.

Embodiment 80. The compound, or pharmaceutical composition thereof, for use of any one of Embodiments 60-62, wherein the compound of Formula I is a compound of Table 1, or a pharmaceutically acceptable salt or solvate thereof, or a tautomer thereof.

Embodiment 81. The compound, or pharmaceutical composition thereof, for use of any one of Embodiments 60 or 63-80 for treating the disease, disorder, or condition in a subject.

Embodiment 82. The compound, or pharmaceutical composition thereof, for use of any one of Embodiments 60 or 63-80 for preventing the disease, disorder, or condition in a subject.

Embodiment 83. The compound, or pharmaceutical composition thereof, for use of any one of Embodiments 60 or 63-80, for treating the symptom of a disease, disorder, or condition in a subject.

Embodiment 84. The compound, or pharmaceutical composition thereof, for use of any one of Embodiments 60 or 63-80, for preventing the symptom of a disease, disorder, or condition in a subject.

Embodiment 85. The compound, or pharmaceutical composition thereof, for use of any one of Embodiments 60-84, wherein the disease, disorder, or condition is a neurodegenerative disease.

Embodiment 86. The compound, or pharmaceutical composition thereof, for use of Embodiment 85, wherein the neurodegenerative disease is Alzheimer's disease, amyotrophic lateral sclerosis, Parkinson's disease, dementia with Lewy Bodies, multi systems atrophy, Huntington's disease, frontotemporal lobar degeneration, mild cognitive impairment, corticobasal degeneration, progressive supra nuclear palsy, Rett Syndrome, peripheral degenerative disease, or Aicardi-Goutières syndrome.

Embodiment 87. The compound, or pharmaceutical composition thereof, for use of any one of Embodiments 60-84, wherein the disease, disorder, or condition is an autoimmune disease.

Embodiment 88. The compound, or pharmaceutical composition thereof, for use of Embodiment 87, wherein the autoimmune disease is lupus, rheumatoid arthritis, Sjogrens syndrome, or multiple sclerosis.

Embodiment 89. The compound, or pharmaceutical composition thereof, for use of any one of Embodiments 60-84, wherein the disease, disorder, or condition is an age-associated disease.

Embodiment 90. The compound, or pharmaceutical composition thereof, for use of Embodiment 89, wherein the age-associated disease is Alzheimer's disease, Parkinson's disease, atherosclerosis, osteoarthritis, osteoporosis, rheumatoid arthritis, macular degeneration, peripheral degenerative disease, or skin aging.

Embodiment 91. The compound, or pharmaceutical composition thereof, for use of any one of Embodiments 60-84, wherein the disease, disorder, or condition is autism spectrum disorder (ADS), cardiovascular dysfunction, hearing loss, hematopoietic stem cell function, pulmonary fibrosis, schizophrenia, or vision loss.

Embodiment 92. The compound, or pharmaceutical composition thereof, for use of any one of Embodiments 60-84, wherein the disease, disorder, or condition is progressive supra nuclear palsy.

Embodiment 93. The compound, or pharmaceutical composition thereof, for use of any one of Embodiments 60-84, wherein the disease, disorder, or condition is amyotrophic lateral sclerosis.

Embodiment 94. The compound, or pharmaceutical composition thereof, for use of any one of Embodiments 60-84, wherein the disease, disorder, or condition is Aicardi-Goutières syndrome.

Embodiment 95. The compound, or pharmaceutical composition thereof, for use of any one of Embodiments 60-94 wherein one or more optional therapeutic agents is to be administered to the subject.

Embodiment 96. The compound, or pharmaceutical composition thereof, for use of any one of Embodiments 60-95, wherein the subject is (a) not infected with the HIV virus; (b) not suspected of being infected with the HIV virus; (c) not being treated for the HIV virus; and/or (d) not being treated to prevent the HIV virus.

Embodiment 97. The compound, or pharmaceutical composition thereof, for use of any one of Embodiments 60-96, wherein the compound inhibits human LINE-1 retrotransposition activity with a half maximal inhibitory concentration of 1 μM or less in an in vitro HeLa cell-based dual-luciferase assay.

Embodiment 98. The compound, or pharmaceutical composition thereof, for use of Embodiment 97, wherein the compound inhibits human LINE-1 retrotransposition activity with a half maximal inhibitory concentration of 0.25 μM or less in an in vitro HeLa cell-based dual-luciferase assay.

Embodiment 99. The compound for use of any one of Embodiments 60-98.

Embodiment 100. The pharmaceutical composition for use of any one of Embodiments 60-98.

Embodiment 101. Use of (i) a compound of Formula I, see Embodiment 1, or a pharmaceutically acceptable salt or solvate thereof, or a tautomer thereof, wherein:

B is selected from the group consisting of B-1 and B-2, see above;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, for the manufacture of a medicament for treating or preventing a disease, disorder, or condition caused by a pathophysiological retrotransposon-associated process in a subject in need thereof, and/or treating or preventing a symptom of the disease, disorder, or condition, with provisos that the disease, disorder, or condition is not (i) cancer; or (ii) an infectious disease.

Embodiment 102. Use of (i) a compound of Formula I, see Embodiment 1, or a pharmaceutically acceptable salt or solvate thereof, or a tautomer thereof, wherein:

B is selected from the group consisting of B-1 and B-2, see above;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, for the manufacture of a medicament for inhibiting a LINE-1 retrotransposition event that causes a disease, disorder, or condition in a subject in need thereof.

Embodiment 103. Use of (i) a compound of Formula I, see Embodiment 1, or a pharmaceutically acceptable salt or solvate thereof, or a tautomer thereof, wherein:

B is selected from the group consisting of B-1 and B-2, see above;

$R^1$ is selected from the group consisting of hydrogen and —OH;

$R^2$ is selected from the group consisting of methyl, ethynyl, and —CN;

$R^3$ is selected from the group consisting of hydrogen fluoro, chloro, bromo, iodo, and methyl;

$R^4$ is selected from the group consisting of —$NH_2$ and —OH;

$R^5$ is selected from the group consisting of —$NH_2$ and —OH; and $R^6$ is selected from the group consisting of hydrogen, chloro, and —$NH_2$, or a pharmaceutical composition thereof, (ii) a compound of Table 1A, or a pharmaceutically acceptable salt or solvate thereof, or a tautomer thereof, or (iii) a compound of Table 1B, or a pharmaceutically acceptable salt or solvate thereof, or a tautomer thereof, for the manufacture of a medicament for treating a disease, condition, or disorder is characterized as having an overexpression retrotransposon RNA, retrotransposon reverse transcriptase, or retrotransposon DNA.

Embodiment 104. The use of any one of Embodiments 101-103, wherein the compound of Formula I is a compound of Formula II, see Embodiment 7, or a pharmaceutically acceptable salt or solvate thereof, or a tautomer thereof.

Embodiment 105 The use of Embodiment 104, wherein $R^3$ is hydrogen.

Embodiment 106. The use of Embodiment 104, wherein $R^3$ is selected from the group consisting of fluoro and chloro.

Embodiment 107. The use of Embodiment 104, wherein $R^3$ is methyl.

Embodiment 108. The use of any one of Embodiments 104-107, wherein $R^4$ is —$NH_2$.

Embodiment 109. The use of any one of Embodiments 104-107, wherein $R^4$ is —OH.

Embodiment 110. The use of any one of Embodiments 101-103, wherein the compound of Formula I is a compound of Formula III, see Embodiment 13, or a pharmaceutically acceptable salt or solvate thereof, or a tautomer thereof.

Embodiment 111. The use of Embodiment 110, wherein $R^5$ is —$NH_2$.

Embodiment 112. The use of Embodiment 110, wherein $R^5$ is —OH.

Embodiment 113. The use of any one of Embodiments 110-112, wherein $R^6$ is hydrogen.

Embodiment 114. The use of any one of Embodiments 110-112, wherein $R^6$ is chloro.

Embodiment 115. The use of any one of Embodiments 110-112, wherein $R^6$ is —$NH_2$.

Embodiment 116. The use of any one of Embodiments 101-115, wherein $R^1$ is hydrogen.

Embodiment 117. The use of any one of Embodiments 101-115, wherein $R^1$ is —OH.

Embodiment 118. The use of any one of Embodiments 1-117, wherein $R^2$ is methyl.

Embodiment 119. The use of any one of Embodiments 101-117, wherein $R^2$ is ethynyl.

Embodiment 120. The use of any one of Embodiments 101-117, wherein $R^2$ is —CN.

Embodiment 121. The use of any one of Embodiments 101-103, wherein the compound of Formula I is a compound of Table 1, or a pharmaceutically acceptable salt or solvate thereof, or a tautomer thereof.

Embodiment 122. The use of any one of Embodiments 101 or 104-121 for treating the disease, disorder, or condition in a subject.

Embodiment 123. The use of any one of Embodiments 101 or 104-121 for preventing the disease, disorder, or condition in a subject.

Embodiment 124. The use of any one of Embodiments 101 or 104-121, for treating the symptom of a disease, disorder, or condition in a subject.

Embodiment 125. The use of any one of Embodiments 101 or 104-121, for preventing the symptom of a disease, disorder, or condition in a subject.

Embodiment 126. The use of any one of Embodiments 101-125, wherein the disease, disorder, or condition is a neurodegenerative disease.

Embodiment 127. The use of Embodiment 126, wherein the neurodegenerative disease is Alzheimer's disease, amyotrophic lateral sclerosis, Parkinson's disease, dementia with Lewy Bodies, multi systems atrophy, Huntington's disease, frontotemporal lobar degeneration, mild cognitive impairment, corticobasal degeneration, progressive supra nuclear palsy, Rett Syndrome, peripheral degenerative disease, or Aicardi-Goutières syndrome.

Embodiment 128. The use of any one of Embodiments 101-125, wherein the disease, disorder, or condition is an autoimmune disease.

Embodiment 129. The use of Embodiment 128, wherein the autoimmune disease is lupus, rheumatoid arthritis, Sjogrens syndrome, or multiple sclerosis.

Embodiment 130. The use of any one of Embodiments 101-125, wherein the disease, disorder, or condition is an age-associated disease.

Embodiment 131. The use of Embodiment 130, wherein the age-associated disease is Alzheimer's disease, Parkinson's disease, atherosclerosis, osteoarthritis, osteoporosis, rheumatoid arthritis, macular degeneration, peripheral degenerative disease, or skin aging.

Embodiment 132. The use of any one of Embodiments 101-125, wherein the disease, disorder, or condition is autism spectrum disorder (ADS), cardiovascular dysfunction, hearing loss, hematopoietic stem cell function, pulmonary fibrosis, schizophrenia, or vision loss.

Embodiment 133. The use of any one of Embodiments 101-125, wherein the disease, disorder, or condition is progressive supra nuclear palsy.

Embodiment 134. The use of any one of Embodiments 101-125, wherein the disease, disorder, or condition is amyotrophic lateral sclerosis.

Embodiment 135. The use of any one of Embodiments 101-125, wherein the disease, disorder, or condition is Aicardi-Goutières syndrome.

Embodiment 136. The use of any one of Embodiments 101-135 wherein one or more optional therapeutic agents is to be administered to the subject.

Embodiment 137. The use of any one of Embodiments 101-136, wherein the subject is (a) not infected with the HIV virus; (b) not suspected of being infected with the HIV virus; (c) not being treated for the HIV virus; and/or (d) not being treated to prevent the HIV virus.

Embodiment 138. The use of any one of Embodiments 101-137, wherein the compound inhibits human LINE-1 retrotransposition activity with a half maximal inhibitory concentration of 1 μM or less in an in vitro HeLa cell-based dual-luciferase assay.

Embodiment 139. The method of any one of Embodiments 3-6, wherein the retrotransposon RNA is LINE-1 RNA.

Embodiment 140. The method of any one of Embodiments 3-6, wherein the retrotransposon reverse transcriptase is ORF2p.

Embodiment 141. The method of any one of Embodiments 3-6, wherein the retrotransposon DNA is LINE-1 DNA.

Embodiment 142. The compound for use of Embodiment 62, wherein the retrotransposon RNA is LINE-1 RNA.

Embodiment 143. The compound for use of Embodiment 62, wherein the retrotransposon reverse transcriptase is ORF2p.

Embodiment 144. The compound for use of Embodiment 62, wherein the retrotransposon DNA is LINE-1 DNA.

Embodiment 145. The use of Embodiment 103, wherein the retrotransposon RNA is LINE-1 RNA.

Embodiment 146. The use of Embodiment 103, wherein the retrotransposon reverse transcriptase is ORF2p.

Embodiment 147. The use of Embodiment 103, wherein the retrotransposon DNA is LINE-1 DNA.

Embodiment 148. The method of any one of Embodiments 1-28, wherein the disease, disorder, or condition is ataxia-telangiectasia.

Embodiment 149. The method of any one of Embodiments 1-28, wherein the disease, disorder, or condition is age-related macular degeneration.

Embodiment 150. The method of any one of Embodiments 1-28, wherein the disease, disorder, or condition is systemic lupus erythematosus.

Embodiment 151. The method of any one of Embodiments 1-28, wherein the disease, disorder, or condition is IFN-associated autoimmune disease.

Embodiment 152. The method of Embodiment 151, wherein the IFN-associated autoimmune disease is psoriasis.

Embodiment 153. The method of any one of Embodiments 1-28, wherein the disease, disorder, or condition is Fanconi Anemia.

Embodiment 154. The method of any one of Embodiments 1-28, wherein the disease, disorder, or condition is idiopathic pulmonary fibrosis.

Embodiment 155. The method of any one of Embodiments 1-28, wherein the disease, disorder, or condition is cardiovascular disease.

Embodiment 156. The compound for use of any one of Embodiments 60-82, wherein the disease, disorder, or condition is ataxia-telangiectasia.

Embodiment 157. The compound for use of any one of Embodiments 60-82, wherein the disease, disorder, or condition is age-related macular degeneration.

Embodiment 158. The compound for use of any one of Embodiments 60-82, wherein the disease, disorder, or condition is systemic lupus erythematosus.

Embodiment 159. The compound for use of any one of Embodiments 60-82, wherein the disease, disorder, or condition is IFN-associated autoimmune disease.

Embodiment 160. The compound for use of Embodiment 159, wherein the IFN-associated autoimmune disease is psoriasis.

Embodiment 161. The compound for use of any one of Embodiments 60-82, wherein the disease, disorder, or condition is Fanconi Anemia.

Embodiment 162. The compound for use of any one of Embodiments 60-82, wherein the disease, disorder, or condition is idiopathic pulmonary fibrosis.

Embodiment 163. The compound for use of any one of Embodiments 60-82, wherein the disease, disorder, or condition is cardiovascular disease.

Embodiment 164. The compound for use of any one of Embodiments 101-125, wherein the disease, disorder, or condition is ataxia-telangiectasia.

Embodiment 165. The compound for use of any one of Embodiments 101-125, wherein the disease, disorder, or condition is age-related macular degeneration.

Embodiment 166. The compound for use of any one of Embodiments 101-125, wherein the disease, disorder, or condition is systemic lupus erythematosus.

Embodiment 167. The compound for use of any one of Embodiments 101-125, wherein the disease, disorder, or condition is IFN-associated autoimmune disease.

Embodiment 168. The compound for use of Embodiment 167, wherein the IFN-associated autoimmune disease is psoriasis.

Embodiment 169. The compound for use of any one of Embodiments 101-125, wherein the disease, disorder, or condition is Fanconi Anemia.

Embodiment 170. The compound for use of any one of Embodiments 101-125, wherein the disease, disorder, or condition is idiopathic pulmonary fibrosis.

Embodiment 171. The compound for use of any one of Embodiments 101-125, wherein the disease, disorder, or condition is cardiovascular disease.

Embodiment 172. The method, kit, compound for use, or use of any one of Embodiments 2-59, 61-100, or 102-171, wherein the disease, disorder, or condition is not (i) cancer; or (ii) an infectious disease.

The disclosure provides the following particular embodiments.

Embodiment 1'. A method of treating or preventing a disease, disorder, or condition caused by a pathophysiological retrotransposon-associated process in a subject in need thereof, and/or treating or preventing a symptom of the disease, disorder, or condition, the method comprising administering to the subject a therapeutically effective amount of a compound of Table 1A, or a pharmaceutically acceptable salt or solvate thereof, or a compound of Table 1B, or a pharmaceutically acceptable salt or solvate thereof, or a tautomer thereof, or tenofovir alafenamide, wherein the disease, disorder, or condition is not (i) cancer; or (ii) an infectious disease.

Embodiment 2'. A method of inhibiting a LINE-1 retrotransposition event that causes a disease, disorder, or condition in a subject in need thereof, the method comprising administering to the subject a therapeutically effective amount of a compound of Table 1A, or a pharmaceutically acceptable salt or solvate thereof, or a compound of Table 1B, or a pharmaceutically acceptable salt or solvate thereof, or a tautomer thereof, or tenofovir alafenamide wherein the disease, disorder, or condition is not (i) cancer; or (ii) an infectious disease.

Embodiment 3'. A method of treating a disease, condition, or disorder in a subject, the method comprising:

(a) determining whether an overexpression of retrotransposon RNA, retrotransposon reverse transcriptase, or retrotransposon DNA is present or absent in a biological sample taken from the subject; and (b) administering a therapeutically effective amount of a compound of Table 1A, or a pharmaceutically acceptable salt or solvate thereof, or a compound of Table 1B, or a pharmaceutically acceptable salt or solvate thereof, or a tautomer thereof, or tenofovir alafenamide, to the subject if an overexpression of retrotransposon RNA, retrotransposon reverse transcriptase, or retrotransposon DNA is present in the biological sample, wherein the disease, disorder, or condition is not (i) cancer; or (ii) an infectious disease.

Embodiment 4'. A method of identifying whether a subject having a disease, condition, or disorder is a candidate for treatment with a compound of Table 1A, or a pharmaceutically acceptable salt or solvate thereof, or a compound of Table 1B, or a pharmaceutically acceptable salt or solvate thereof, or a tautomer thereof, or tenofovir alafenamide, the method comprising:

(a) determining whether an overexpression of retrotransposon RNA, retrotransposon reverse transcriptase, or retrotransposon DNA is present or absent in a biological sample taken from the subject; and (b) identifying the subject as being a candidate for treatment if an overexpression of retrotransposon RNA, retrotransposon reverse transcriptase, or retrotransposon DNA is present; or (c) identifying the subject as not being a candidate for treatment if an overexpression of retrotransposon RNA, retrotransposon reverse transcriptase, or retrotransposon DNA is absent, wherein the disease, disorder, or condition is not (i) cancer; or (ii) an infectious disease.

Embodiment 5'. A method of predicting treatment outcome in a subject having a disease, condition, or disorder, the method comprising determining whether an overexpression of retrotransposon RNA, retrotransposon reverse transcriptase, or retrotransposon DNA is present or absent in a biological sample taken from the subject, wherein:

(a) the presence of an overexpression of retrotransposon RNA, retrotransposon reverse transcriptase, or retrotransposon DNA in the biological sample indicates that administering a compound of Table 1A, or a pharmaceutically acceptable salt or solvate thereof, or a compound of Table 1B, or a pharmaceutically acceptable salt or solvate thereof, or a tautomer thereof, or tenofovir alafenamide, to the subject will likely cause a favorable therapeutic response; and (b) the absence of an overexpression of retrotransposon RNA, retrotransposon reverse transcriptase, or retrotransposon DNA in the biological sample indicates that administering a compound of Table 1A, or a pharmaceutically acceptable salt or solvate thereof, or a compound of Table 1B, or a pharmaceutically acceptable salt or solvate thereof, or a tautomer thereof, or tenofovir alafenamide, to the subject will likely cause an unfavorable therapeutic response, wherein the disease, disorder, or condition is not (i) cancer; or (ii) an infectious disease.

Embodiment 6. A method, comprising administering a therapeutically effective amount of a compound of Table 1A, or a pharmaceutically acceptable salt or solvate thereof, or a compound of Table 1B, or a pharmaceutically acceptable salt or solvate thereof, or a tautomer thereof, or tenofovir alafenamide, wherein:

(a) the subject has a disease, condition, or disorder; and (b) the disease, condition, or disorder is characterized as having an overexpression of retrotransposon RNA, retrotransposon reverse transcriptase, or retrotransposon DNA, wherein the disease, disorder, or condition is not (i) cancer; or (ii) an infectious disease.

Embodiment 7. The method of Embodiment 1' for treating the disease, disorder, or condition in a subject.

Embodiment 8. The method of Embodiment 1' for preventing the disease, disorder, or condition in a subject.

Embodiment 9. The method of Embodiment 1' for treating the symptom of a disease, disorder, or condition in a subject.

Embodiment 10'. The method of Embodiment 1' for preventing the symptom of a disease, disorder, or condition in a subject.

Embodiment 11'. The method of any one of Embodiments 1'-10', wherein the disease, disorder, or condition is a neurodegenerative disease.

Embodiment 12'. The method of Embodiment 11', wherein the neurodegenerative disease is Alzheimer's disease, amyotrophic lateral sclerosis, Parkinson's disease, dementia with Lewy Bodies, multi systems atrophy, Huntington's disease, frontotemporal lobar degeneration, mild cognitive impairment, corticobasal degeneration, progressive supra nuclear palsy, Rett Syndrome, peripheral degenerative disease, or Aicardi-Goutières syndrome.

Embodiment 13. The method of any one of Embodiments 1'-10', wherein the disease, disorder, or condition is an autoimmune disease.

Embodiment 14'. The method of Embodiment 13', wherein the autoimmune disease is lupus, rheumatoid arthritis, Sjogrens syndrome, or multiple sclerosis.

Embodiment 15'. The method of any one of Embodiments 1'-10', wherein the disease, disorder, or condition is an age-associated disease.

Embodiment 16'. The method of Embodiment 15', wherein the age-associated disease is Alzheimer's disease, Parkinson's disease, atherosclerosis, osteoarthritis, osteoporosis, rheumatoid arthritis, macular degeneration, peripheral degenerative disease, or skin aging.

Embodiment 17'. The method of any one of Embodiments 1'-10', wherein the disease, disorder, or condition is autism spectrum disorder (ADS), cardiovascular dysfunction, hearing loss, hematopoietic stem cell function, pulmonary fibrosis, schizophrenia, or vision loss.

Embodiment 18'. The method of any one of Embodiments 1'-10', wherein the disease, disorder, or condition is progressive supra nuclear palsy.

Embodiment 19'. The method of any one of Embodiments 1'-10', wherein the disease, disorder, or condition is amyotrophic lateral sclerosis.

Embodiment 20'. The method of any one of Embodiments 1'-10', wherein the disease, disorder, or condition is Aicardi-Goutières syndrome.

Embodiment 21'. The method of any one of Embodiments 1'-10', wherein the disease, disorder, or condition is ataxia-telangiectasia.

Embodiment 22'. The method of any one of Embodiments 1'-10', wherein the disease, disorder, or condition is age-related macular degeneration.

Embodiment 23'. The method of any one of Embodiments 1'-10', wherein the disease, disorder, or condition is systemic lupus erythematosus.

Embodiment 24'. The method of any one of Embodiments 1'-10', wherein the disease, disorder, or condition is IFN-associated autoimmune disease.

Embodiment 25'. The method of Embodiment 24', wherein the IFN-associated autoimmune disease is psoriasis.

Embodiment 26'. The method of any one of Embodiments 1'-10', wherein the disease, disorder, or condition is Fanconi Anemia.

Embodiment 27'. The method of any one of Embodiments 1'-10', wherein the disease, disorder, or condition is idiopathic pulmonary fibrosis.

Embodiment 28'. The method of any one of Embodiments 1'-10', wherein the disease, disorder, or condition is cardiovascular disease.

Embodiment 29'. The method of any one of Embodiments 1'-3 or 5'-28' further comprising one or more optional therapeutic agents to the subject.

Embodiment 30'. The method of any one of Embodiments 1'-29', wherein the subject is (a) not infected with the HIV virus; (b) not suspected of being infected with the HIV virus; (c) not being treated for the HIV virus; and/or (d) not being treated to prevent the HIV virus.

Embodiment 31'. The method of any one of Embodiments 1'-30', wherein the compound inhibits human LINE-1 retrotransposition activity with a half maximal inhibitory concentration of 1 μM or less in an in vitro HeLa cell-based dual-luciferase assay.

EXAMPLES

Example 1

Synthesis of 4-amino-1-((2R,4S,5R)-5-ethynyl-4-hydroxy-5 (hydroxymethyl)tetrahydrofuran-2-yl) pyrimidin-2(1H)-one (Compound 7)

Step 1: Synthesis of (2R,3S,5R)-5-(4-benzamido-2-oxopyrimidin-1(2H)-yl)-2-ethynyl-2-(((4-methylbenzoyl)oxy)methyl)tetrahydrofuran-3-yl 4-methylbenzoate and (2R,3S,5S)-5-(4-benzamido-2-oxopyrimidin-1(2H)-yl)-2-ethynyl-2-(((4-methylbenzoyl)oxy)methyl)tetrahydrofuran-3-yl 4-methylbenzoate

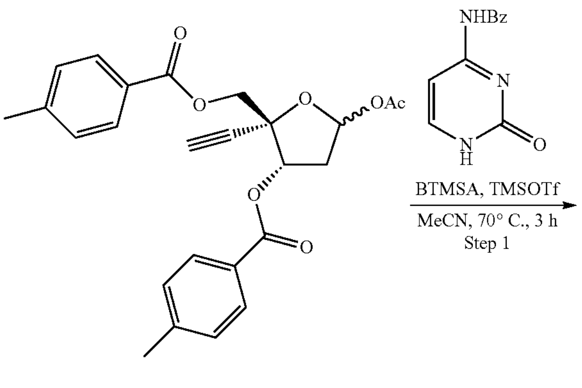

-continued

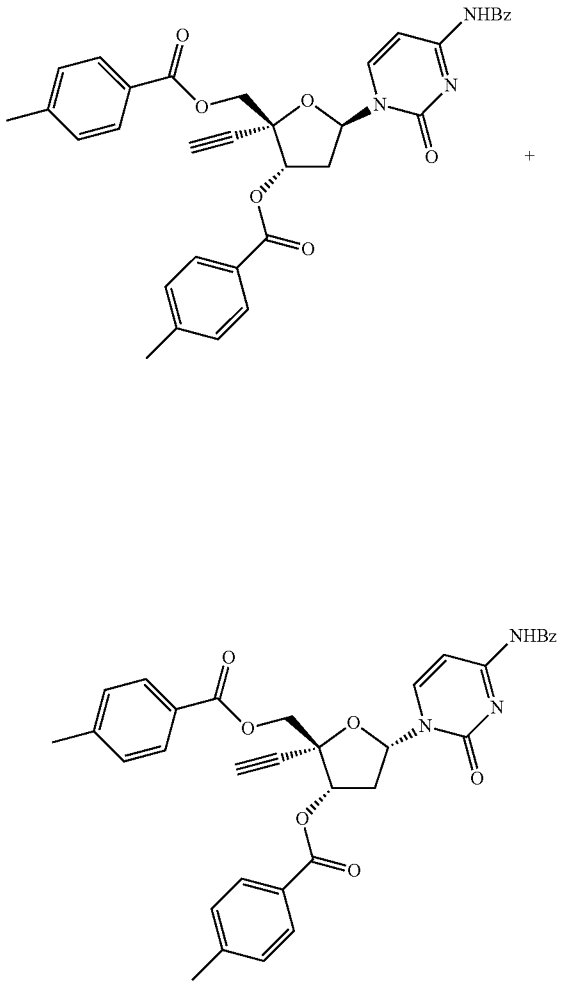

To a solution of N-(2-oxo-1H-pyrimidin-4-yl)benzamide (118 mg, 0.55 mmol), see McLaughlin et al., *Organic Letters* 19:926-929 (2017), in MeCN (20 mL) was added bis(trimethylsilyl)acetylene (BTMSA) (234 mg, 1.37 mmol) at room temperature. The resulting mixture was heated at 70° C. for 1 h. After cooling to room temperature, trimethylsilyl trifluoromethanesulfonate (TMSOTf) (122 mg, 0.55 mmol) was added and the mixture was reheated to 70° C., then a solution of [(2R,3S)-5-acetoxy-2-ethynyl-3-(4-methylbenzoyl)oxy-tetrahydrofuran-2-yl]methyl4-methylbenzoate (200 mg, 0.46 mmol) in MeCN (5 mL) was added dropwise. After stirring at 70° C. for 2 h, the reaction mixture was poured into water (50 mL) and extracted with EtOAc (50 mL×2). The layers were separated, and the organic layer was concentrated. The residue was purified by prep-TLC eluting with 50% EtOAc in petroleum ether to give [(2R,3S,5R)-5-(4-benzamido-2-oxo-pyrimidin-1-yl)-2-ethynyl-3-(4-methylbenzoyl)oxy-tetrahydrofuran-2-yl] methyl 4-methylbenzoate ($R_f$=0.5) (60 mg, 22% yield) as a white solid and [(2R,3S,5S)-5-(4-benzamido-2-oxo-pyrimidin-1-yl)-2-ethynyl-3-(4-methyl benzoyl)oxy-tetrahydrofuran-2-yl]methyl 4-methylbenzoate ($R_f$=0.4) (60 mg, 22% yield) as a white solid.

Step 2: Synthesis of 4-amino-1-((2R,4S,5R)-5-ethynyl-4-hydroxy-5 (hydroxymethyl)tetrahydrofuran-2-yl)pyrimidin-2(1H)-one

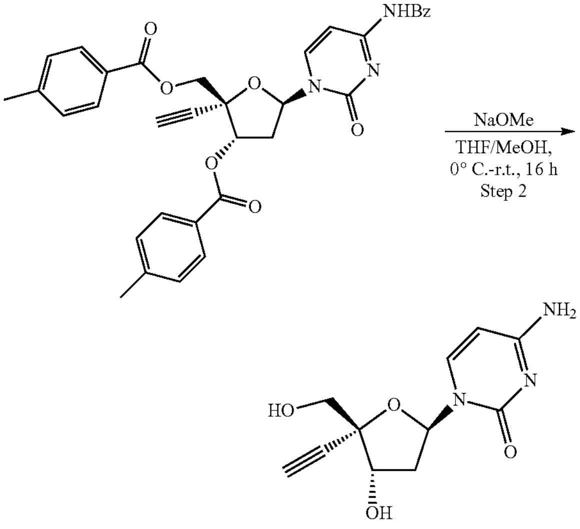

Compound 7

To a mixture of [(2R,3S,5R)-5-(4-benzamido-2-oxo-pyrimidin-1-yl)-2-ethynyl-3-(4-methylbenzoyl)oxy-tetrahydrofuran-2-yl]methyl4-methylbenzoate (60 mg, 0.1 mmol) in THF (5 mL) was added dropwise a solution of NaOMe (7 mg, 0.13 mmol) in MeOH (2 mL) at 0° C., then the resulting mixture was stirred at room temperature for 16 h. After that, the reaction mixture was concentrated under reduced pressure. The residue was purified by prep-HPLC to afford Compound 7 (8.8 mg, 34% yield) as a white solid. $^1H$ NMR (400 MHz, DMSO-$d_6$): δ7.77 (d, J=7.2 Hz, 1H), 7.17-7.11 (m, 2H), 6.15-6.12 (m, 1H), 5.71 (d, J=7.2 Hz, 1H), 5.46 (s, 1H), 5.39 (s, 1H), 4.30-4.29 (m, 1H), 3.60-3.50 (m, 2H), 3.48 (s, 1H), 2.26-2.20 (m, 1H), 2.10-2.01 (m, 1H). LCMS (ESI): m/z 252.2 $(M+H)^+$.

Example 2

Synthesis of (2R,3S,5R)-5-(6-amino-2-fluoro-9H-purin-9-yl)-2-(hydroxymethyl)-2-vinyltetrahydrofuran-3-ol (Compound 20)

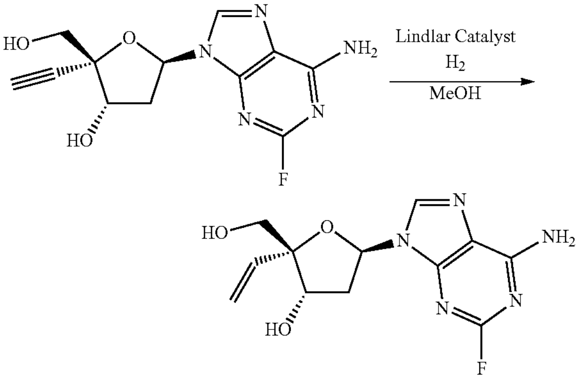

Compound 20

(2R,3S,5R)-5-(6-amino-2-fluoro-9H-purin-9-yl)-2-ethynyl-2-(hydroxymethyl)tetrahydrofuran-3-ol (79.3 mg, 270 μmol) and Lindlar Catalyst (10.0 mg, 270 μmol) were solubilized in MeOH (5.00 mL) at room temperature. Nitrogen atmosphere was bubbled through the solution for 10 min and then hydrogen was bubbled through the solution for 1 h using a balloon. The reaction was sealed and stirred for 18 h at room temperature. Then, nitrogen atmosphere was bubbled through the solution for 5 min, then the resulting mixture was filtered over a Celite® pad and it was rinsed with MeOH (15 mL). The filtrate was concentrated. The desired product was purified by prep-HPLC using a XBridge Prep C18, 5 μm 19x10 mm pre-column, CSH Prep C18 OBD, 5 μm, 30x75 mm column with MeOH (Eluent B) and AmF pH 3.8 (Eluent A) using an isocratic at 5% B for 1 min pre-run and a gradient of 5% B isocratic for 1 min, 5% B to 25% B for 11 minutes, 25% B to 100% B for 0.1 minute, hold 100% B for 2.9 minutes with a 45 mL/min flowrate and a 15 min runtime, affording (2R,3S,5R)-5-(6-amino-2-fluoro-9H-purin-9-yl)-2-(hydroxymethyl)-2-vinyltetrahydrofuran-3-ol (42.4 mg, 59%). LC-MS (ESI) m/z calcd for $C_{12}H_{14}FN_5O_3$: 295.1. Found 296.2 $[M+H]^+$. $^1$H NMR (400 MHz, DMSO-$d_6$): δ8.36 (s, 1H), 7.82 (br s, 1H), 6.24-6.22 (m, 1H), 5.99-5.92 (m, 1H), 5.41-5.36 (m, 1H), 5.31-5.30 (m, 1H), 5.23-5.20 (m, 1H), 5.11 (m, 1H), 4.64 (q, J=6.0 Hz, 1H), 3.52-3.48 (m, 2H), 2.60-2.57 (m, 1H), 2.29-2.22 (m, 1H).

Example 3

Synthesis of 4-amino-1-((2R,4S,5R)-5-ethyl-4-hydroxy-5-(hydroxymethyl)tetrahydrofuran-2-yl)pyrimidin-2(1H)-one (Compound 21)

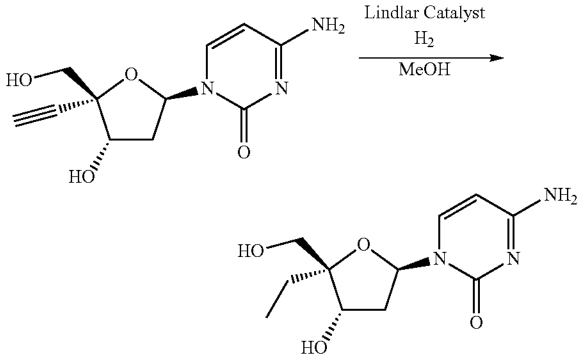

Compound 21

4-amino-1-((2R,4S,5R)-5-ethynyl-4-hydroxy-5-(hydroxymethyl)tetrahydrofuran-2-yl)pyrimidin-2(1H)-one (7.20 mg, 28.7 μmol) was dissolved in MeOH in a 5-mL vial with a rubber septum. Then solid Lindlar Catalyst (7.20 mg, 28.7 μmol) was added and the reaction mixture was flushed with $H_2$ balloon for 30 min. This reaction was stirred till full conversion to the title compound was observed by LC-MS. Then the reaction mixture was filtered through Celite® and washed with MeOH and the solvent was removed under reduced pressure, affording 4-amino-1-((2R,4S,5R)-5-ethyl-4-hydroxy-5-(hydroxymethyl)tetrahydrofuran-2-yl)pyrimidin-2(1H)-one (2.85 mg, 39%) as an off-white powder. LC-MS (ESI) m/z calcd for $C_{11}H_{16}N_3O_4$: 254.12. Found 254.4 [M−H]−. 1H-NMR (400 MHz, $CD_3OD$) δ8.05 (d, J=7.6 Hz, 1H), 6.21-6.06 (m, 1H), 5.95-5.77 (d, J=5.8 Hz, 1H), 4.41-4.33 (m, 1H), 3.73-3.60 (m, 1H), 3.60-3.47 (m, 1H), 2.52-2.11 (m, 1H), 1.85-1.47 (m, 1H), 1.04-0.84 (m, 5H).

Example 4

Human LINE-1 Retrotransposition Assay

Representative Compounds of the Disclosure were tested for inhibition of retrotransposition activity of human LINE-1 in HeLa cells according to the following procedure.

HeLa cervical cancer cells were cultivated at 37° C. in a humidified 5% $CO_2$ incubator in Dulbecco's Modified Eagle's Medium (DMEM)—high glucose, with 4500 mg/L glucose, L-glutamine, sodium pyruvate and sodium bicarbonate (Sigma), supplemented with 10% of heat inactivated fetal bovine serum (Thermo Fisher).

Assays were performed using reporter plasmid pYX017 as described (Xie, et al., 2011) with several modifications. The reporter assay was performed in 96-well white optical bottom plates. HeLa cells were seeded in wells 24 h prior to transfection and compound treatment so that cells were approximately 30% confluent on the day of transfection. Different cell plating densities were tested and a density of $2\times10^3$ cells was determined to be optimal.

Compounds were resuspended in DMSO. Serial dilutions (1:3) were prepared in DMSO. Medium containing different concentrations of the compounds were prepared by adding 2 μl of the compound dilution to 1 ml of the culture medium. The final concentration of DMSO in the medium was 0.2%.

FuGENE® HD transfection reagent (Promega, E2311, Lot 382574 and Lot 397842) was used to transfect the plasmids into the cells. The transfection reagent: DNA mixture was prepared in OpiMEM (Thermo Fisher) according to manufacturer's instructions. Different ratios of transfection reagent to DNA were tested and a ratio of 3:1 was determined to be optimal. Culture medium was removed from the cells and discarded. The transfection reagent: DNA mixture (5 μl) was mixed with the compound containing medium (100 μl/well) and this was added onto the cells of each well. Cells were incubated at 37° C./5% $CO_2$ for different incubation time. A 72 h incubation time was determined to be optimal.

Luciferase reporter activity was quantified with the Dual-Luciferase® Reporter Assay System (Promega) according to manufacturer's instructions for multiwell plates except that cells were lysed directly on the multiwell plate with 30 μl of the passive lysis buffer (PLB) for 20 min at room temperature, with gentle shaking to ensure complete cell lysis.

Firefly and Renilla luciferase signals were measured using a SpectraMax i3x Multi-Mode Microplate Reader. Integration times of 100 ms and 10 ms were used to measure the Firefly and Renilla signals respectively. Relative L1 activity is calculated as Firefly/Renilla*1000 or Firefly/Renilla*10,000. Dose response inhibition data were fit to a four parameter logistic equation using non-linear regression (using Graphpad Prism 8), to determine $IC_{50}$ values for each inhibitor.

The results are provided in Table 2.

TABLE 2

Human LINE-1 Activity Inhibition

| Compound Number | Human LINE-1 $IC_{50}$ (μM) |
|---|---|
| 2 | 0.39 |
| 4 | 0.49 |

TABLE 2-continued

| Human LINE-1 Activity Inhibition | |
|---|---|
| Compound Number | Human LINE-1 $IC_{50}$ (μM) |
| 6 | 18.56 |
| 7 | 0.0097 |
| 9 | 0.021 |
| 12 | 0.0062 |
| 13 | 0.00051 |
| 15 | 0.83 |
| 16 | >25 |
| 17 | 0.91 |
| 18 | 12.5 |
| 19 | >12.5 |
| 20 | 0.011 |
| 21 | 0.043 |
| 22 | 23.4 |
| 23 | >50 |
| 24 | 0.010 |
| 25 | 0.0036 |
| 26 | 2.05 |
| 27 | 0.0026 |
| tenofovir alafenamide | 0.01 |

Example 5

Simoa™ ORF1p and ORF2p Assays

Utilizing the same reagents as a conventional ELISA, the Simoa™ (Single Molecule Array) method has been used to measure proteins in a variety of different matrices (serum, serum/plasma, cerebral spinal fluid, urine, cell extracts etc.) at femtomolar (fg/mL) concentrations, offering a roughly 1000-fold improvement in sensitivity. This approach makes use of arrays of femtoliter-sized reaction chambers, termed single-molecule arrays (Simoa™) that can isolate and detect single enzyme molecules. Because the array volumes are approximately 2 billion times smaller than a conventional ELISA, a rapid buildup of fluorescent product is generated if a labeled protein is present. With diffusion defeated, this high local concentration of product can be readily observed. Only one single molecule is needed to reach the detection limit.

In the first step of this single-molecule immunoassay, antibody capture agents are attached to the surface of paramagnetic beads (2.7 μm diameter) that will be used to concentrate a dilute solution of molecules. The beads typically contain approximately 250,000 attachment sites so one can think of each bead as having a "lawn" of capture molecules. The beads are added to the sample solution such that there are many more beads than target molecules. Typically 500,000 beads will be added to a 100 L sample. There are two advantages for adding so many beads. First, at a roughly 10:1 bead to molecule ratio, the percentage of beads that contain a labeled immunocomplex follows a Poisson distribution. At low concentrations of protein, the Poisson distribution indicates that each bead will capture either a single immunocomplex or none. For example, if 1 fM of a protein in 0.1 mL (60,000 molecules) is captured and labeled on 500,000 beads, then 12% of the beads will carry one protein molecule and 88% will not carry any protein molecules. Second, with so many beads in solution, the bead-to-bead distance is small, such that every molecule encounters a bead in less than a minute. Diffusion of the target analyte molecules, even large proteins, occurs on a time scale such that all the molecules should in theory quickly have multiple collisions with multiple beads. In this manner, the slow binding to a fixed capture surface is avoided and the efficiency of binding increases dramatically. Beads are then washed to remove nonspecifically bound proteins, incubated with biotinylated detection antibody and then with β-galactosidase labeled streptavidin. In this manner, each bead that has captured a single protein molecule is labeled with an enzyme. Beads that do not capture a molecule remain label free.

Rather than ensemble readout, beads are loaded into arrays of 216,000 femtoliter-sized wells that have been sized to hold no more than one bead per well (4.25 μm width, 3.25 μm depth). Beads are added in the presence of substrate, and wells are subsequently sealed with oil and imaged. Simoa permits the detection of very low concentrations of enzyme labels by confining the fluorophores generated by individual enzymes to extremely small volumes (~40 fL), ensuring a high local concentration of fluorescent product molecules. If a target analyte has been captured (immunocomplex formed), then the substrate will be converted to a fluorescent product by captured enzyme label. The ratio of the number of wells containing a bead with an enzyme label to the total number of wells containing a bead corresponds to the analyte concentration in the sample. By acquiring two fluorescence images of the array, it is possible to demonstrate an increase in signal thereby confirming the presence of a true immunocomplex, and those beads associated with a single enzyme molecule ("on" well) can be distinguished from those not associated with an enzyme ("off" well). The protein concentration in the test sample is determined by counting the number of wells containing both a bead and fluorescent product relative to the total number of wells containing beads. As Simoa enables concentration to be determined digitally rather than by using the total analog signal, this approach to detecting single immunocomplexes has been termed digital ELISA. The ability of digital ELISA to measure much lower concentrations of proteins than conventional ELISA derives from two effects: (i) the high sensitivity of Simoa to enzyme label and (ii) the low background signals that can be achieved by digitizing the detection of proteins. For antibodies of given affinity, the sensitivity of the immunoassay will be determined by the assay background. The high label sensitivity and decreased label concentration helps reduce nonspecific binding to the capture surface, resulting in much lower background signals.

Utilizing ORF1p monoclonal antibodies, a Simoa™ assay to detect ORF1p levels in spiked serum from healthy volunteers (serum from healthy volunteers does not contain detectable concentrations of ORF1p), cancer cell lysates, and peripheral blood mononuclear cell (PBMC) lysates of healthy volunteers. The ORF1p monoclonal antibodies used in these studies were MABC1152 from Millipore-Sigma and ab246317 from Abcam.

The lower limit of detection (LLOD) was determined at 22 fg/mL and the lower limit of quantitation (LLOQ) was determined at 93 fg/mL in the spiked serum from healthy volunteers. The LLOD was determined at 18 fg/mL and the LLOQ was determined at 70 fg/mL in the cancer cell lysates. The LLOD was determined at 17 fg/mL and the LLOQ was determined at 68 fg/mL in the PBMC lysates of healthy volunteers.

Using the same procedure with ORF2p monoclonal antibodies, a Simoa™ assay can be used to detect ORF2p levels in biological samples taken from a subject.

Having now fully described the compounds, methods, kits, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications, and publications cited herein are fully incorporated by reference herein in their entirety.

What is claimed is:

1. A method of treating a disease, disorder, or condition selected from the group consisting of Alzheimer's disease, amyotrophic lateral sclerosis, Parkinson's disease, dementia with Lewy Bodies, multi systems atrophy, Huntington's disease, frontotemporal lobar degeneration, mild cognitive impairment, corticobasal degeneration, progressive supra nuclear palsy, Rett Syndrome, peripheral degenerative disease, and Aicardi-Goutières in a subject in need thereof, the method comprising administering to the subject a therapeutically effective amount of:

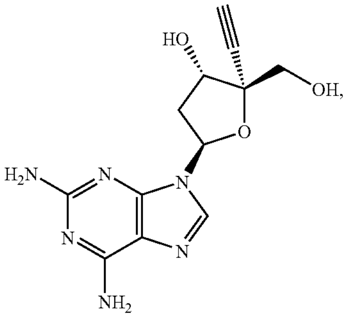

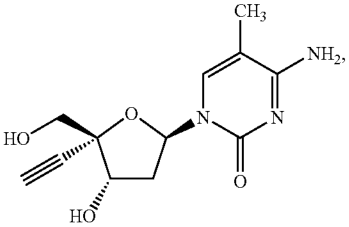

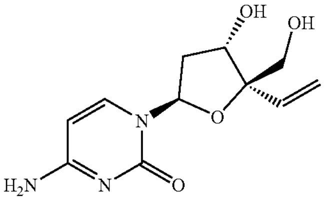
,

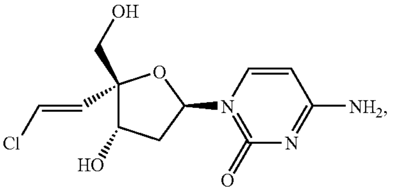
or

-continued

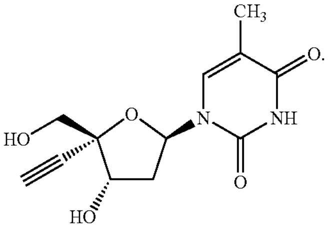

2. The method of claim 1, wherein the disease, disorder, or condition is progressive supra nuclear palsy.

3. The method of claim 1, wherein the disease, disorder, or condition is amyotrophic lateral sclerosis.

4. The method of claim 1, wherein the disease, disorder, or condition is Aicardi-Goutières syndrome.

5. The method of claim 1 further comprising administering one or more optional therapeutic agents to the subject.

6. The method of claim 1, wherein the subject is (a) not infected with the HIV virus; (b) not suspected of being infected with the HIV virus; (c) not being treated for the HIV virus; and/or (d) not being treated to prevent the HIV virus.

7. The method of claim 1, wherein the compound inhibits human LINE-1 retrotransposition activity with a half maximal inhibitory concentration of 1 μM or less in an in vitro HeLa cell-based dual-luciferase assay.

8. The method of claim 1, wherein the disease, disorder, or condition is Alzheimer's disease.

9. The method of claim 1, wherein the disease, disorder, or condition is Parkinson's disease.

10. The method of claim 1, wherein the disease, disorder, or condition is dementia with Lewy Bodies.

11. The method of claim 1, wherein the disease, disorder, or condition is multi systems atrophy.

12. The method of claim 1, wherein the disease, disorder, or condition is Huntington's disease.

13. The method of claim 1, wherein the disease, disorder, or condition is frontotemporal lobar degeneration.

14. The method of claim 1, wherein the disease, disorder, or condition is mild cognitive impairment.

15. The method of claim 1, wherein the disease, disorder, or condition is corticobasal degeneration.

16. The method of claim 1, wherein the disease, disorder, or condition is Rett Syndrome.

17. The method of claim 1, wherein the disease, disorder, or condition is peripheral degenerative disease.

* * * * *